United States Patent
Bryan et al.

(10) Patent No.: US 10,899,774 B2
(45) Date of Patent: Jan. 26, 2021

(54) IRAK4 MODULATORS

(71) Applicant: Genentech, Inc., South San Francisco, CA (US)

(72) Inventors: Marian C. Bryan, South San Francisco, CA (US); Joy Drobnick, South San Francisco, CA (US); Alberto Gobbi, South San Francisco, CA (US); Tamiko Katsumoto, Millbrae, CA (US); Naomi S. Rajapaksa, South San Francisco, CA (US); James Richard Kiefer, Jr., South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 16/715,959

(22) Filed: Dec. 16, 2019

(65) Prior Publication Data

US 2020/0115388 A1    Apr. 16, 2020

Related U.S. Application Data

(63) Continuation of application No. PCT/EP2018/066317, filed on Jun. 19, 2018.

(60) Provisional application No. 62/522,969, filed on Jun. 21, 2017.

(51) Int. Cl.
| | |
|---|---|
| *C07D 498/04* | (2006.01) |
| *C07D 413/14* | (2006.01) |
| *C07D 417/14* | (2006.01) |
| *C07D 471/04* | (2006.01) |
| *C07D 487/04* | (2006.01) |
| *C07D 491/048* | (2006.01) |
| *C07D 495/04* | (2006.01) |
| *C07D 513/04* | (2006.01) |

(52) U.S. Cl.
CPC ......... *C07D 498/04* (2013.01); *C07D 413/14* (2013.01); *C07D 417/14* (2013.01); *C07D 471/04* (2013.01); *C07D 487/04* (2013.01); *C07D 491/048* (2013.01); *C07D 495/04* (2013.01); *C07D 513/04* (2013.01)

(58) Field of Classification Search
CPC .................................................. C07D 498/04
See application file for complete search history.

(56) References Cited

U.S. PATENT DOCUMENTS

2012/0015962 A1    1/2012    Arora et al.

FOREIGN PATENT DOCUMENTS

| WO | 2012/007375 A1 | 1/2012 |
|---|---|---|
| WO | 2015/193846 A1 | 12/2015 |
| WO | 2016/144846 A1 | 9/2016 |
| WO | 2016/144848 A1 | 9/2016 |
| WO | 2016/144849 A1 | 9/2016 |
| WO | 2017/108723 A2 | 6/2017 |

OTHER PUBLICATIONS

Chaudhary, D., et al., "Recent Advances in the Discovery of Small Molecule Inhibitors of Interlekin-1 Receptor-Associated Kinase 4 (IRAK4) as a Therapeutic Target for Inflammation and Oncology Disorders" J Med Chem 58(1):96-110 (Jan. 8, 2015).
"International Preliminary Report on Patentability—PCT/EP2018/066317" pp. 1-8 (dated Jan. 2, 2020).
"International Search Report—PCT/EP2018/066317" pp. 1-7 (dated Aug. 1, 2018).
Lim, J., et al., "Discovery of 5-Amino-N-(1H-parazol-4y1)pyrazolo(1.5-a)pyrimidine-3carboxamide Inhibitors of IRAK4" ACS Med Chem Lett 6(6):683-688 (Jun. 11, 2015).

*Primary Examiner* — Golam M Shameem

(57) ABSTRACT

Compounds of Formula 0, and stereoisomers and pharmaceutically acceptable salts thereof, as well as methods of use as Interleukin-1 Receptor Associated Kinase (IRAK4) inhibitors are described herein.

18 Claims, No Drawings

IRAK4 MODULATORS

CROSS-REFERENCE TO RELATED APPLICATION

This application is a continuation application of PCT/EP2018/066317, filed Jun. 19, 2018 that claims the benefit of priority to U.S. Application Ser. No. 62/522,969, filed Jun. 21, 2017, both of which are incorporated by reference herein in their entirety.

FIELD OF THE INVENTION

This invention pertains to compounds useful for inhibition of Interleukin-1 Receptor Associated Kinase 4 (IRAK4).

BACKGROUND OF THE INVENTION

TIR-domain (Toll-Interleukin 1 Receptor-domain) containing cell surface receptors such as the Toll-like receptors (TLR) and the IL-1 and IL-18 receptors play critical roles in innate immunity and have been implicated in the pathogenesis of autoimmunity. TLRs, for example, recognize pathogenic or endogenous ligands and provide a requisite signal for dendritic cell maturation and antigen presentation to T cell. Similarly, proteins that mediate signaling from these receptors have also been shown to play important roles in the pathogenesis of autoimmune disorders. For example mice deficient in MyD88, an adaptor protein that directly interacts with the TIR domain, are more susceptible to bacterial, fungal and parasitic infections. In addition, MyD88 deficient mice are resistant to experimental autoimmune encephalomyelitis (EAE) and streptococcal cell wall-induced arthritis.

The Interleukin-1 Receptor Associated Kinase (IRAK) family is comprised of four family members IRAK1, IRAK2, IRAK3 (also termed IRAK-M), and IRAK4. These proteins are characterized by a typical N-terminal death domain that mediates interaction with MyD88-family adaptor proteins and a centrally located kinase domain. Whereas IRAK1 and IRAK4 have kinase activity, IRAK2 and IRAK3 are catalytically inactive. Upon activation of their upstream cognate receptors, IRAK4 is thought to phosphorylate IRAK1, resulting in the activation and autophosphorylation of IRAK1 and subsequent phosphorylation of downstream substrates. The hyperphosphorylation of IRAK1 directs its dissociation from the receptor complex and its eventual ubiquitylation and proteasomal degradation. Phosphorylation of downstream substrates such as Pellino-2 ultimately leads to the activation of the MAPKs such as p38 and c-Jun N-terminal kinase (JNK) and NF-kB followed by production of pro-inflammatory cytokines, chemokines, and destructive enzyme.

The role of IRAK4 in innate immunity and in the pathogenesis of autoimmune diseases is emerging. See, e.g., Li et al., "IRAK-4: A novel member of the IRAK family with the properties of an IRAK-kinase," *PNAS* 2002, 99(8), 5567-5572; and Flannery et al., "The interleukin-1 receptor-associated kinases: Critical regulators of innate immune signaling," *Biochem Pharm* 2010, 80(12), 1981-1991. Patients with destabilizing or null mutations in IRAK4 demonstrate defects in TLR signaling and the production of pro-inflammatory cytokines such as IL-1 and TNF as well as antiviral cytokines such as IFNα and IFNβ. These patients demonstrate an increased susceptibility to gram-positive bacterial infections although they are generally resistant to gram-negative bacterial, viral, and fungal infections. Similarly, IRAK4 deficient mice have defects in TLR- and IL-1-mediated cytokine production and exhibit an increased susceptibility to infection. IRAK1 deficient mice demonstrate a loss of responsiveness to lipopolysaccharides (LPS), IL-1, and IL-18 as well as impaired Th1 development. These mice were resistant to experimental autoimmune encephalomyelitis, exhibiting little or no CNS inflammation.

Accordingly, compounds that modulate the function of IRAK4 represent an attractive approach to the development of therapeutic agents for the treatment of diseases such as inflammatory, cell proliferative and immune-related conditions and diseases associated with IRAK-mediated signal transduction, such as rheumatoid arthritis, inflammatory bowel disease, multiple sclerosis, lupus, diabetes, obesity, allergic disease, psoriasis, asthma, graft rejection, cancer and sepsis.

SUMMARY OF THE INVENTION

One aspect of the invention includes a compound of Formula 0:

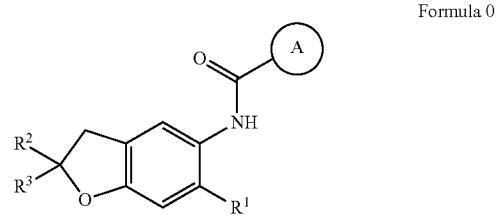

Formula 0 or a stereoisomer or pharmaceutically acceptable salt thereof,
wherein:
$R^1$ is $C_{1-6}$alkoxy, oxetanyl, —$NR^aR^b$, or a 6-membered heteroaryl that is optionally substituted with $R^c$;
$R^2$ is methyl, hydroxymethyl, or 2-hydroxyprop-2-yl and $R^3$ is methyl; or $R^2$ and $R^3$ taken together with the carbon to which they are attached form a 6-membered heterocyclic group that is optionally substituted with $C_{1-3}$ alkyl;
ring A is a 5-membered heteroaryl, a 6-membered heteroaryl, a 6-membered saturated or partially saturated heterocyclic group, or a 9-membered bicyclic heteroaryl that comprises at least two heteroatoms selected form the group consisting of N, O, and S, wherein ring A is optionally substituted with $R^d$; provided ring A is not an optionally substituted 9-membered bicyclic heteroaryl of the following formula,

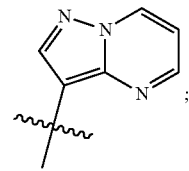 [SMILES: *c1cnn2cccnc12]

$R^a$ and $R^b$ are, independently at each occurrence, $C_{1-6}$alkyl, or $R^a$ and $R^b$ are taken together to form a 6-membered heterocyclic group that is optionally substituted with $R^c$;
each $R^c$ is, independently at each occurrence, halogen; oxo; CN; —$S(O)_{1-2}R^n$; OH; $C_{1-6}$alkoxy; —$NR^eR^f$; —C(O)($C_{1-3}$alkyl); —($C_{0-3}$alkyl)C(O)$NR^gR^h$; —$S(O)_{1-2}NR^eR^f$; —OP(O)(O$C_{1-3}$alkyl)$_2$; $C_{3-10}$cycloalkyl group optionally substituted with OH or halogen; a 3-11 membered saturated or partially saturated heterocyclic group optionally substituted with oxo or $C_{1-3}$alkyl; a 5-6 membered monocyclic heteroaryl ring optionally substituted with halogen, oxo, CN, OH, $C_{1-4}$alkoxy, —$NR^eR^f$, or $C_{1-4}$alkyl optionally substituted with halogen, or OH; or $C_{1-4}$alkyl optionally substituted with halogen, oxo, CN, OH, —O—$C_{1-3}$ alkyl, —S—$C_{1-3}$alkyl, —$SO_2$—$C_{1-3}$alkyl, —$NR^eR^f$, —C(O)$NR^eR^f$, phenyl, $C_{3-10}$cycloalkyl, a 3-11 membered saturated or partially saturated heterocyclic group optionally substituted with oxo, $C_{1-3}$ alkyl, or a 5-6 membered monocyclic heteroaryl ring optionally substituted with oxo, halogen, or $C_{1-3}$alkyl;

each $R^d$ is, independently at each occurrence, halogen; oxo; CN; —$OR^n$; —$S(O)_{1-2}R^n$; OH; $C_{1-6}$alkoxy; —$NR^eR^f$; —C(O)($C_{1-3}$alkyl); —($C_{0-3}$alkyl)C(O)$NR^gR^h$; —$S(O)_{1-2}NR^eR^f$; —OP(O)($OC_{1-3}$alkyl)$_2$; $C_{3-10}$cycloalkyl group optionally substituted with OH or halogen; a 3-11 membered saturated or partially saturated heterocyclic group optionally substituted with oxo or $C_{1-3}$alkyl; a 5-6 membered monocyclic heteroaryl ring optionally substituted with halogen, oxo, CN, OH, $C_{1-4}$alkoxy, —$NR^eR^f$, or $C_{1-4}$alkyl optionally substituted with halogen, or OH; or $C_{1-4}$alkyl optionally substituted with halogen, oxo, CN, OH, —O—$C_{1-3}$ alkyl, —S—$C_1$-3alkyl, —$SO_2$—$C_{1-3}$alkyl, —$NR^eR^f$, —C(O)$NR^eR^f$, phenyl, $C_{3-10}$cycloalkyl, a 3-11 membered saturated or partially saturated heterocyclic group optionally substituted with oxo, $C_{1-3}$ alkyl, or a 5-6 membered monocyclic heteroaryl ring optionally substituted with oxo, halogen, or $C_{1-3}$alkyl;

$R^e$, $R^f$, $R^g$ and $R^h$ are, independently at each occurrence, hydrogen, $C_{1-6}$alkyl, $C_{3-6}$ cycloalkyl group, —($C_{0-3}$alkyl)-phenyl, a 3-11 membered saturated heterocyclic group, a 5-6 membered monocyclic heteroaryl ring, —C(O)$R^n$, —C(O)$OR^n$, —C(O)$NR^kR^m$, or —$S(O)_{1-2}R^n$, or $R^g$ and $R^h$ are taken together to form a 5-8 membered heterocyclic group, wherein any alkyl, cycloalkyl group, phenyl, heterocyclic group, or heteroaryl ring is independently optionally substituted with halogen, oxo, CN, $C_{1-3}$alkyl, $C_{1-3}$haloalkyl, $C_{1-3}$ alkoxy, $C_{1-3}$haloalkoxy, —$OR^n$, —$NR^kR^m$, or a 5-6 membered monocyclic heteroaryl ring;

$R^k$ and $R^m$ are, independently at each occurrence, hydrogen, $C_{1-3}$alkyl, or $C_3$-6cycloalkyl group, wherein any alkyl or cycloalkyl group is independently optionally substituted with halogen, oxo, CN, OH, $C_{1-3}$alkyl, $C_{1-3}$haloalkyl, $C_{1-3}$alkoxy, or $C_1$-3haloalkoxy;

$R^n$ is, independently at each occurrence, hydrogen, $C_{1-6}$alkyl, $C_{3-10}$cycloalkyl group, or a 3-11 membered saturated heterocyclic group, wherein any alkyl, cycloalkyl group, or heterocyclic group is independently optionally substituted with halogen, oxo, CN, OH, $C_{1-3}$alkyl, $C_{1-3}$haloalkyl, $C_{1-3}$alkoxy, $C_{1-3}$haloalkoxy, —$OR^p$, or —$NR^gR^h$; and $R^p$ is, independently at each occurrence, hydrogen, $C_{1-6}$alkyl or $C_{3-6}$cycloalkyl group, wherein any alkyl or cycloalkyl group is independently optionally substituted with halogen, oxo, CN, OH, $C_{1-3}$alkyl, $C_{1-3}$haloalkyl, $C_{1-3}$alkoxy, or $C_{1-3}$haloalkoxy.

Also provided is a pharmaceutical composition that comprises a compound of the invention and a pharmaceutically acceptable carrier, diluent or excipient.

Another aspect includes a method of preventing, treating, or lessening the severity of a disease or condition responsive to the inhibition of IRAK4 in a patient, comprising administering to the patient a therapeutically effective amount of a compound, stereoisomer, or pharmaceutically acceptable salt of the invention.

Another aspect includes a method for treating cancer in a patient, comprising administering to the patient a therapeutically effective amount of a compound, stereoisomer, or pharmaceutically acceptable salt of the invention.

Another aspect includes a method for treating an inflammatory or autoimmune disease in a patient, comprising administering to the patient a therapeutically effective amount of a compound, stereoisomer, or pharmaceutically acceptable salt of the invention. In one aspect the disease is selected from the group consisting of Crohn's disease, ulcerative colitis, inflammatory bowel disease (IBD), asthma, graft versus host disease, allograft rejection, chronic obstructive pulmonary disease (COPD), rheumatoid arthritis, systemic lupus erythematosus, lupus nephritis, cutaneous lupus, psoriasis, systemic onset juvenile idiopathic arthritis, multiple sclerosis, neuropathic pain, gout, and gouty arthritis.

Another aspect includes a method for treating endometriosis in a patient, comprising administering to the patient a therapeutically effective amount of a compound, stereoisomer, or pharmaceutically acceptable salt of the invention.

Another aspect includes the use of a compound, stereoisomer, or pharmaceutically acceptable salt of the invention in therapy, such as the treatment of an inflammatory disease, an autoimmune disease, endometriosis, or cancer.

Another aspect includes the use of a compound, stereoisomer, or pharmaceutically acceptable salt of the invention in the treatment of an inflammatory disease.

Another aspect includes the use of a compound, stereoisomer, or pharmaceutically acceptable salt of the invention for the preparation of a medicament for the treatment of an inflammatory disease.

Another aspect includes a compound, stereoisomer, or pharmaceutically acceptable salt of the invention for use in the treatment of an inflammatory disease.

Another aspect includes the use of a compound, stereoisomer, or pharmaceutically acceptable salt of the invention in the treatment of cancer.

Another aspect includes the use of a compound, stereoisomer, or pharmaceutically acceptable salt of the invention for the preparation of a medicament for the treatment of cancer.

Another aspect includes a compound, stereoisomer, or pharmaceutically acceptable salt of the invention for use in the treatment of cancer.

Another aspect includes the use of a compound, stereoisomer, or pharmaceutically acceptable salt of the invention in the treatment of endometriosis.

Another aspect includes the use of a compound, stereoisomer, or pharmaceutically acceptable salt of the invention for the preparation of a medicament for the treatment of endometriosis.

Another aspect includes a compound, stereoisomer, or pharmaceutically acceptable salt of the invention for use in the treatment of endometriosis.

Another aspect includes a method of inhibiting IRAK4 in a cell, ex vivo, comprising contacting the cell with a compound, stereoisomer, or pharmaceutically acceptable salt of the invention.

Another aspect includes a method of inhibiting IRAK4 in a patient in need of therapy, comprising administering to the patient a compound, stereoisomer, or pharmaceutically acceptable salt of the invention.

Another aspect includes the use of a compound, stereoisomer, or pharmaceutically acceptable salt of the invention to inhibit IRAK4.

Another aspect includes the use of a compound, stereoisomer, or pharmaceutically acceptable salt of the invention for the preparation of a medicament for inhibiting IRAK4.

Another aspect includes a compound, stereoisomer, or pharmaceutically acceptable salt of the invention for use in inhibiting IRAK4.

Another aspect includes a kit for treating a disease or disorder responsive to the inhibition of IRAK4. The kit can comprise a first pharmaceutical composition comprising a compound, stereoisomer, or pharmaceutically acceptable salt of the invention, and instructions for use.

DETAILED DESCRIPTION OF THE INVENTION

Definitions

"Halogen" or "halo" refers to F, Cl, Br or I. Additionally, terms such as "haloalkyl," are meant to include monohaloalkyl and polyhaloalkyl.

The term "alkyl" refers to a saturated linear or branched-chain monovalent hydrocarbon radical, wherein the alkyl radical may be optionally substituted. In one example, the alkyl radical is one to eighteen carbon atoms ($C_1$-$C_{18}$). In other examples, the alkyl radical is $C_0$-$C_6$, $C_0$-$C_5$, $C_0$-$C_3$, $C_1$-$C_{12}$, $C_1$-$C_{10}$, $C_1$-$C_8$, $C_1$-$C_6$, $C_1$-$C_5$, $C_1$-$C_4$, or $C_1$-$C_3$. $C_0$ alkyl refers to a bond. Examples of alkyl groups include methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —CH($CH_3$)$_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —CH($CH_3$)$CH_2CH_3$), 2-methyl-2-propyl (t-Bu, t-butyl, —C($CH_3$)$_3$), 1-pentyl (n-pentyl, —$CH_2CH_2CH_2CH_2CH_3$), 2-pentyl (—CH($CH_3$)$CH_2CH_2CH_3$), 3-pentyl (—CH($CH_2CH_3$)$_2$), 2-methyl-2-butyl (—C($CH_3$)$_2CH_2CH_3$), 3-methyl-2-butyl (—CH($CH_3$)CH($CH_3$)$_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—CH($CH_3$)$CH_2CH_2CH_2CH_3$), 3-hexyl (—CH($CH_2CH_3$)($CH_2CH_2CH_3$)), 2-methyl-2-pentyl (—C($CH_3$)$_2CH_2CH_2CH_3$), 3-methyl-2-pentyl (—CH($CH_3$)CH($CH_3$)$CH_2CH_3$), 4-methyl-2-pentyl (—CH($CH_3$)$CH_2CH$($CH_3$)$_2$), 3-methyl-3-pentyl (—C($CH_3$)($CH_2CH_3$)$_2$), 2-methyl-3-pentyl (—CH($CH_2CH_3$)CH($CH_3$)$_2$), 2,3-dimethyl-2-butyl (—C($CH_3$)$_2CH(CH_3)_2$), 3,3-dimethyl-2-butyl (—CH($CH_3$)C($CH_3$)$_3$, 1-heptyl (—$CH_2CH_2CH_2CH_2CH_2CH_2CH_3$) and 1-octyl (—$CH_2CH_2CH_2CH_2CH_2CH_2CH_2CH_3$). In some embodiments, substituents for "optionally substituted alkyls" include one to four instances of F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, phenyl, piperidinyl, piperizinyl, and pyrimidinyl, wherein the alkyl, phenyl and heterocyclic portions thereof may be optionally substituted, such as by one to four instances of substituents selected from this same list.

"Aryl" refers to a carbocyclic aromatic group, whether or not fused to one or more groups, having the number of carbon atoms designated, or if no number is designated, up to 14 carbon atoms. One example includes aryl groups having 6-14 carbon atoms. Another example includes aryl groups having 6-10 carbon atoms. Examples of aryl groups include phenyl, naphthyl, biphenyl, phenanthrenyl, naphthacenyl, 1,2,3,4-tetrahydronaphthalenyl, 1H-indenyl, 2,3-dihydro-1H-indenyl, and the like (see, e.g., Lang's Handbook of Chemistry (Dean, J. A., ed.) 13$^{th}$ ed. Table 7-2 [1985]). A particular aryl is phenyl. Substituted phenyl or substituted aryl means a phenyl group or aryl group substituted with one, two, three, four or five substituents, for example, 1-2, 1-3 or 1-4 substituents, such as chosen from groups specified herein (see "optionally substituted" definition), such as F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, phenyl, piperidinyl, piperizinyl, and pyrimidinyl, wherein the alkyl, phenyl and heterocyclic portions thereof may be optionally substituted, such as by one to four instances of substituents selected from this same list. Examples of the term "substituted phenyl" include a mono- or di(halo)phenyl group such as 2-chlorophenyl, 2-bromophenyl, 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl, 2,4-difluorophenyl and the like; a mono- or di(hydroxy)phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a mono- or di(alkyl)phenyl group such as 4-methylphenyl, 2,4-dimethylphenyl, 2-methylphenyl, 4-(isopropyl)phenyl, 4-ethylphenyl, 3-(n-propyl)phenyl and the like; a mono or di(alkoxy)phenyl group, for example, 3,4-dimethoxyphenyl, 3-methoxy-4-benzyloxyphenyl, 3-ethoxyphenyl, 4-(isopropoxy)phenyl, 4-(t-butoxy)phenyl, 3-ethoxy-4-methoxyphenyl and the like; 3- or 4-trifluoromethylphenyl; a mono- or dicarboxyphenyl or (protected carboxy)phenyl group such 4-carboxyphenyl, a mono- or di(hydroxymethyl)phenyl or (protected hydroxymethyl)phenyl such as 3-(protected hydroxymethyl)phenyl or 3,4-di(hydroxymethyl)phenyl; a mono- or di(aminomethyl)phenyl or (protected aminomethyl)phenyl such as 2-(aminomethyl)phenyl or 2,4-(protected aminomethyl)phenyl; or a mono- or di(N-(methylsulfonylamino))phenyl such as 3-(N-methylsulfonylamino))phenyl. Also, the term "substituted phenyl" represents disubstituted phenyl groups where the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, 2-chloro-5-difluoromethoxy and the like, as well as trisubstituted phenyl groups where the substituents are different, for example 3-methoxy-4-benzyloxy-6-methyl sulfonylamino, 3-methoxy-4-benzyloxy-6-phenyl sulfonylamino, and tetrasubstituted phenyl groups where the substituents are different such as 3-methoxy-4-benzyloxy-5-methyl-6-phenyl sulfonylamino.

The terms "compound(s) of the invention," and "compound(s) of the present invention" and the like, unless otherwise indicated, include compounds of Formula 0 and the compounds of Table 1 herein, including stereoisomers (including atropisomers), geometric isomers, tautomers, solvates, metabolites, isotopes, salts (e.g., pharmaceutically acceptable salts), and prodrugs thereof. In some embodiments, solvates, metabolites, isotopes or prodrugs are excluded, or any combination thereof.

"Cycloalkyl" refers to a non-aromatic, saturated or partially unsaturated hydrocarbon ring group wherein the cycloalkyl group may be optionally substituted independently with one or more substituents described herein. In one example, the cycloalkyl group is 3 to 12 carbon atoms ($C_3$-$C_{12}$). In other examples, cycloalkyl is $C_3$-$C_8$, $C_3$-$C_{10}$ or $C_5$-$C_{10}$. In other examples, the cycloalkyl group, as a monocycle, is $C_3$-$C_8$, $C_3$-$C_6$ or $C_5$-$C_6$. In another example, the cycloalkyl group, as a bicycle, is $C_7$-$C_{12}$. In another example, the cycloalkyl group, as a spiro system, is $C_5$-$C_{12}$. Examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl and cyclododecyl. Exemplary arrangements of bicyclic cycloalkyls having 7 to 12 ring atoms include, but are not limited to, [4,4], [4,5], [5,5], [5,6] or [6,6] ring systems. Exemplary bridged bicyclic cycloalkyls include, but are not limited to, bicyclo[2.2.1]heptane, bicyclo[2.2.2]octane and bicyclo[3.2.2]nonane. Examples of spiro cycloalkyl include, spiro[2.2]pentane, spiro[2.3]hexane, spiro[2.4]heptane, spiro[2.5]octane and spiro[4.5]decane. In some embodiments, substituents for "optionally substituted cycloalkyls" include one to four instances of F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, isopropyl, butyl, isobutyl, cyclopropyl, methoxy, ethoxy, propoxy, oxo, trifluoromethyl, difluoromethyl, sulfonylamino, methanesulfonylamino, phenyl, piperidinyl, piperizinyl, and pyrimidinyl, wherein the alkyl, aryl and heterocyclic portions thereof may be optionally substituted, such as by one to four instances of substituents selected from this same list.

"Heterocyclic group", "heterocyclic", "heterocycle", "heterocyclyl", or "heterocyclo" are used interchangeably and refer to any mono-, bi-, tricyclic or spiro, saturated, partially saturated or unsaturated, aromatic (heteroaryl) or non-aromatic (e.g., heterocycloalkyl), ring system, having 3 to 20 ring atoms, where the ring atoms are carbon, and at least one atom in the ring or ring system is a heteroatom selected from nitrogen, sulfur or oxygen. If any ring atom of a cyclic system is a heteroatom, that system is a heterocycle, regardless of the point of attachment of the cyclic system to the rest of the molecule. In one example, heterocyclyl includes 3-11 ring atoms ("members") and includes monocycles, bicycles, tricycles and spiro ring systems, wherein the ring atoms are carbon, where at least one atom in the ring or ring system is a heteroatom selected from nitrogen, sulfur or oxygen. In one example, heterocyclyl includes 1 to 4 heteroatoms. In one example, heterocyclyl includes 1 to 3 heteroatoms. In another example, heterocyclyl includes 3- to 7-membered monocycles having 1-2, 1-3 or 1-4 heteroatoms selected from nitrogen, sulfur or oxygen. In another example, heterocyclyl includes 4- to 6-membered monocycles having 1-2, 1-3 or 1-4 heteroatoms selected from nitrogen, sulfur or oxygen. In another example, heterocyclyl includes 3-membered monocycles. In another example, heterocyclyl includes 4-membered monocycles. In another example, heterocyclyl includes 5-6 membered monocycles, e.g., 5-6 membered heteroaryl. In another example, heterocyclyl includes 3-11 membered heterocycloyalkyls, such as 4-11 membered heterocycloalkyls. In some embodiments, a heterocycloalkyl includes at least one nitrogen. In one example, the heterocyclyl group includes 0 to 3 double bonds. Any nitrogen or sulfur heteroatom may optionally be oxidized (e.g., NO, SO, $SO_2$), and any nitrogen heteroatom may optionally be quaternized (e.g., $[NR_4]^+Cl^-$, $[NR_4]^+OH^-$). Example heterocycles are oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydrofuranyl, dihydrothienyl, tetrahydrothienyl, imidazolidinyl, piperidinyl, piperazinyl, isoquinolinyl, tetrahydroisoquinolinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, 1,6-dihydroimidazol[4,5-d]pyrrolo[2,3-b]pyridinyl, thiazinyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5]decanyl, 1-azaspiro[4.5]decan-2-only, azaspiro[5.5]undecanyl, tetrahydroindolyl, octahydroindolyl, tetrahydroisoindolyl, tetrahydroindazolyl, 1,1-dioxohexahydrothiopyranyl. Examples of 5-membered heterocycles containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocycles containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Example benzo-fused 5-membered heterocycles are benzoxazol-2-yl, benzthiazol-2-yl and benzimidazol-2-yl. Example 6-membered heterocycles contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are other example heterocycle groups. Heterocycles may be optionally substituted. For example, substituents for "optionally substituted heterocycles" include one to four instances of F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, phenyl, piperidinyl, piperizinyl, and pyrimidinyl, wherein the alkyl, aryl and heterocyclic portions thereof may be optionally substituted, such as by one to four instances of substituents selected from this same list.

"Heteroaryl" refers to any mono-, bi-, or tricyclic ring system where at least one ring is a 5- or 6-membered aromatic ring containing from 1 to 4 heteroatoms selected from nitrogen, oxygen, and sulfur, and in an example embodiment, at least one heteroatom is nitrogen. See, for example, Lang's Handbook of Chemistry (Dean, J. A., ed.)

13th ed. Table 7-2 [1985]. Included in the definition are bicyclic groups where any of the above heteroaryl rings are fused to an aryl ring, a heterocyclic group, or a cycloalkyl, wherein the bicyclic group is joined to the remainder of the molecule at any position of the bicyclic group. In one embodiment, heteroaryl includes 5-6 membered monocyclic aromatic groups where one or more ring atoms is nitrogen, sulfur or oxygen. Example heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, tetrazolo[1,5-b]pyridazinyl, imidazol[1,2-a]pyrimidinyl and purinyl, as well as benzo-fused derivatives, for example benzoxazolyl, benzofuryl, benzothiazolyl, benzothiadiazolyl, benzotriazolyl, benzoimidazolyl and indolyl. Heteroaryl groups can be optionally substituted. In some embodiments, substituents for "optionally substituted heteroaryls" include one to four instances of F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, iso-propyl, butyl, isobutyl, cyclopropyl, methoxy, ethoxy, propoxy, trifluoromethyl, difluoromethyl, sulfonylamino, methanesulfonylamino, phenyl, piperidinyl, piperizinyl, and pyrimidinyl, wherein the alkyl, phenyl and heterocyclic portions thereof may be optionally substituted, such as by one to four instances of substituents selected from this same list.

In particular embodiments, a heterocyclyl group is attached at a carbon atom of the heterocyclyl group. By way of example, carbon bonded heterocyclyl groups include bonding arrangements at position 2, 3, 4, 5, or 6 of a pyridine ring, position 3, 4, 5, or 6 of a pyridazine ring, position 2, 4, 5, or 6 of a pyrimidine ring, position 2, 3, 5, or 6 of a pyrazine ring, position 2, 3, 4, or 5 of a furan, tetrahydrofuran, thiofuran, thiophene, pyrrole or tetrahydropyrrole ring, position 2, 4, or 5 of an oxazole, imidazole or thiazole ring, position 3, 4, or 5 of an isoxazole, pyrazole, or isothiazole ring, position 2 or 3 of an aziridine ring, position 2, 3, or 4 of an azetidine ring, position 2, 3, 4, 5, 6, 7, or 8 of a quinoline ring or position 1, 3, 4, 5, 6, 7, or 8 of an isoquinoline ring.

In certain embodiments, the heterocyclyl group is N-attached. By way of example, nitrogen bonded heterocyclyl or heteroaryl groups include bonding arrangements at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The term "alkoxy" refers to a linear or branched monovalent radical represented by the formula —OR in which R is alkyl, as defined herein. Alkoxy groups include methoxy, ethoxy, propoxy, isopropoxy, mono-, di- and tri-fluoromethoxy and cyclopropoxy. "Haloalkoxy" refers to a haloalkyl group, as that term is defined herein, as R.

The term "alkanoyl" refers to group (alkyl)-C(=O)—, wherein alkyl is as defined herein. For example, $C_1$-$C_6$alkanoyl refers to a group of formula ($C_1$-$C_5$alkyl)-C(=O)—. Alkanoyl groups include, formyl, acetyl, propanoyl, isopropanoyl, butanoyl, isobutanoyl, pentanoyl, 3-methylpentanoyl, and hexanoyl.

"Optionally substituted" unless otherwise specified means that a group may be unsubstituted or substituted with one or more (e.g., 0, 1, 2, 3, 4, or 5 or more, or any range derivable therein) of the substituents listed for that group in which said substituents may be the same or different. In an embodiment, an optionally substituted group has 1 substituent. In another embodiment an optionally substituted group has 2 substituents. In another embodiment an optionally substituted group has 3 substituents. In another embodiment an optionally substituted group has 4 substituents. In another embodiment an optionally substituted group has 5 substituents.

As used herein a wavy line "～" that intersects a bond in a chemical structure indicate the point of attachment of the atom to which the wavy bond is connected in the chemical structure to the remainder of a molecule, or to the remainder of a fragment of a molecule. In some embodiments, an arrow together with an asterisk is used in the manner of a wavy line to indicate a point of attachment.

In certain embodiments, divalent groups are described generically without specific bonding configurations. It is understood that the generic description is meant to include both bonding configurations, unless specified otherwise. For example, in the group $R^1$-$R^2$-$R^3$, if the group $R^2$ is described as —$CH_2C(O)$—, then it is understood that this group can be bonded both as $R^1$—$CH_2C(O)$—$R^3$, and as $R^1$—C(O)$CH_2$—$R^3$, unless specified otherwise.

The phrase "pharmaceutically acceptable" refers to molecular entities and compositions that do not produce an adverse, allergic or other untoward reaction when administered to an animal, such as, for example, a human, as appropriate.

Compounds of the invention may be in the form of a salt, such as a pharmaceutically acceptable salt. "Pharmaceutically acceptable salts" include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, benzenesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particular base addition salts are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particular organic non-toxic bases include isopropylamine, diethylamine, ethanolamine, tromethamine, dicyclohexylamine, choline, and caffeine.

In some embodiments, a salt is selected from a hydrochloride, hydrobromide, trifluoroacetate, sulphate, phosphate, acetate, fumarate, maleate, tartrate, lactate, citrate, pyruvate, succinate, oxalate, methanesulphonate, p-toluenesulphonate, bisulphate, benzenesulphonate, ethanesulphonate, malonate, xinafoate, ascorbate, oleate, nicotinate, saccharinate, adipate, formate, glycolate, palmitate, L-lactate, D-lactate, aspartate, malate, L-tartrate, D-tartrate, stearate, furoate (e.g., 2-furoate or 3-furoate), napadisylate (naphthalene-1,5-disulfonate or naphthalene-1-(sulfonic acid)-5-sulfonate), edisylate (ethane-1,2-disulfonate or ethane-1-(sulfonic acid)-2-sulfonate), isothionate (2-hydroxyethylsulfonate), 2-mesitylenesulphonate, 2-naphthalenesulphonate, 2,5-dichlorobenzenesulphonate, D-mandelate, L-mandelate, cinnamate, benzoate, adipate, esylate, malonate, mesitylate (2-mesitylenesulphonate), napsylate (2-naphthalenesulfonate), camsylate (camphor-10-sulphonate, for example (1S)-(+)-10-camphorsulfonic acid salt), glutamate, glutarate, hippurate (2-(benzoylamino)acetate), orotate, xylate (p-xylene-2-sulphonate), and pamoic (2,2'-dihydroxy-1,1'-dinaphthylmethane-3,3'-dicarboxylate).

A "sterile" formulation is aseptic or free from all living microorganisms and their spores.

"Stereoisomers" refer to compounds that have identical chemical constitution, but differ with regard to the arrangement of the atoms or groups in space. Stereoisomers include diastereomers, enantiomers, conformers and the like.

"Chiral" refers to molecules which have the property of non-superimposability of the mirror image partner, while the term "achiral" refers to molecules which are superimposable on their mirror image partner.

"Diastereomer" refers to a stereoisomer with two or more centers of chirality and whose molecules are not mirror images of one another. Diastereomers have different physical properties, e.g., melting points, boiling points, spectral properties or biological activities. Mixtures of diastereomers may separate under high resolution analytical procedures such as electrophoresis and chromatography such as HPLC.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Certain compounds of the invention can exist in unsolvated forms as well as solvated forms, including hydrated forms. A "solvate" refers to an association or complex of one or more solvent molecules and a compound of the present invention. Examples of solvents that form solvates include water, isopropanol, ethanol, methanol, DMSO, ethyl acetate, acetic acid, and ethanolamine. Certain compounds of the invention can exist in multiple crystalline or amorphous forms. In general, all physical forms are intended to be within the scope of the present invention. The term "hydrate" refers to the complex where the solvent molecule is water.

A "metabolite" refers to a product produced through metabolism in the body of a specified compound or salt thereof. Such products can result, for example, from the oxidation, reduction, hydrolysis, amidation, deamidation, esterification, deesterification, enzymatic cleavage, and the like, of the administered compound.

Metabolite products typically are identified by preparing a radiolabelled (e.g., $^{14}C$ or $^{3}H$) isotope of a compound of the invention, administering it in a detectable dose (e.g., greater than about 0.5 mg/kg) to an animal such as rat, mouse, guinea pig, monkey, or to a human, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

"Amino-protecting group" as used herein refers to a derivative of the groups commonly employed to block or protect an amino group while reactions are carried out on other functional groups on the compound. Examples of such protecting groups include carbamates, amides, alkyl and aryl groups, and imines, as well as many N-heteroatom derivatives which can be removed to regenerate the desired amine group. Particular amino protecting groups are Pmb (p-Methoxybenzyl), Boc (tert-Butyloxycarbonyl), Fmoc (9-Fluorenylmethyloxycarbonyl) and Cbz (Carbenzyloxy). Further examples of these groups are found in T. W. Greene and P. G. M. Wuts, "Protecting Groups in Organic Synthesis, $3^{rd}$ ed., John Wiley & Sons, Inc., 1999. The term "protected amino" refers to an amino group substituted with one of the above amino-protecting groups.

"Carboxy-protecting group" as used herein refers to those groups that are stable to the conditions of subsequent reaction(s) at other positions of the molecule, which may be removed at the appropriate point without disrupting the remainder of the molecule, to give the unprotected carboxy-group. Examples of carboxy protecting groups include, ester groups and heterocyclyl groups. Ester derivatives of the carboxylic acid group may be employed to block or protect the carboxylic acid group while reactions are carried out on other functional groups on the compound. Examples of such ester groups include substituted arylalkyl, including substituted benzyls, such as 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, alkyl or substituted alkyl esters such as methyl, ethyl, t-butyl allyl or t-amyl, triphenylmethyl (trityl), 4-methoxytrityl, 4,4'-dimethoxytrityl, 4,4',4"-trimethoxytrityl, 2-phenylprop-2-yl, thioesters such as t-butyl thioester, silyl esters such as trimethylsilyl, t-butyldimethylsilyl esters, phenacyl, 2,2,2-trichloroethyl, beta-(trimethylsilyl)ethyl, beta-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl, and like moieties. Another example of carboxy-protecting groups are heterocyclyl groups such as 1,3-oxazolinyl. Further examples of these groups are found in T. W. Greene and P. G. M. Wuts, "Protecting Groups in Organic Synthesis, $3^{rd}$ ed., John Wiley & Sons, Inc., 1999. The term "protected carboxy" refers to a carboxy group substituted with one of the above carboxy-protecting groups.

"Hydroxy-protecting group" as used herein refers to a derivative of the hydroxy group commonly employed to block or protect the hydroxy group while reactions are carried out on other functional groups on the compound. Examples of such protecting groups include tetrahydropyranyloxy, benzoyl, acetoxy, carbamoyloxy, benzyl, and silylethers (e.g., TBS, TBDPS) groups. Further examples of these groups are found in T. W. Greene and P. G. M. Wuts, "Protecting Groups in Organic Synthesis, $3^{rd}$ ed., John Wiley & Sons, Inc., 1999. The term "protected hydroxy" refers to a hydroxy group substituted with one of the above hydroxy-protecting groups.

Compounds of the invention may contain one or more asymmetric carbon atoms. Accordingly, the compounds may exist as diastereomers, enantiomers or mixtures thereof. The syntheses of the compounds may employ racemates, diastereomers or enantiomers as starting materials or as intermediates. Mixtures of particular diastereomeric compounds may be separated, or enriched in one or more particular diastereomers, by chromatographic or crystallization methods. Similarly, enantiomeric mixtures may be separated, or enantiomerically enriched, using the same techniques or others known in the art. Each of the asymmetric carbon or nitrogen atoms may be in the R or S configuration and both of these configurations are within the scope of the invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined. Unless otherwise specified, if solid wedges or dashed lines are used, relative stereochemistry is intended.

Another aspect includes prodrugs of the compounds of the invention including known amino-protecting and carboxy-protecting groups which are released, for example hydrolyzed, to yield the compound of the present invention under physiologic conditions.

The term "prodrug" refers to a precursor or derivative form of a pharmaceutically active substance that is less efficacious to the patient compared to the parent drug and is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). Prodrugs include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, and 5-fluorocytosine and 5-fluorouridine prodrugs.

A particular class of prodrugs are compounds in which a nitrogen atom in an amino, amidino, aminoalkyleneamino, iminoalkyleneamino or guanidino group is substituted with a hydroxy group, an alkylcarbonyl (—CO—R) group, an alkoxycarbonyl (—CO—OR), or an acyloxyalkyl-alkoxycarbonyl (—CO—O—R—O—CO—R) group where R is a monovalent or divalent group, for example alkyl, alkylene or aryl, or a group having the Formula —C(O)—O—CP1P2-haloalkyl, where P1 and P2 are the same or different and are hydrogen, alkyl, alkoxy, cyano, halogen, alkyl or aryl. In a particular embodiment, the nitrogen atom is one of the nitrogen atoms of the amidino group of the compounds of the invention. Prodrugs may be prepared by reacting a compound of the present invention with an activated group, such as acyl groups, to bond, for example, a nitrogen atom in the compound to the exemplary carbonyl of the activated acyl group. Examples of activated carbonyl compounds are those containing a leaving group bonded to the carbonyl group, and include, for example, acyl halides, acyl amines, acyl pyridinium salts, acyl alkoxides, acyl phenoxides such as p-nitrophenoxy acyl, dinitrophenoxy acyl, fluorophenoxy acyl, and difluorophenoxy acyl. The reactions are generally carried out in inert solvents at reduced temperatures such as −78 to about 50° C. The reactions may also be carried out in the presence of an inorganic base, for example potassium carbonate or sodium bicarbonate, or an organic base such as an amine, including pyridine, trimethylamine, triethylamine, triethanolamine, or the like.

Additional types of prodrugs are also encompassed. For instance, a free carboxyl group of a compound of the invention can be derivatized as an amide or alkyl ester. As another example, compounds of the invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$—$C_6$)alkoxycarbonyloxymethyl, N—($C_1$-$C_6$)alkoxycarbonylaminomethyl, succinoyl, ($C_1$-$C_6$)alkanoyl, alpha-amino($C_1$-$C_4$)alkanoyl, arylacyl and alpha-aminoacyl, or alpha-aminoacyl-alpha-aminoacyl, where each alpha-aminoacyl group is independently selected from the naturally occurring L-amino acids, P(O)(OH)$_2$, —P(O)(O($C_1$-$C_6$)alkyl)₂ or glycosyl (the radical resulting from the removal of a hydroxyl group of the hemiacetal form of a carbohydrate).

"Leaving group" refers to a portion of a first reactant in a chemical reaction that is displaced from the first reactant in the chemical reaction. Examples of leaving groups include, but are not limited to, halogen atoms, alkoxy and sulfonyloxy groups. Example sulfonyloxy groups include, but are not limited to, alkylsulfonyloxy groups (for example methyl sulfonyloxy (mesylate group) and trifluoromethylsulfonyloxy (triflate group)) and arylsulfonyloxy groups (for example p-toluenesulfonyloxy (tosylate group) and p-nitrosulfonyloxy (nosylate group)).

A "subject," "individual," or "patient" is a vertebrate. In certain embodiments, the vertebrate is a mammal. Mammals include, but are not limited to, farm animals (such as cows), sport animals, pets (such as guinea pigs, cats, dogs, rabbits and horses), primates, mice and rats. In certain embodiments, a mammal is a human. In embodiments comprising administration of a compound of to a patient, the patient is typically in need thereof.

The terms "inhibiting" and "reducing," or any variation of these terms, includes any measurable decrease or complete inhibition to achieve a desired result. For example, there may be a decrease of about, at most about, or at least about 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of activity (e.g., IRAK4 activity) compared to normal.

In some embodiments, a compound of Formula 0, such as a compound of Table 1, is selective for inhibition of IRAK4 over IRAK1. By "selective for inhibition" it is meant that the compound is at least a 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, better inhibitor of IRAK4 activity compared to IRAK1 activity, or is at least a 2-, 3-, 4-, 5-, 10-, 25-, 50-, 100-, 250-, or 500-fold better inhibitor of IRAK4 activity compared to IRAK1 activity.

A "therapeutically effective amount" means an amount of a compound of the present invention, such as a compound of Formula 0 (e.g., a compound of Table 1), that (i) treats or prevents the particular disease, condition or disorder, or (ii) attenuates, ameliorates or eliminates one or more symptoms of the particular disease, condition, or disorder, and optionally (iii) prevents or delays the onset of one or more symptoms of the particular disease, condition or disorder described herein. In some embodiments, the therapeutically effective amount is an amount sufficient to decrease or alleviate the symptoms of an autoimmune or inflammatory disease (e.g., lupus). In some embodiments, a therapeutically effective amount is an amount of a chemical entity described herein sufficient to significantly decrease the activity or number of B-cells. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; or relieve to some extent one or more of the symptoms associated with the cancer. To the extent the drug may prevent growth or kill existing cancer cells, it may be cytostatic or cytotoxic. For cancer therapy, efficacy can, for example, be measured by assessing the time to disease progression (TTP) or determining the response rate (RR).

"Treatment" (and variations such as "treat" or "treating") refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, stabilized (i.e., not worsening) state of disease, decreasing the rate of disease progression, amelioration or palliation of the disease state, prolonging survival as compared to expected survival if not receiving treatment and remission or improved prognosis. In some embodiments, compounds of the invention, are used to delay development of a disease or disorder or to slow the progression of a disease or disorder. Those in need of treatment include those already with the condition or disorder as well as those prone to have the condition or disorder, (for example, through a genetic mutation) or those in which the condition or disorder is to be prevented.

"Inflammatory disorder" refers to any disease, disorder or syndrome in which an excessive or unregulated inflammatory response leads to excessive inflammatory symptoms, host tissue damage, or loss of tissue function. "Inflammatory disorder" also refers to a pathological state mediated by influx of leukocytes or neutrophil chemotaxis.

"Inflammation" refers to a localized, protective response elicited by injury or destruction of tissues, which serves to destroy, dilute, or wall off (sequester) both the injurious agent and the injured tissue. Inflammation is notably associated with influx of leukocytes or neutrophil chemotaxis. Inflammation can result from infection with pathogenic organisms and viruses and from noninfectious means such as trauma or reperfusion following myocardial infarction or stroke, immune responses to foreign antigens, and autoimmune responses. Accordingly, inflammatory disorders amenable to treatment with a compound of the present invention, encompass disorders associated with reactions of the specific defense system as well as with reactions of the nonspecific defense system.

"Specific defense system" refers to the component of the immune system that reacts to the presence of specific antigens. Examples of inflammation resulting from a response of the specific defense system include the classical response to foreign antigens, autoimmune diseases, and delayed type hypersensitivity responses mediated by T-cells. Chronic inflammatory diseases, the rejection of solid transplanted tissue and organs, e.g., kidney and bone marrow transplants, and graft versus host disease (GVHD), are further examples of inflammatory reactions of the specific defense system.

The term "nonspecific defense system" refers to inflammatory disorders that are mediated by leukocytes that are incapable of immunological memory (e.g., granulocytes, and macrophages). Examples of inflammation that result, at least in part, from a reaction of the nonspecific defense system include inflammation associated with conditions such as adult (acute) respiratory distress syndrome (ARDS) or multiple organ injury syndromes; reperfusion injury; acute glomerulonephritis; reactive arthritis; dermatoses with acute inflammatory components; acute purulent meningitis or other central nervous system inflammatory disorders such as stroke; thermal injury; inflammatory bowel disease; granulocyte transfusion associated syndromes; and cytokine-induced toxicity.

"Autoimmune disease" refers to any group of disorders in which tissue injury is associated with humoral or cell-mediated responses to the body's own constituents. Non-limiting examples of autoimmune diseases include rheumatoid arthritis, lupus and multiple sclerosis.

"Allergic disease" as used herein refers to any symptoms, tissue damage, or loss of tissue function resulting from allergy. "Arthritic disease" as used herein refers to any disease that is characterized by inflammatory lesions of the joints attributable to a variety of etiologies. "Dermatitis" as used herein refers to any of a large family of diseases of the skin that are characterized by inflammation of the skin attributable to a variety of etiologies. "Transplant rejection" as used herein refers to any immune reaction directed against grafted tissue, such as organs or cells (e.g., bone marrow), characterized by a loss of function of the grafted and surrounding tissues, pain, swelling, leukocytosis, and thrombocytopenia. The therapeutic methods of the present invention include methods for the treatment of disorders associated with inflammatory cell activation.

"Inflammatory cell activation" refers to the induction by a stimulus (including, but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatibility antigens or cell adhesion molecules) in inflammatory cells (including but not limited to monocytes, macrophages, T lymphocytes, B lymphocytes, granulocytes (i.e., polymorphonuclear leukocytes such as neutrophils, basophils, and eosinophils), mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory disorder.

In some embodiments, inflammatory disorders which can be treated according to the methods of this invention include, but are not limited to, asthma, rhinitis (e.g., allergic rhinitis), allergic airway syndrome, atopic dermatitis, bronchitis, rheumatoid arthritis, psoriasis, lupus, chronic obstructive pulmonary disease (COPD), contact dermatitis, chronic obstructive pulmonary disease and delayed hypersensitivity reactions.

The terms "cancer" and "cancerous", "neoplasm", and "tumor" and related terms refer to or describe the physiological condition in mammals that is typically characterized by unregulated cell growth. A "tumor" comprises one or more cancerous cells. Examples of cancer include carcinoma, blastoma, sarcoma, seminoma, glioblastoma, melanoma, leukemia, and myeloid or lymphoid malignancies. More particular examples of such cancers include squamous cell cancer (e.g., epithelial squamous cell cancer) and lung cancer including small-cell lung cancer, non-small cell lung cancer ("NSCLC"), adenocarcinoma of the lung and squamous carcinoma of the lung. Other cancers include skin, keratoacanthoma, follicular carcinoma, hairy cell leukemia, buccal cavity, pharynx (oral), lip, tongue, mouth, salivary gland, esophageal, larynx, hepatocellular, gastric, stomach, gastrointestinal, small intestine, large intestine, pancreatic, cervical, ovarian, liver, bladder, hepatoma, breast, colon, rectal, colorectal, genitourinary, biliary passage, thyroid, papillary, hepatic, endometrial, uterine, salivary gland, kidney or renal, prostate, testis, vulval, peritoneum, anal, penile, bone, multiple myeloma, B-cell lymphoma, diffuse large B-Cell lymphoma (DLBCL), central nervous system, brain, head and neck, Hodgkin's, and associated metastases. Examples of neoplastic disorders include myeloproliferative disorders, such as polycythemia vera, essential thrombocytosis, myelofibrosis, such as primary myelofibrosis, and chronic myelogenous leukemia (CML).

A "chemotherapeutic agent" is an agent useful in the treatment of a given disorder, for example, cancer or inflammatory disorders. Examples of chemotherapeutic agents are well-known in the art and include examples such as those disclosed in U.S. Publ. Appl. No. 2010/0048557, incorporated herein by reference. Additionally, chemotherapeutic agents include pharmaceutically acceptable salts, acids or derivatives of any of chemotherapeutic agents, as well as combinations of two or more of them.

Unless otherwise stated, structures depicted herein are also meant to include compounds that differ only in the presence of one or more isotopically enriched atoms. Exemplary isotopes that can be incorporated into compounds of the invention, include isotopes of hydrogen, carbon, nitrogen, oxygen, phosphorus, sulfur, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I, and $^{125}$I, respectively. Isotopically-labeled compounds (e.g., those labeled with $^3$H and $^{14}$C) can be useful in compound or substrate tissue distribution assays. Tritiated (i.e., $^3$H) and carbon-14 (i.e., $^{14}$C) isotopes can be useful for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements). In some embodiments, in compounds of the invention, one or more carbon atoms are replaced by $^{13}$C- or $^{14}$C-enriched carbon. Positron emitting isotopes such as $^{15}$O, $^{13}$N, $^{11}$C, and $^{18}$F are useful for positron emission tomography (PET) studies to examine substrate receptor occupancy. Isotopically labeled compounds can generally be prepared by following procedures analogous to those disclosed in the Schemes or in the Examples herein, by substituting an isotopically labeled reagent for a non-isotopically labeled reagent.

It is specifically contemplated that any limitation discussed with respect to one embodiment of the invention may apply to any other embodiment of the invention. Furthermore, any compound or composition of the invention may be used in any method of the invention, and any method of the invention may be used to produce or to utilize any compound or composition of the invention.

If any discrepancy exists between a structure and its name, the structure prevails.

The use of the term "or" is used to mean "and/or" unless explicitly indicated to refer to alternatives only or the alternative are mutually exclusive, although the disclosure supports a definition that refers to only alternatives and "and/or."

Throughout this application, the term "about" is used to indicate that a value includes the standard deviation of error for the device or method being employed to determine the value.

As used herein, "a" or "an" means one or more, unless clearly indicated otherwise. As used herein, "another" means at least a second or more.

Headings used herein are intended only for organizational purposes.

IRAK4 Inhibitors

As noted, one aspect of the invention includes a compound of Formula 0:

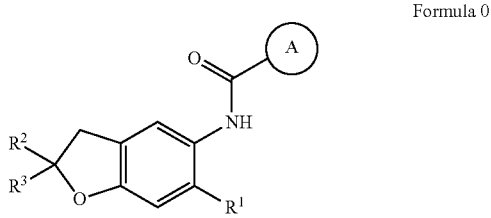

Formula 0 or a stereoisomer or pharmaceutically acceptable salt thereof, wherein:

$R^1$ is $C_{1-6}$alkoxy, oxetanyl, —$NR^aR^b$, or a 6-membered heteroaryl that is optionally substituted with $R^c$;

$R^2$ is methyl, hydroxymethyl, or 2-hydroxypropan-2-yl and $R^3$ is methyl; or $R^2$ and $R^3$ taken together with the carbon to which they are attached form a 6-membered heterocyclic group that is optionally substituted with $C_{1-3}$alkyl;

ring A is a 5-membered heteroaryl, a 6-membered heteroaryl, a 6-membered saturated or partially saturated heterocyclic group, or a 9-membered bicyclic heteroaryl that comprises at least two heteroatoms selected form the group consisting of N, O, and S, wherein ring A is optionally substituted with $R^d$; provided ring A is not an optionally substituted 9-membered bicyclic heteroaryl of the following formula,

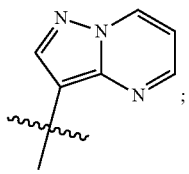 [SMILES: *c1cnn2cccnc12]

$R^a$ and $R^b$ are, independently at each occurrence, $C_{1-6}$alkyl, or $R^a$ and $R^b$ are taken together to form a 6-membered heterocyclic group that is optionally substituted with $R^c$;

each $R^c$ is, independently at each occurrence, halogen; oxo; CN; —$S(O)_{1-2}R^n$; OH; $C_{1-6}$alkoxy; —$NR^eR^f$; —$C(O)$($C_{1-3}$alkyl); —($C_{0-3}$alkyl)$C(O)NR^gR^h$; —$S(O)_{1-2}NR^eR^f$; —$OP(O)(OC_{1-3}$alkyl$)_2$; $C_{3-10}$cycloalkyl group optionally substituted with OH or halogen; a 3-11 membered saturated or partially saturated heterocyclic group optionally substituted with oxo or $C_{1-3}$alkyl; a 5-6 membered monocyclic heteroaryl ring optionally substituted with halogen, oxo, CN, OH, $C_{1-4}$alkoxy, —$NR^eR^f$, or $C_{1-4}$alkyl optionally substituted with halogen, or OH; or $C_{1-4}$alkyl optionally substituted with halogen, oxo, CN, OH, —O—$C_{1-3}$ alkyl, —S—$C_{1-3}$ alkyl, —$SO_2$—$C_{1-3}$alkyl, —$NR^eR^f$, —$C(O)$$NR^eR^f$, phenyl, $C_{3-10}$cycloalkyl, a 3-11 membered saturated or partially saturated heterocyclic group optionally substituted with oxo, $C_{1-3}$ alkyl, or a 5-6 membered monocyclic heteroaryl ring optionally substituted with oxo, halogen, or $C_{1-3}$alkyl;

each $R^d$ is, independently at each occurrence, halogen; oxo; CN; —$OR^n$; —$S(O)_{1-2}R$; OH; $C_{1-6}$alkoxy; —$NR^eR^f$; —$C(O)$($C_{1-3}$alkyl); —($C_{0-3}$alkyl)$C(O)NR^gR^h$; —$S(O)_{1-2}NR^eR^f$; —$OP(O)(OC_{1-3}$alkyl$)_2$; $C_{3-10}$cycloalkyl group optionally substituted with OH or halogen; a 3-11 membered saturated or partially saturated heterocyclic group optionally substituted with oxo or $C_{1-3}$alkyl; a 5-6 membered monocyclic heteroaryl ring optionally substituted with halogen, oxo, CN, OH, $C_{1-4}$alkoxy, —$NR^eR^f$, or $C_{1-4}$alkyl optionally substituted with halogen, or OH; or $C_{1-4}$alkyl optionally substituted with halogen, oxo, CN, OH, —O—$C_{1-3}$ alkyl, —S—$C_{1-3}$ alkyl, —$SO_2$—$C_{1-3}$alkyl, —$NR^eR^f$, —$C(O)$$NR^eR^f$, phenyl, $C_{3-10}$cycloalkyl, a 3-11 membered saturated or partially saturated heterocyclic group optionally substituted with oxo, $C_{1-3}$ alkyl, or a 5-6 membered monocyclic heteroaryl ring optionally substituted with oxo, halogen, or $C_{1-3}$alkyl;

$R^e$, $R^f$, $R^g$ and $R^h$ are, independently at each occurrence, hydrogen, $C_{1-6}$alkyl, $C_3$-6cycloalkyl group, —($C_{0-3}$alkyl)-phenyl, a 3-11 membered saturated heterocyclic group, a 5-6 membered monocyclic heteroaryl ring, —$C(O)R$, —$C(O)OR^n$, —$C(O)NR^kR^m$, or —$S(O)_{1-2}R^n$, or $R^g$ and $R^h$ are taken together to form a 5-8 membered heterocyclic group, wherein any alkyl, cycloalkyl group, phenyl, heterocyclic group, or heteroaryl ring is independently optionally substituted with halogen, oxo, CN, $C_{1-3}$alkyl, $C_{1-3}$haloalkyl, $C_{1-3}$ alkoxy, $C_{1-3}$haloalkoxy, —$OR^n$, —$NR^kR^m$, or a 5-6 membered monocyclic heteroaryl ring;

$R^k$ and $R^m$ are, independently at each occurrence, hydrogen, $C_{1-3}$alkyl, or $C_{3-6}$cycloalkyl group, wherein any alkyl or cycloalkyl group is independently optionally substituted with halogen, oxo, CN, OH, $C_{1-3}$alkyl, $C_{1-3}$haloalkyl, $C_{1-3}$alkoxy, or $C_1$-3haloalkoxy;

$R^n$ is, independently at each occurrence, hydrogen, $C_{1-6}$alkyl, $C_{3-10}$cycloalkyl group, or a 3-11 membered saturated heterocyclic group, wherein any alkyl, cycloalkyl group, or heterocyclic group is independently optionally substituted with halogen, oxo, CN, OH, $C_1$-3alkyl, $C_{1-3}$haloalkyl, $C_{1-3}$alkoxy, $C_{1-3}$haloalkoxy, —$OR^p$, or —$NR^gR^h$; and $R^p$ is, independently at each occurrence, hydrogen, $C_{1-6}$alkyl or $C_{3-6}$cycloalkyl group, wherein any alkyl or cycloalkyl group is independently optionally substituted with halogen, oxo, CN, OH, $C_{1-3}$alkyl, $C_{1-3}$haloalkyl, $C_{1-3}$alkoxy, or $C_{1-3}$haloalkoxy In some embodiments, $R^1$ is $C_{1-6}$alkoxy, —$NR^aR^b$, or a 6-membered heteroaryl that is optionally substituted with $R^c$.

In some embodiments, $R^1$ is —$NR^aR^b$.

In some embodiments, $R^a$ and $R^b$ are taken together to form a 6-membered heterocyclic group that is optionally substituted with $R^c$.

In some embodiments, $R^a$ and $R^b$ are taken together to form a morpholino group that is optionally substituted with $R^c$.

In some embodiments, $R^1$ is a 6-membered heteroaryl that is optionally substituted with $R^c$.

In some embodiments, $R^1$ is pyridyl that is optionally substituted with $R^c$.

In some embodiments, $R^1$ is selected from the group consisting of

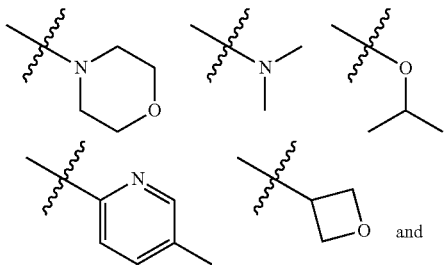

and

-continued

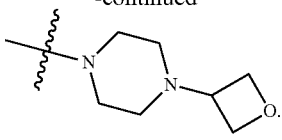

In some embodiments, R¹ is selected from the group consisting of

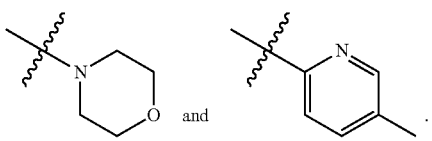

and.

In some embodiments, ring A is a 5-membered heteroaryl that is optionally substituted with $R^d$.

In some embodiments, ring A is a 6-membered heteroaryl that is optionally substituted with $R^d$.

In some embodiments, ring A is a 9-membered bicyclic heteroaryl that comprises at least two heteroatoms selected form the group consisting of N, O, and S, wherein ring A is optionally substituted with $R^d$.

In some embodiments, each $R^d$ is, independently at each occurrence, halogen; CN; —S(O)$_{1-2}$R$^n$; OH; C$_{1-6}$alkoxy; —NR$^e$R$^f$; C$_{3-10}$cycloalkyl group optionally substituted with OH or halogen; a 3-11 membered saturated or partially saturated heterocyclic group optionally substituted with oxo or C$_{1-3}$alkyl; a 5-6 membered monocyclic heteroaryl ring optionally substituted with halogen, oxo, CN, OH, C$_{1-4}$alkoxy, —NR$^e$R$^f$, or C$_{1-4}$alkyl optionally substituted with halogen, or OH; or C$_{1-4}$alkyl optionally substituted with halogen, or OH.

In some embodiments, each $R^d$ is, independently at each occurrence, halogen; CN; —S(O)$_{1-2}$R$^n$; OH; C$_{1-6}$alkoxy; —NR$^e$R$^f$; C$_{3-10}$cycloalkyl group optionally substituted with OH or halogen; a 3-11 membered saturated or partially saturated heterocyclic group optionally substituted with oxo or C$_{1-3}$alkyl; a 5-6 membered monocyclic heteroaryl ring optionally substituted with halogen, oxo, CN, OH, C$_{1-4}$alkoxy, —NR$^e$R$^f$, or C$_{1-4}$alkyl optionally substituted with halogen, or OH; or C$_{1-4}$alkyl optionally substituted with halogen, or OH.

In some embodiments, each $R^d$ is, independently at each occurrence, oxo, OH, amino, CN, fluoro, chloro, bromo, methyl, ethyl, tert-butyl, 2-hydroxyethyl, methylsulfonyl, hydroxymethyl, trifluoromethyl,

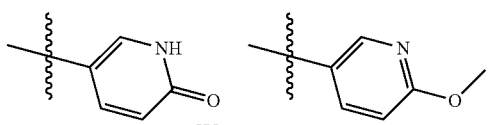

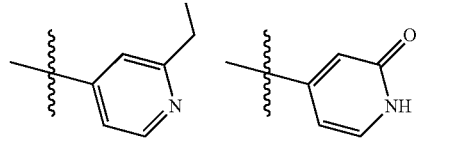

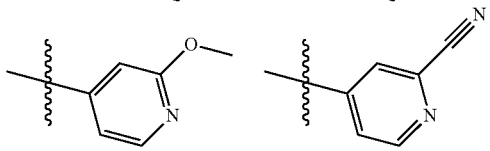

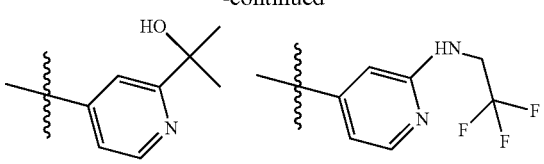

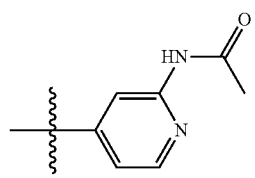

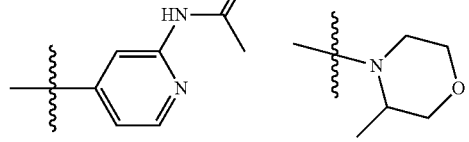

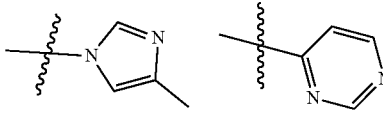

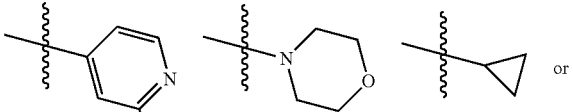

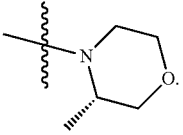

In some embodiments, ring A is selected from the group consisting of

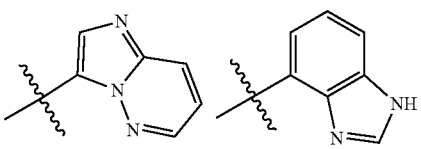

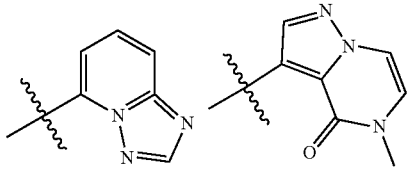

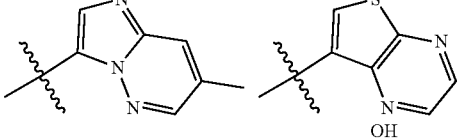

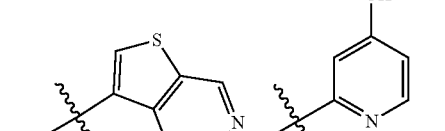

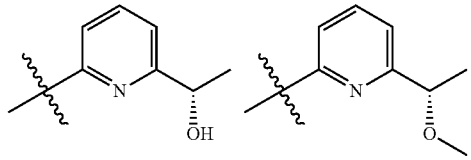

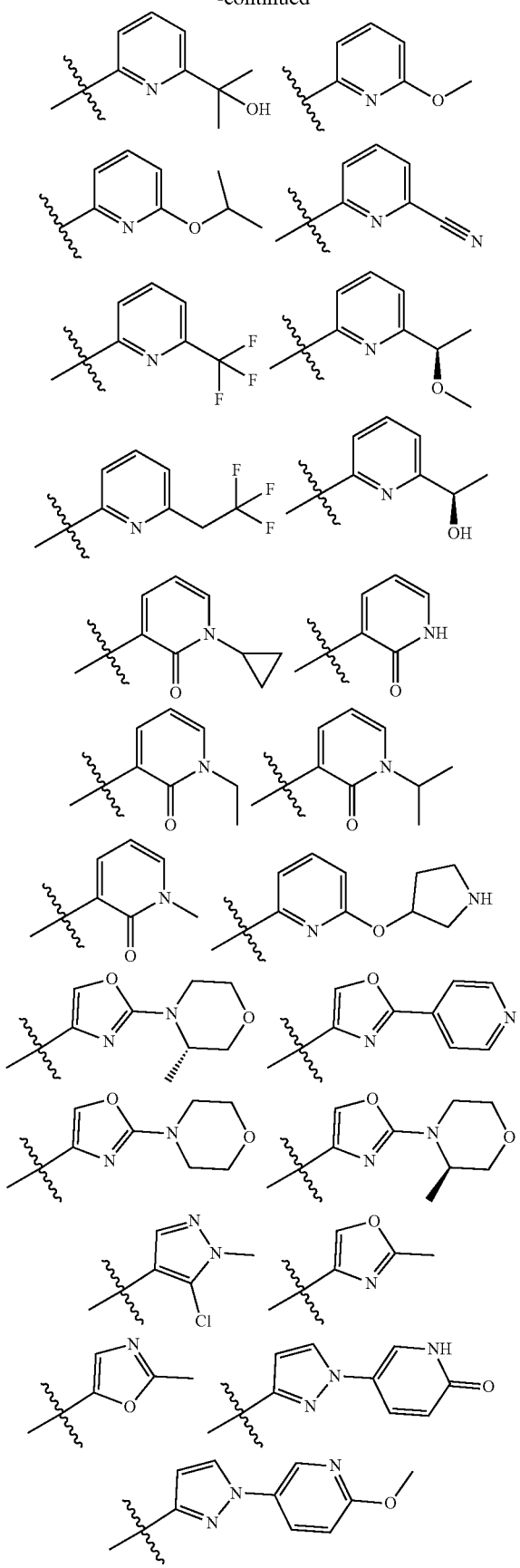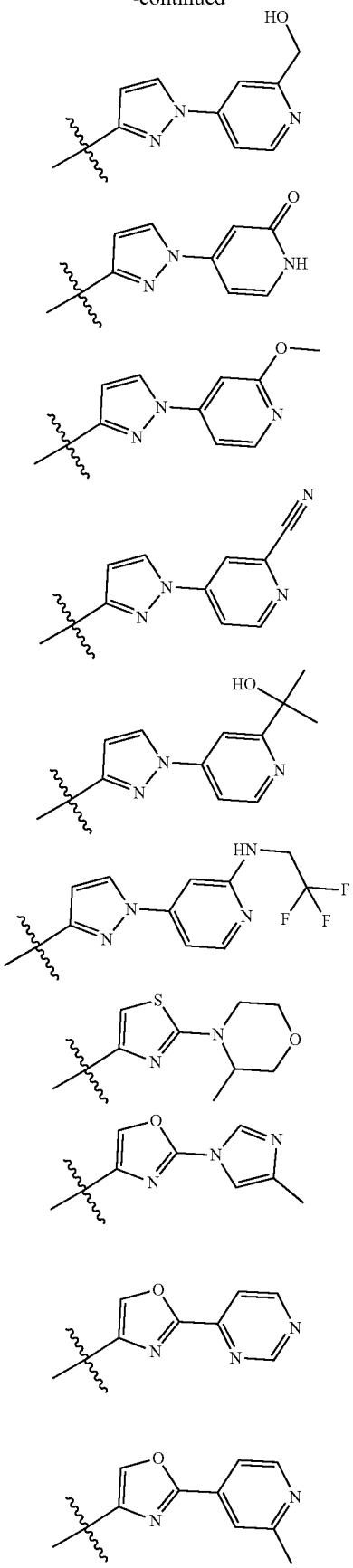

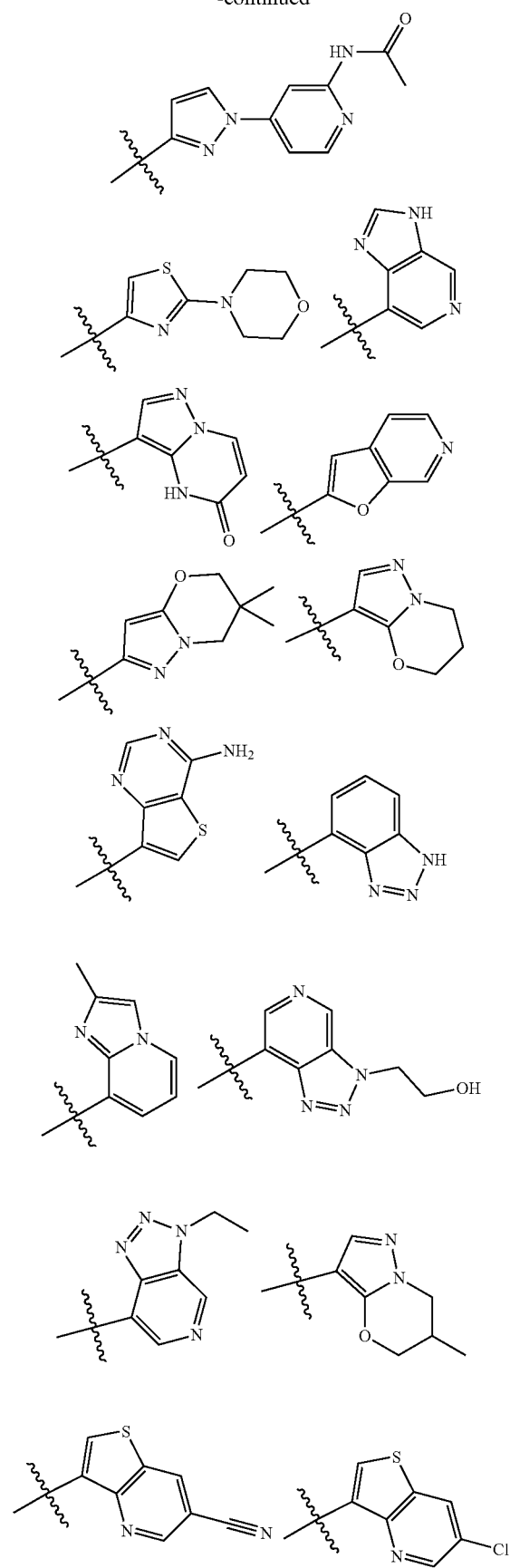
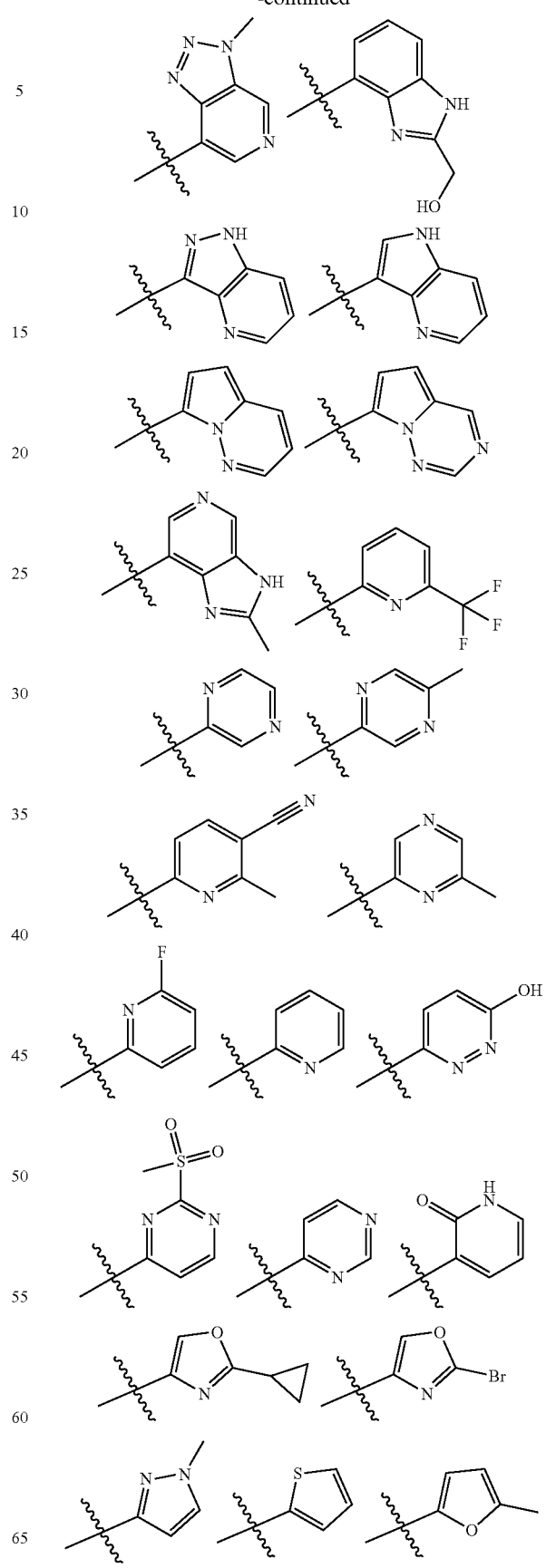

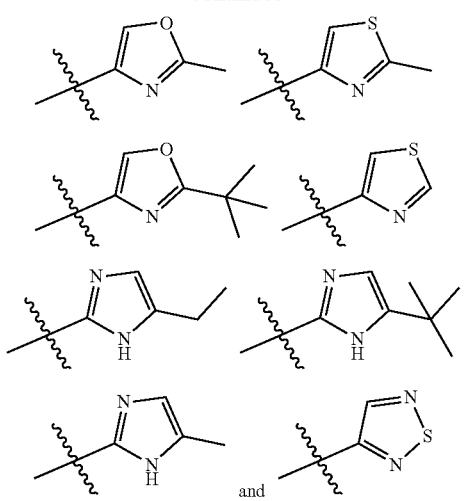
In some embodiments, ring A is selected from the group consisting of
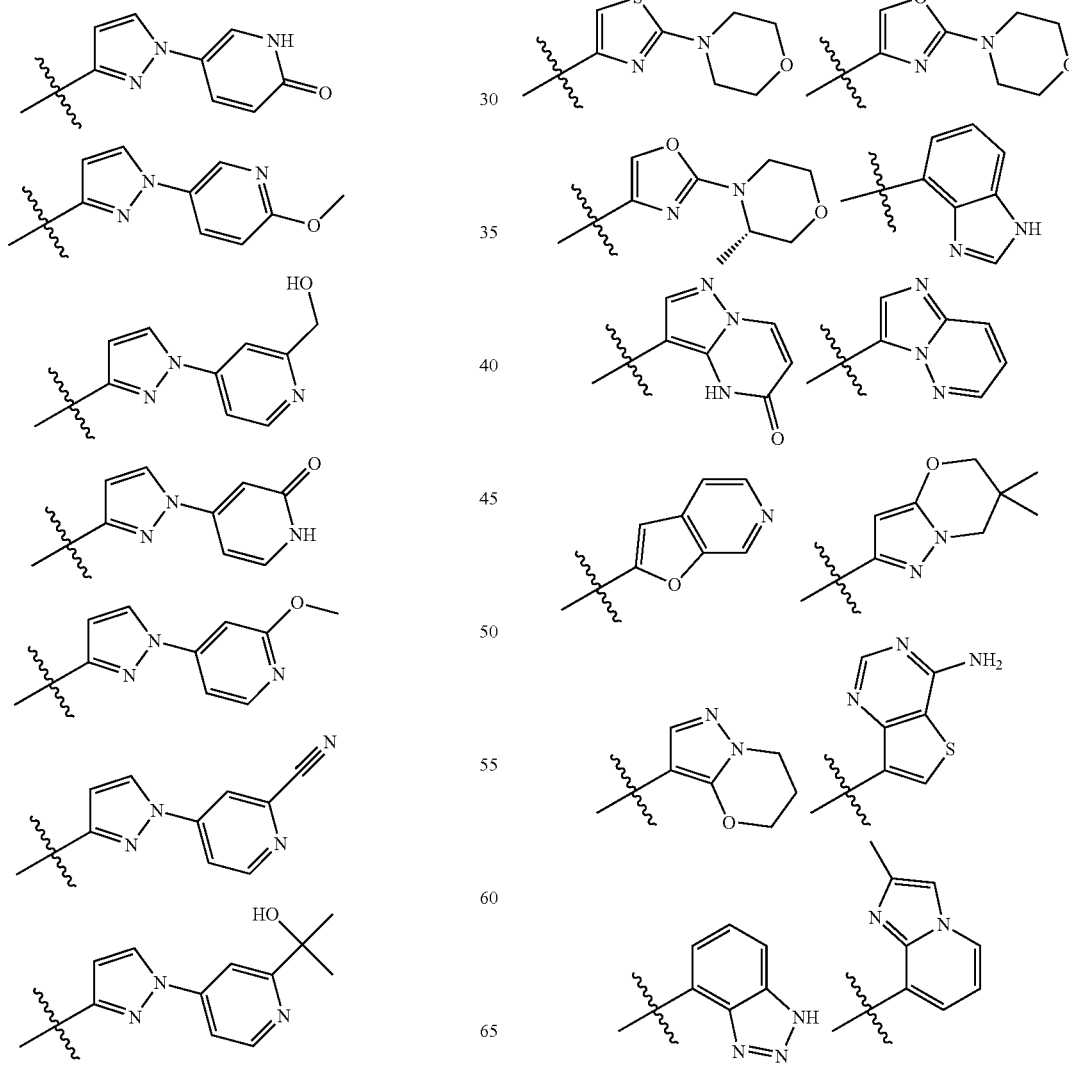
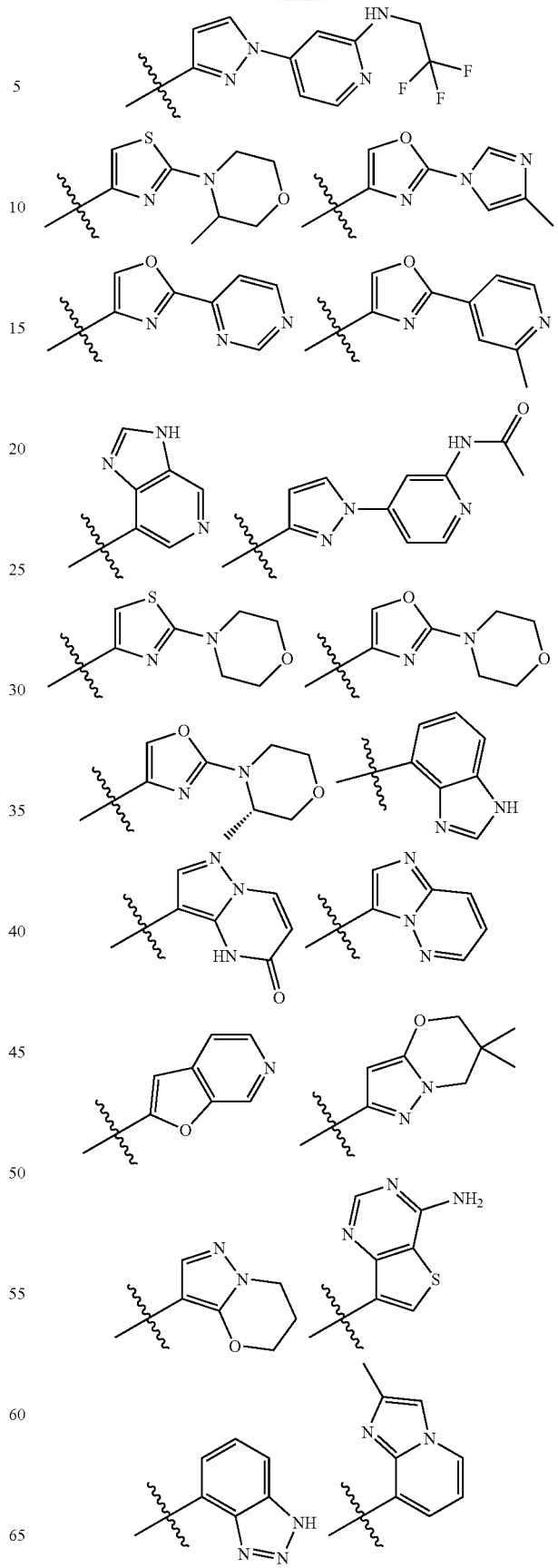

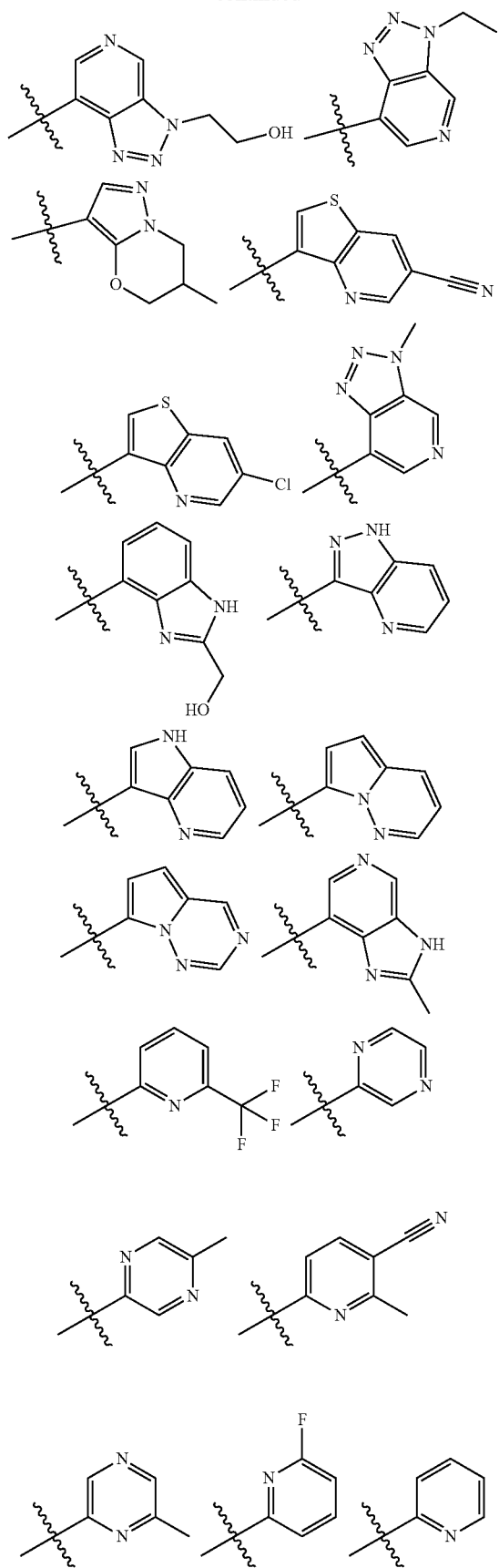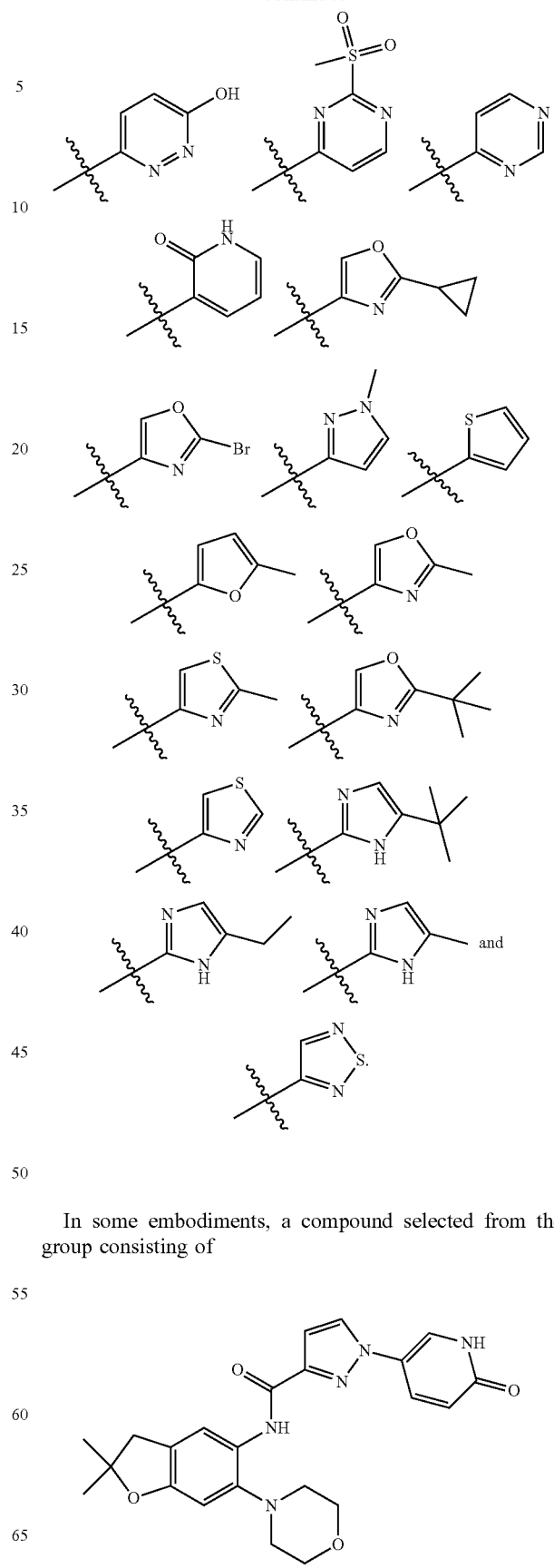
In some embodiments, a compound selected from the group consisting of
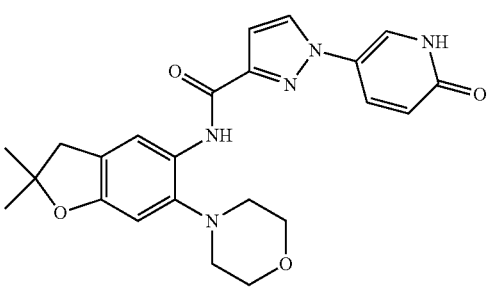

31
-continued
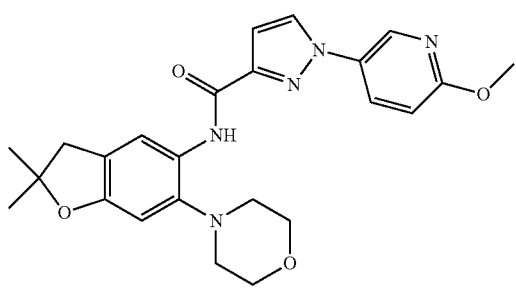
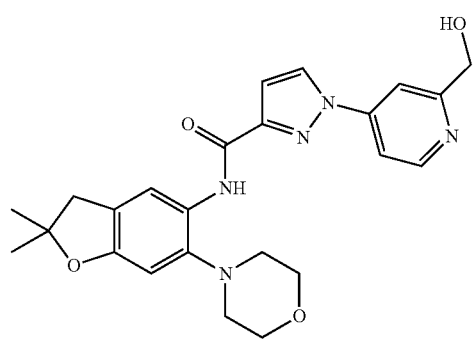
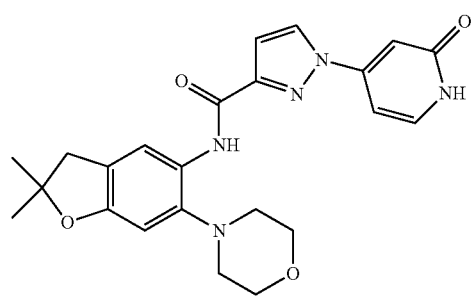
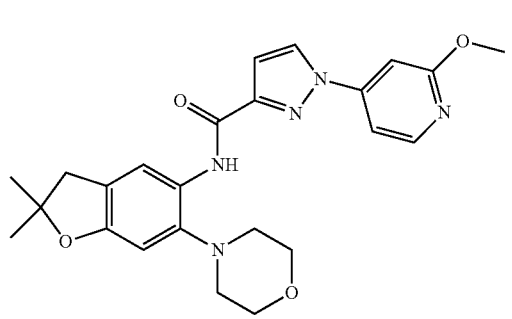
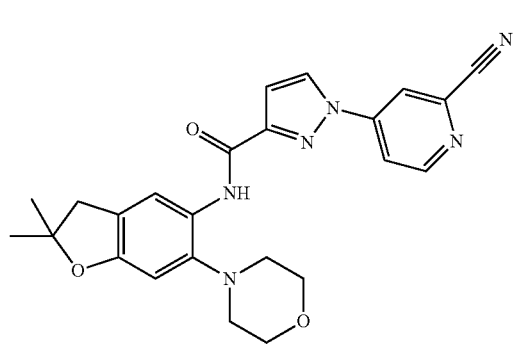
32
-continued
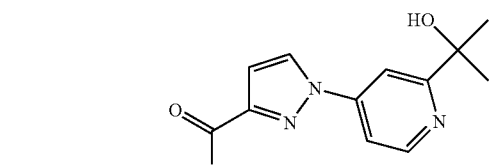
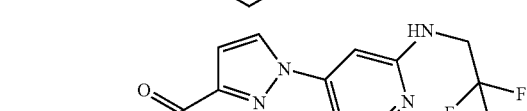
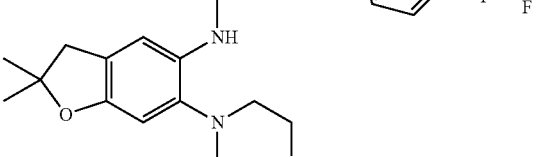
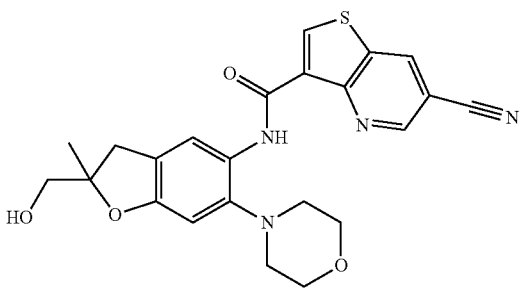
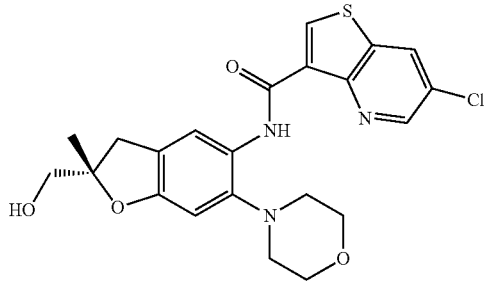
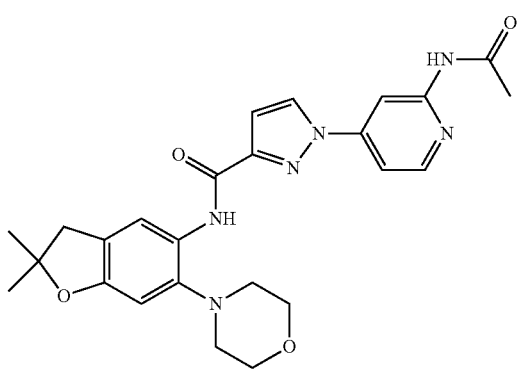

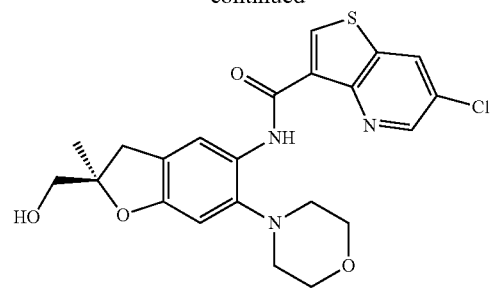
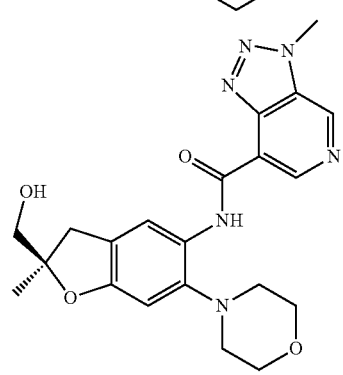
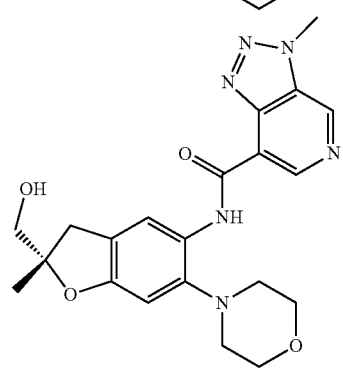
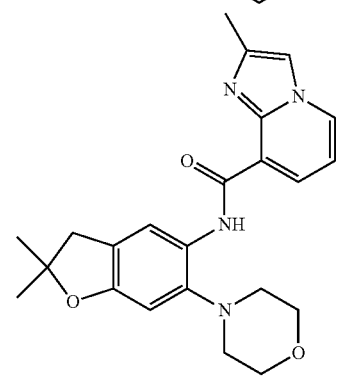
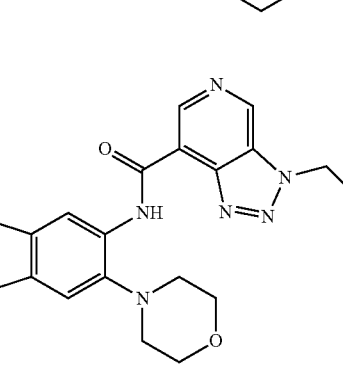
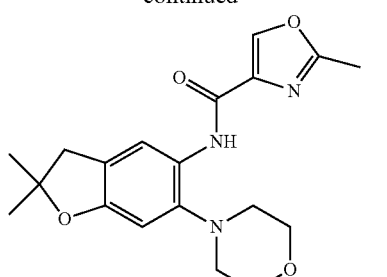
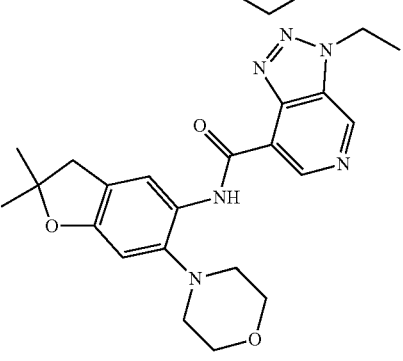
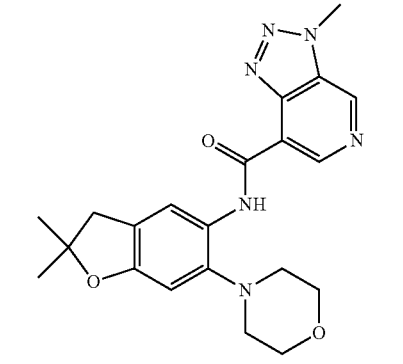
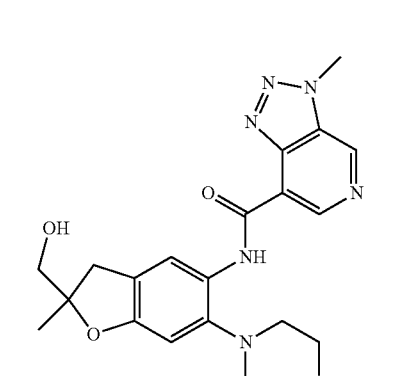
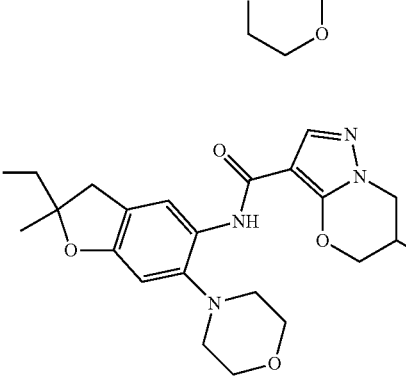

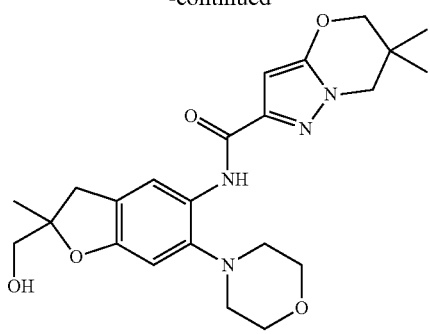
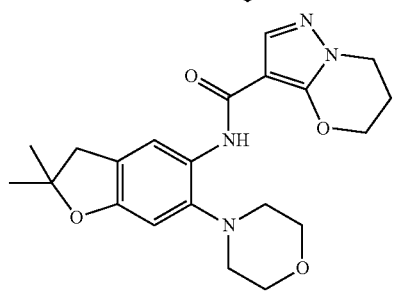
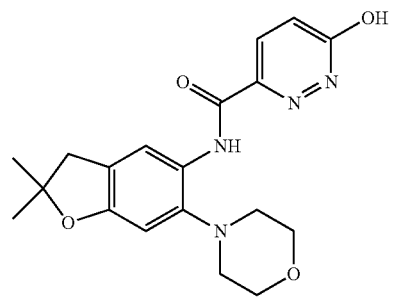
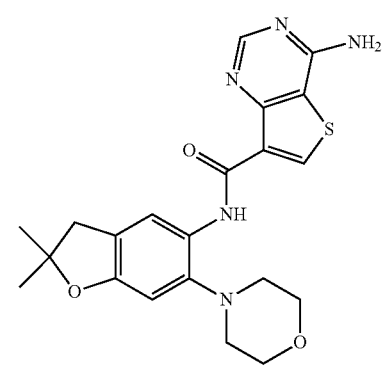
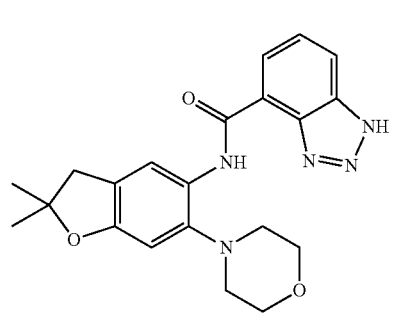
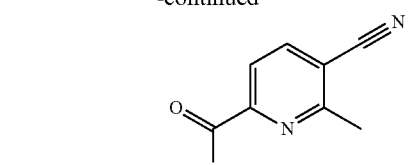
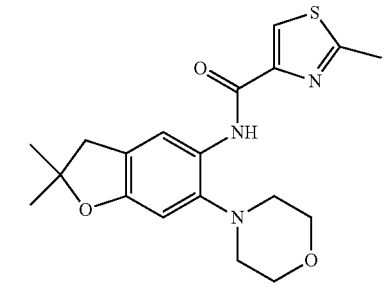
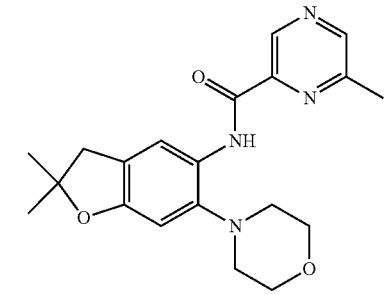
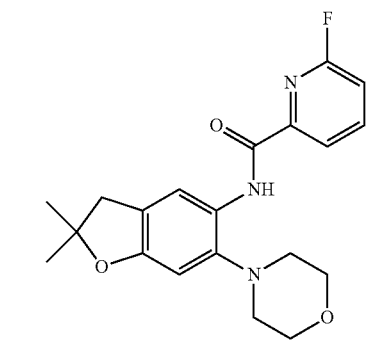
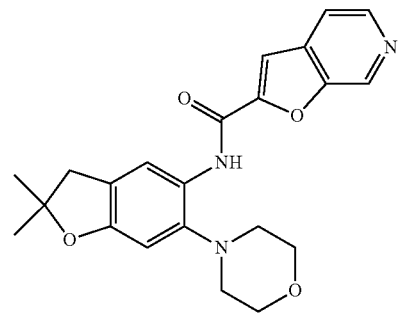

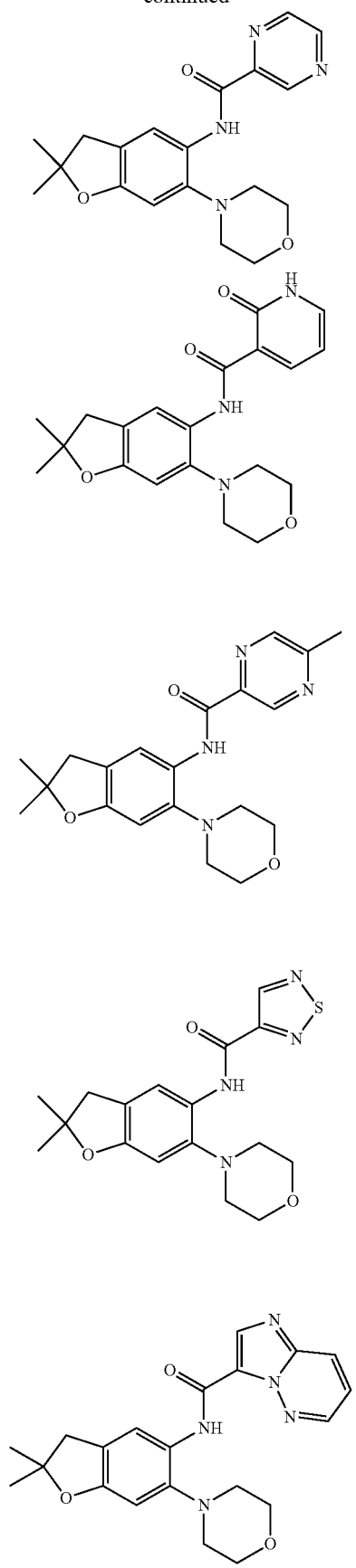
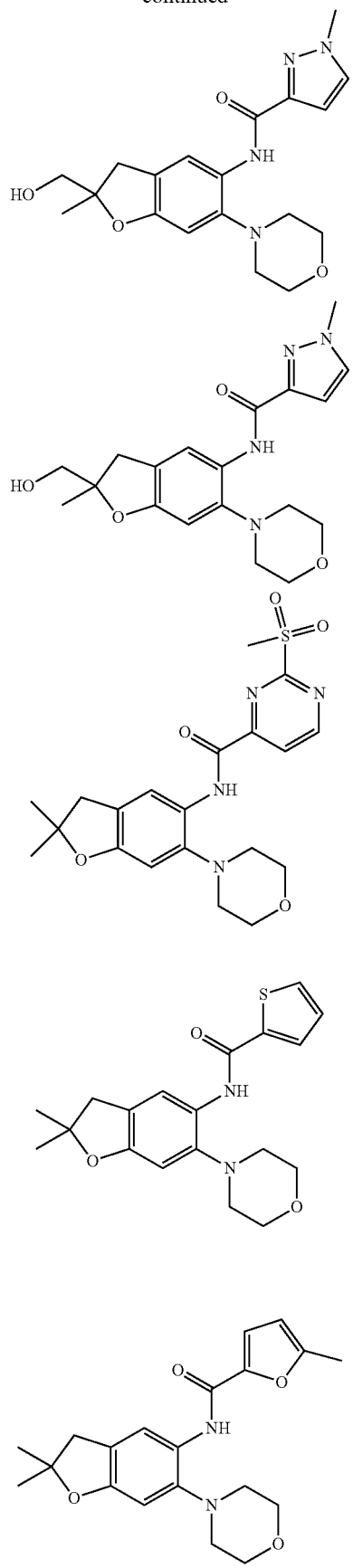

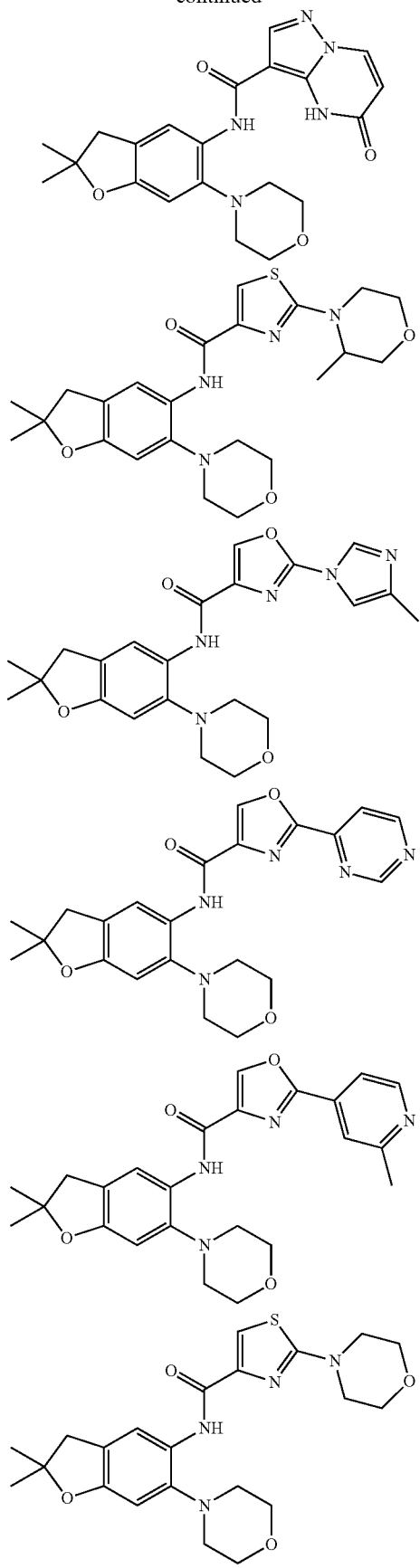
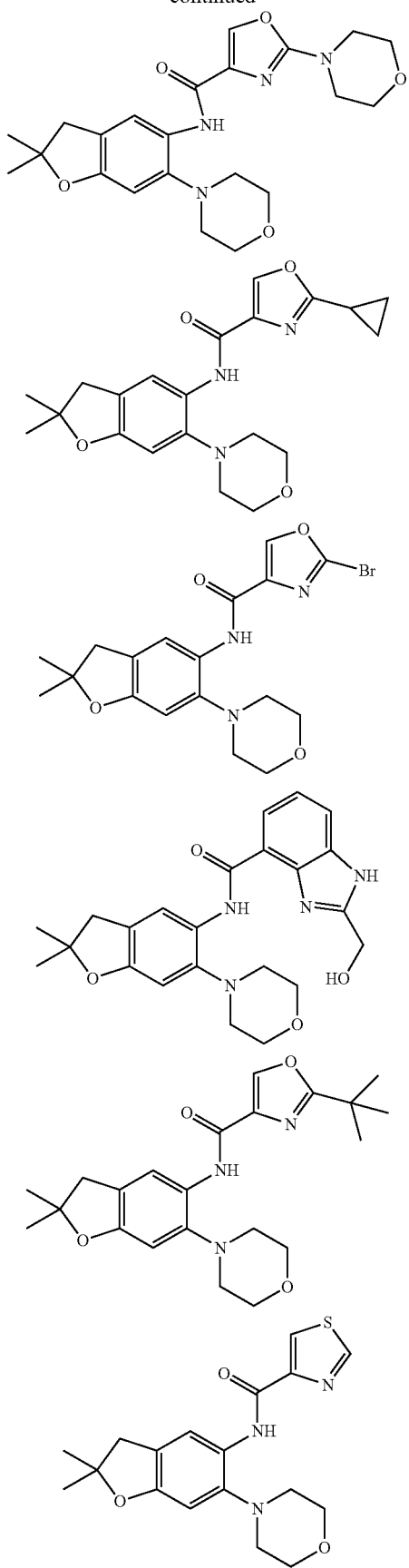

-continued
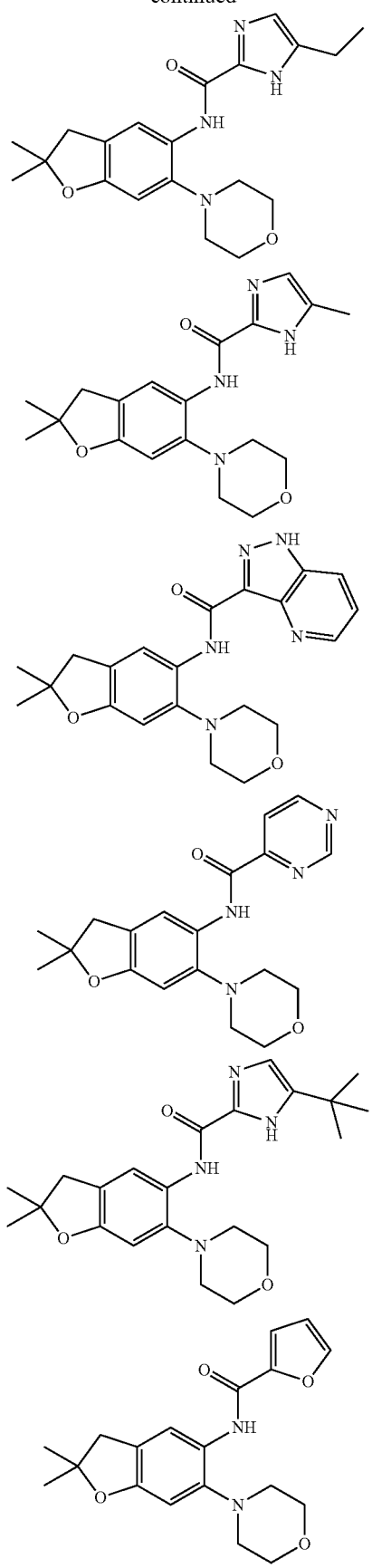
-continued
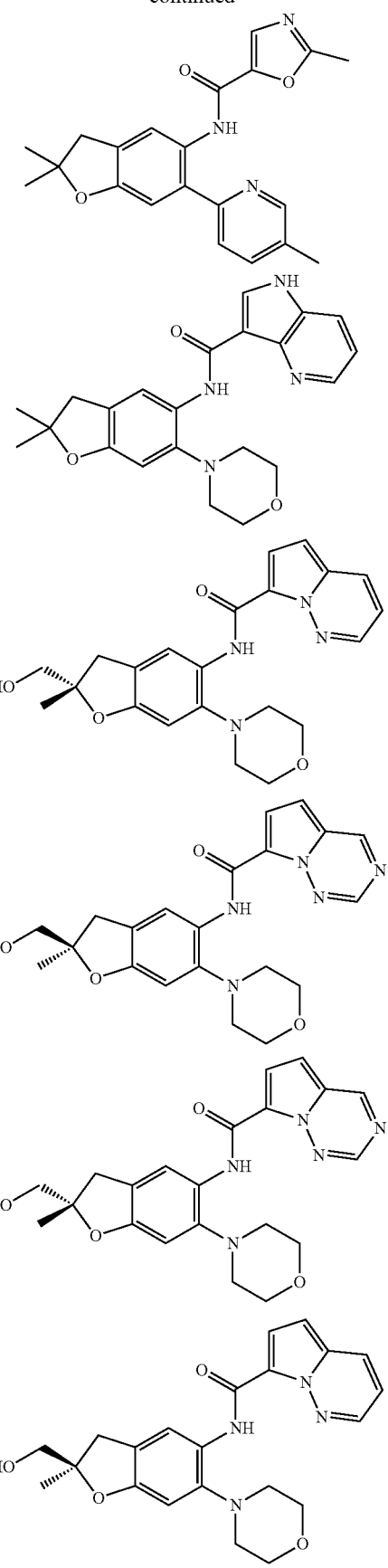

-continued

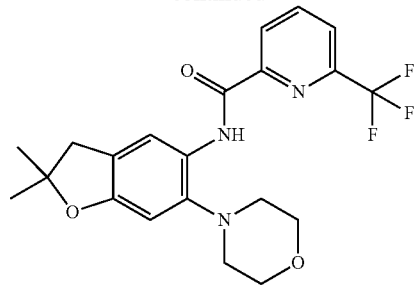

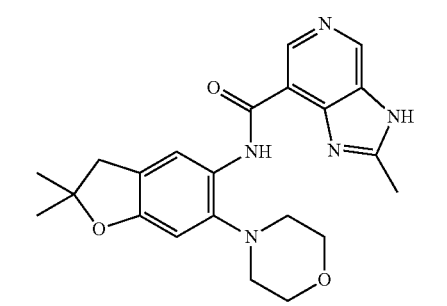

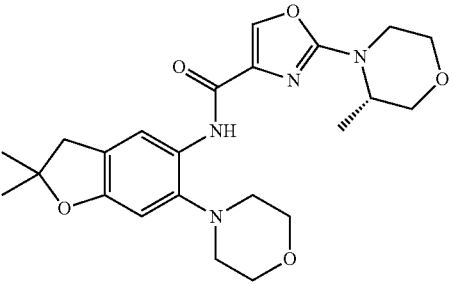

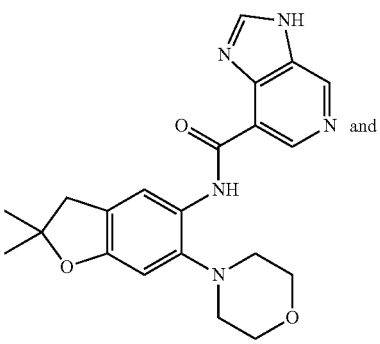

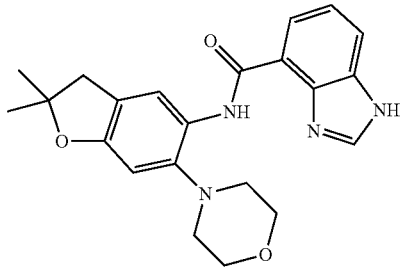

and or a stereoisomer or pharmaceutically acceptable salt thereof is provided.

In some embodiments, the compound, stereoisomer, or pharmaceutically acceptable salt is selected from the compounds shown in Table 1 below, and from stereoisomers and pharmaceutically acceptable salts thereof.

TABLE 1

Exemplary compounds of the present invention. Salts of such compounds are also contemplated. See the Examples section for preparation of such compounds.

| # | Structure | Name |
|---|-----------|------|
| 1 | 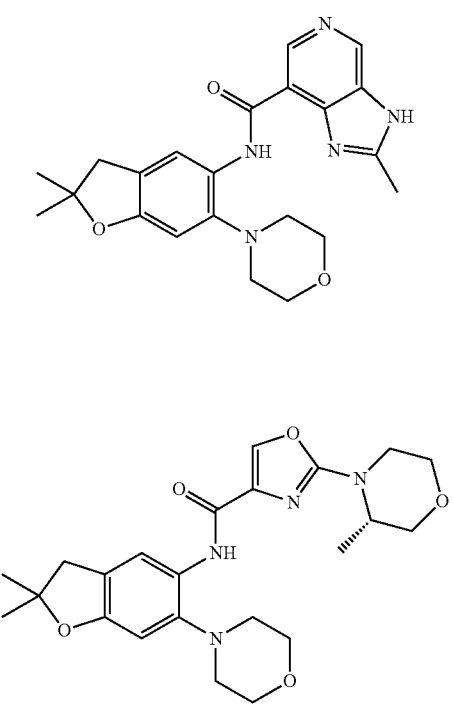 | N-(2,2-dimethyl-6-morpholino-3H-benzofuran-5-yl)-6,7-dihydro-5H-pyrazolo[5,1-b][1,3]oxazine-3-carboxamide |

TABLE 1-continued

Exemplary compounds of the present invention. Salts of such compounds are also contemplated. See the Examples section for preparation of such compounds.

| # | Structure | Name |
|---|---|---|
| 2 | 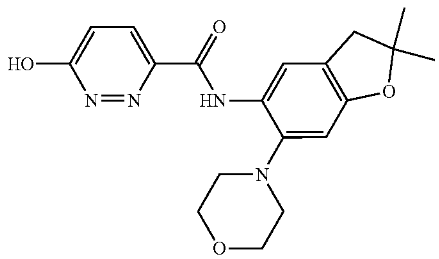 [SMILES: CC1(C)Cc2cc(NC(=O)c3ccc(O)nn3)c(N3CCOCC3)cc2O1] | N-(2,2-dimethyl-6-morpholino-3H-benzofuran-5-yl)-6-hydroxy-pyridazine-3-carboxamide |
| 3 | 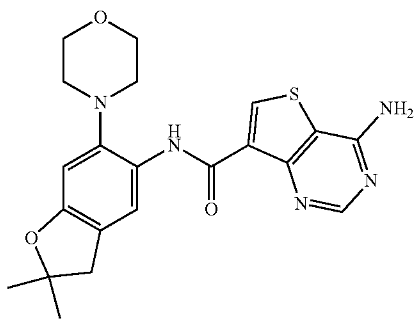 [SMILES: CC1(C)Cc2cc(NC(=O)c3csc4c(N)ncnc34)c(N3CCOCC3)cc2O1] | 4-amino-N-(2,2-dimethyl-6-morpholino-3H-benzofuran-5-yl)thieno[3,2-d]pyramine-7-carboxamide |
| 4 | 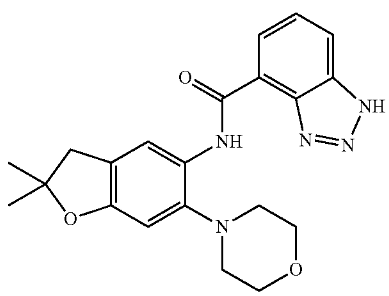 [SMILES: CC1(C)Cc2cc(NC(=O)c3cccc4[nH]nnc34)c(N3CCOCC3)cc2O1] | N-(2,2-dimethyl-6-morpholino-3H-benzofuran-5-yl)-1H-benzotriazole-4-carboxamide |
| 5 | 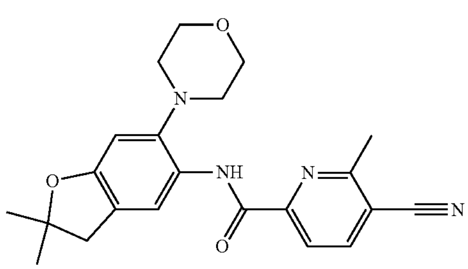 [SMILES: Cc1nc(C(=O)Nc2cc3c(cc2N2CCOCC2)OC(C)(C)C3)ccc1C#N] | 5-cyano-N-(2,2-dimethyl-6-morpholino-3H-benzofuran-5-yl)-6-methyl-pyridine-2-carboxamide |
| 6 | 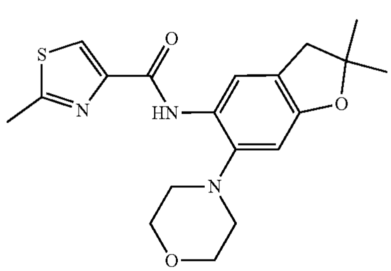 | N-(2,2-dimethyl-6-morpholino-3H-benzofuran-5-yl)-2-methyl-thiazole-4-carboxamide |

TABLE 1-continued

Exemplary compounds of the present invention. Salts of such compounds are also contemplated. See the Examples section for preparation of such compounds.

| # | Structure | Name |
|---|---|---|
| 7 | 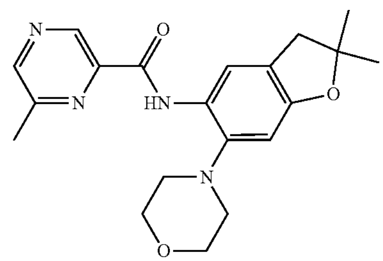 | N-(2,2-dimethyl-6-morpholino-3H-benzofuran-5-yl)-6-methyl-pyrazine-2-carboxamide |
| 8 | 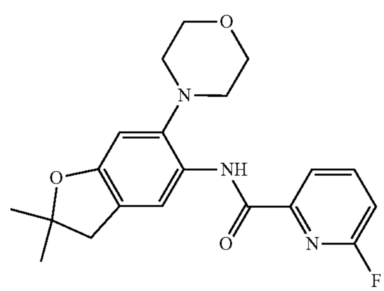 [SMILES: CC1(C)Cc2cc(NC(=O)c3cccc(F)n3)c(N3CCOCC3)cc2O1] | N-(2,2-dimethyl-6-morpholino-3H-benzofuran-5-yl)-6-fluoro-pyridine-2-carboxamide |
| 9 | 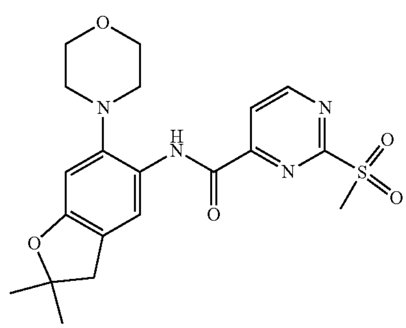 [SMILES: CC1(C)Cc2cc(NC(=O)c3ccnc(S(C)(=O)=O)n3)c(N3CCOCC3)cc2O1] | N-(2,2-dimethyl-6-morpholino-3H-benzofuran-5-yl)-2-methylsulfonyl-pyrimidine-4-carboxamide |
| 10 | 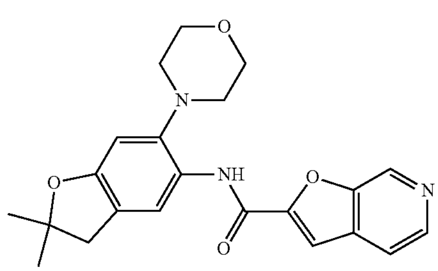 [SMILES: CC1(C)Cc2cc(NC(=O)c3cc4ccncc4o3)c(N3CCOCC3)cc2O1] | N-(2,2-dimethyl-6-morpholino-3H-benzofuran-5-yl)furo[2,3-c]pyridine-2-carboxamide |
| 11 | 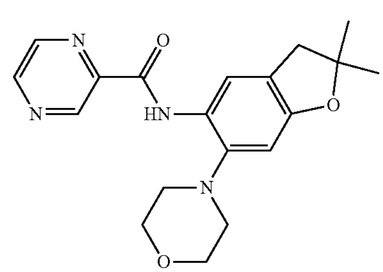 [SMILES: CC1(C)Cc2cc(NC(=O)c3cnccn3)c(N3CCOCC3)cc2O1] | N-(2,2-dimethyl-6-morpholino-3H-benzofuran-5-yl)pyrazine-2-carboxamide |

TABLE 1-continued

Exemplary compounds of the present invention. Salts of such compounds are also contemplated. See the Examples section for preparation of such compounds.

| # | Structure | Name |
|---|-----------|------|
| 12 | 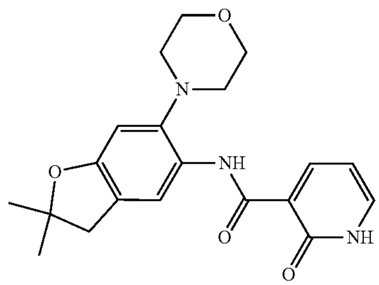 [SMILES: CC1(C)Cc2cc(NC(=O)c3ccc[nH]c3=O)c(N3CCOCC3)cc2O1] | N-(2,2-dimethyl-6-morpholino-3H-benzofuran-5-yl)-2-oxo-1H-pyridine-3-carboxamide |
| 13 | 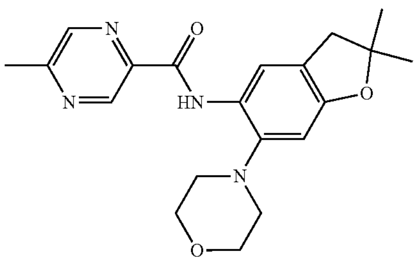 | N-(2,2-dimethyl-6-morpholino-3H-benzofuran-5-yl)-5-methyl-pyrazine-2-carboxamide |
| 14 | 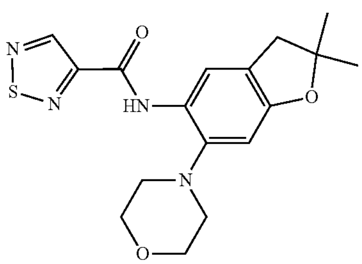 [SMILES: CC1(C)Cc2cc(NC(=O)c3cnsn3)c(N3CCOCC3)cc2O1] | N-(2,2-dimethyl-6-morpholino-3H-benzofuran-5-yl)-1,2,5-thiadiazole-3-carboxamide |
| 15 | 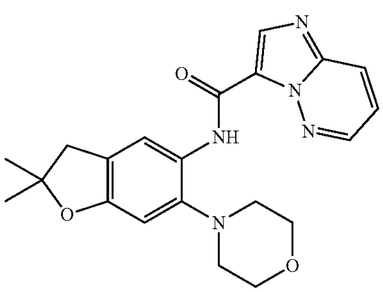 [SMILES: CC1(C)Cc2cc(NC(=O)c3cnc4cccnn34)c(N3CCOCC3)cc2O1] | N-(2,2-dimethyl-6-morpholino-3H-benzofuran-5-yl)imidazo[1,2-b]pyridazine-3-carboxamide |
| 16 | 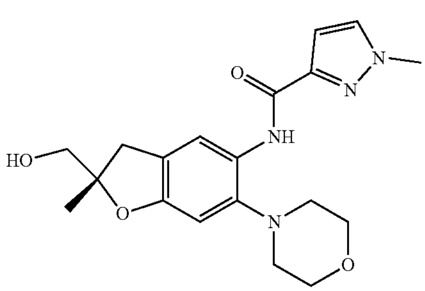 [SMILES: Cn1ccc(C(=O)Nc2cc3c(cc2N2CCOCC2)O[C@](C)(CO)C3)n1] | N-[rac-(2S)-2-(hydroxymethyl)-2-methyl-6-morpholino-3H-benzofuran-5-yl]-1-methyl-pyrazole-3-carboxamide |

TABLE 1-continued

Exemplary compounds of the present invention. Salts of such compounds are also contemplated. See the Examples section for preparation of such compounds.

| # | Structure | Name |
|---|-----------|------|
| 17 | 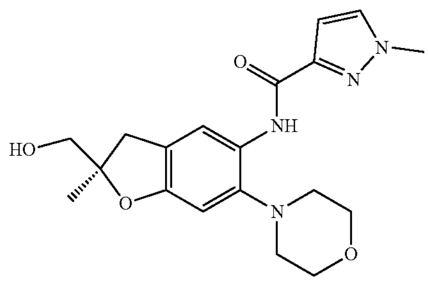 [SMILES: Cn1ccc(C(=O)Nc2cc3c(cc2N2CCOCC2)O[C@@](C)(CO)C3)n1] | N-[rac-(2R)-2-(hydroxymethyl)-2-methyl-6-morpholino-3H-benzofuran-5-yl]-1-methyl-pyrazole-3-carboxamide |
| 18 | 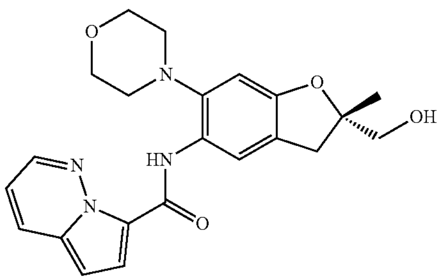 [SMILES: C[C@@]1(CO)Cc2cc(NC(=O)c3ccc4cccnn34)c(N3CCOCC3)cc2O1] | N-[rac-(2S)-2-(hydroxymethyl)-2-methyl-6-morpholino-3H-benzofuran-5-yl]pyrrolo[1,2-b]pyridazine-7-carboxamide |
| 19 | 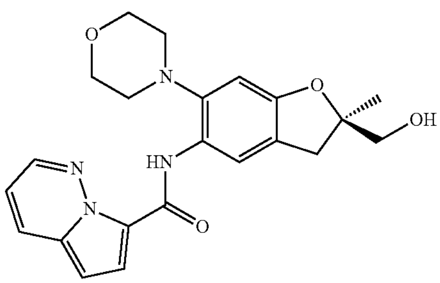 [SMILES: C[C@]1(CO)Cc2cc(NC(=O)c3ccc4cccnn34)c(N3CCOCC3)cc2O1] | N-[rac-(2R)-2-(hydroxymethyl)-2-methyl-6-morpholino-3H-benzofuran-5-yl]pyrrolo[1,2-b]pyridazine-7-carboxamide |
| 20 | 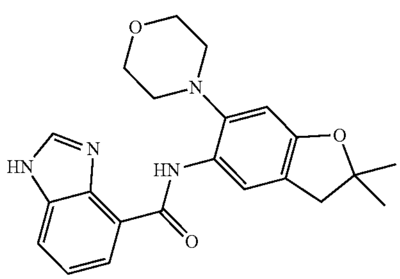 [SMILES: CC1(C)Cc2cc(NC(=O)c3cccc4[nH]cnc34)c(N3CCOCC3)cc2O1] | N-(2,2-dimethyl-6-morpholino-3H-benzofuran-5-yl)-1H-benzimidazole-4-carboxamide |
| 21 | 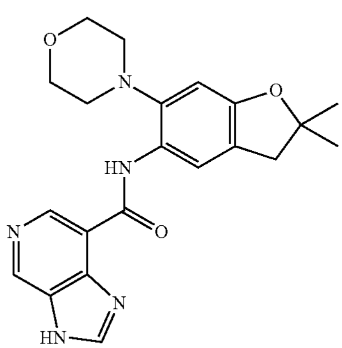 [SMILES: CC1(C)Cc2cc(NC(=O)c3cncc4[nH]cnc34)c(N3CCOCC3)cc2O1] | N-(2,2-dimethyl-6-morpholino-3H-benzofuran-5-yl)-3H-imidazo[4,5-c]pyridine-7-carboxamide |

TABLE 1-continued

Exemplary compounds of the present invention. Salts of such compounds are also contemplated. See the Examples section for preparation of such compounds.

| # | Structure | Name |
|---|---|---|
| 22 | 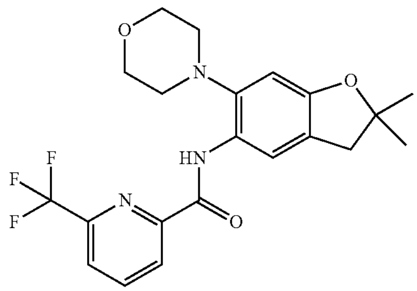 [SMILES: CC1(C)Cc2cc(NC(=O)c3cccc(C(F)(F)F)n3)c(N3CCOCC3)cc2O1] | N-(2,2-dimethyl-6-morpholino-3H-benzofuran-5-yl)-6-(trifluoromethyl)pyridine-2-carboxamide |
| 23 | 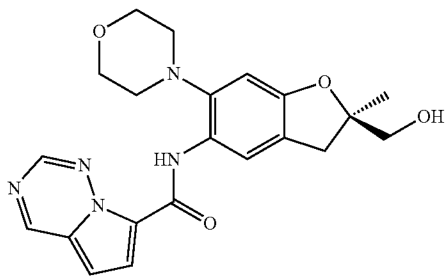 [SMILES: C[C@]1(CO)Cc2cc(NC(=O)c3ccc4cncnn34)c(N3CCOCC3)cc2O1] | N-[rac-(2R)-2-(hydroxymethyl)-2-methyl-6-morpholino-3H-benzofuran-5-yl]pyrrolo[2,1-f][1,2,4]triazine-7-carboxamide |
| 24 | 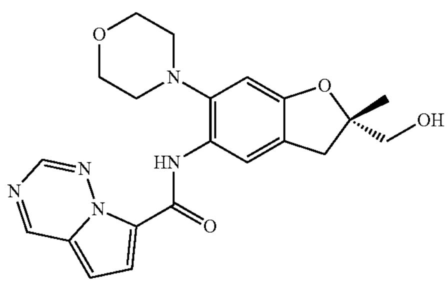 [SMILES: C[C@@]1(CO)Cc2cc(NC(=O)c3ccc4cncnn34)c(N3CCOCC3)cc2O1] | N-[rac-(2S)-2-(hydroxymethyl)-2-methyl-6-morpholino-3H-benzofuran-5-yl]pyrrolo[2,1-f][1,2,4]triazine-7-carboxamide |
| 25 | 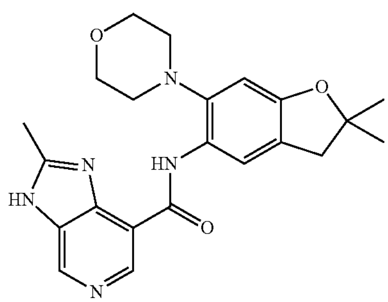 | N-(2,2-dimethyl-6-morpholino-3H-benzofuran-5-yl)-2-methyl-3H-imidazo[4,5-c]pyridine-7-carboxamide |
| 26 | 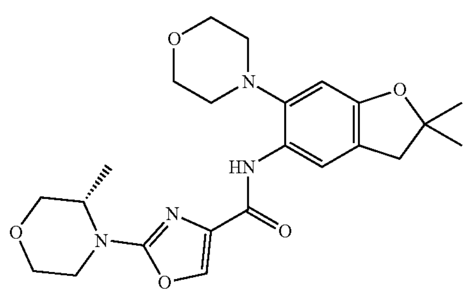 [SMILES: C[C@H]1COCCN1c1nc(C(=O)Nc2cc3c(cc2N2CCOCC2)OC(C)(C)C3)co1] | N-(2,2-dimethyl-6-morpholino-3H-benzofuran-5-yl)-2-[rac-(3S)-3-methylmorpholin-4-yl]oxazole-4-carboxamide |

TABLE 1-continued

Exemplary compounds of the present invention. Salts of such compounds are also contemplated. See the Examples section for preparation of such compounds.

| # | Structure | Name |
|---|-----------|------|
| 27 | 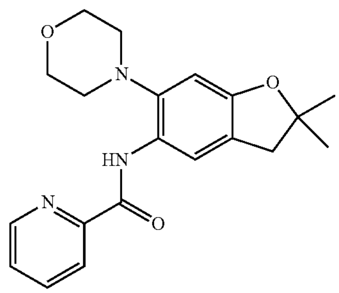 [SMILES: CC1(C)Cc2cc(NC(=O)c3ccccn3)c(N3CCOCC3)cc2O1] | N-(2,2-dimethyl-6-morpholino-3H-benzofuran-5-yl)pyridine-2-carboxamide |
| 28 | 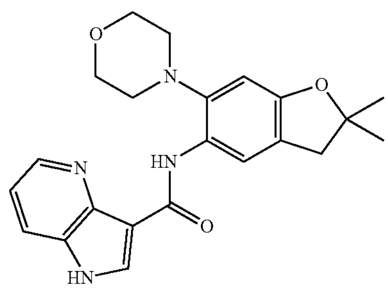 [SMILES: CC1(C)Cc2cc(NC(=O)c3c[nH]c4cccnc34)c(N3CCOCC3)cc2O1] | N-(2,2-dimethyl-6-morpholino-3H-benzofuran-5-yl)-1H-pyrrolo[3,2-b]pyridine-3-carboxamide |
| 29 | 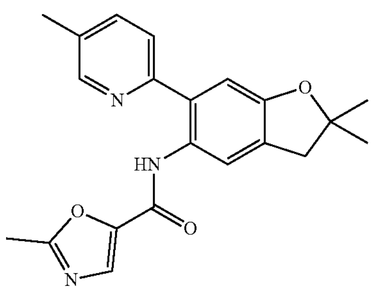 | N-[2,2-dimethyl-6-(5-methyl-2-pyridyl)-3H-benzofuran-5-yl]-2-methyl-oxazole-5-carboxamide |
| 30 | 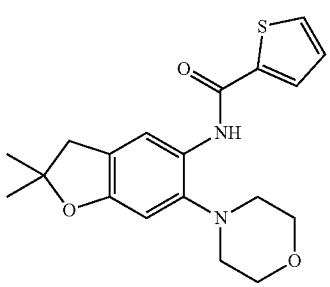 [SMILES: CC1(C)Cc2cc(NC(=O)c3cccs3)c(N3CCOCC3)cc2O1] | N-(2,2-dimethyl-6-morpholino-3H-benzofuran-5-yl)thiophene-2-carboxamide |
| 31 | 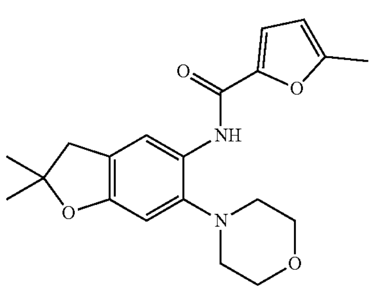 | N-(2,2-dimethyl-6-morpholino-3H-benzofuran-5-yl)-5-methyl-furan-2-carboxamide |

TABLE 1-continued

Exemplary compounds of the present invention. Salts of such compounds are also contemplated. See the Examples section for preparation of such compounds.

| # | Structure | Name |
|---|---|---|
| 32 | 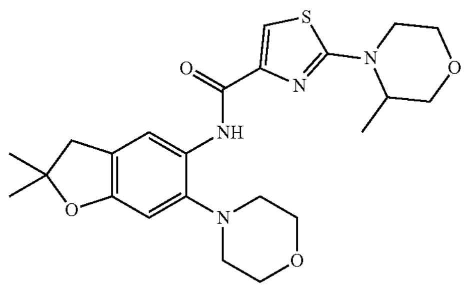 [SMILES: CC1COCCN1c1nc(C(=O)Nc2cc3c(cc2N2CCOCC2)OC(C)(C)C3)cs1] | N-(2,2-dimethyl-6-morpholino-3H-benzofuran-5-yl)-2-(3-methylmorpholin-4-yl)thiazole-4-carboxamide |
| 33 | 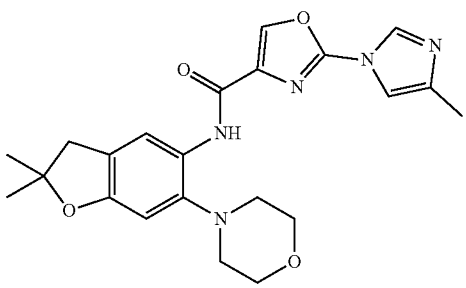 | N-(2,2-dimethyl-6-morpholino-3H-benzofuran-5-yl)-2-(4-methylimidazol-1-yl)oxazole-4-carboxamide |
| 34 | 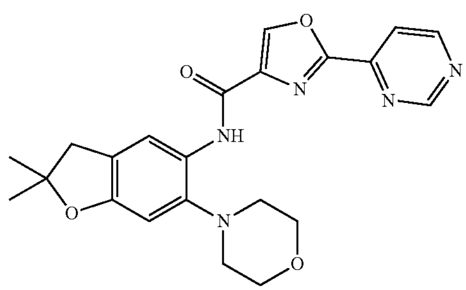 [SMILES: CC1(C)Cc2cc(NC(=O)c3coc(-c4ccncn4)n3)c(N3CCOCC3)cc2O1] | N-(2,2-dimethyl-6-morpholino-3H-benzofuran-5-yl)-2-pyrimidin-4-yl-oxazole-4-carboxamide |
| 35 | 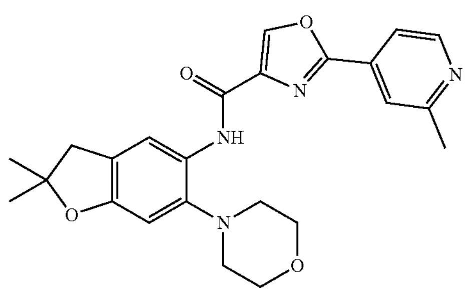 [SMILES: Cc1cc(-c2nc(C(=O)Nc3cc4c(cc3N3CCOCC3)OC(C)(C)C4)co2)ccn1] | N-(2,2-dimethyl-6-morpholino-3H-benzofuran-5-yl)-2-(2-methyl-4-pyridyl)oxazole-4-carboxamide |
| 36 | 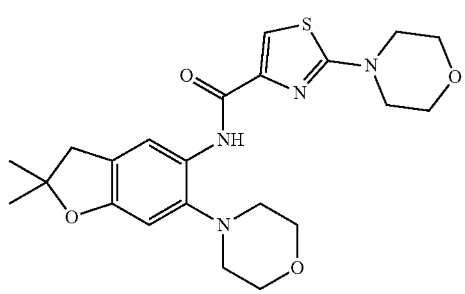 | N-(2,2-dimethyl-6-morpholino-3H-benzofuran-5-yl)-2-morpholino-thiazole-4-carboxamide |

TABLE 1-continued

Exemplary compounds of the present invention. Salts of such compounds are also contemplated. See the Examples section for preparation of such compounds.

| # | Structure | Name |
|---|-----------|------|
| 37 | 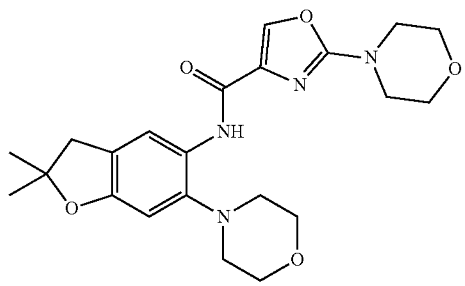 [SMILES: CC1(C)Cc2cc(NC(=O)c3coc(N4CCOCC4)n3)c(N3CCOCC3)cc2O1] | N-(2,2-dimethyl-6-morpholino-3H-benzofuran-5-yl)-2-morpholino-oxazole-4-carboxamide |
| 38 | 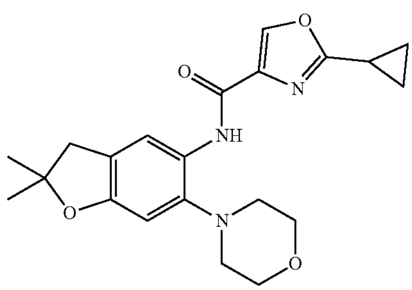 [SMILES: CC1(C)Cc2cc(NC(=O)c3coc(C4CC4)n3)c(N3CCOCC3)cc2O1] | 2-cyclopropyl-N-(2,2-dimethyl-6-morpholino-3H-benzofuran-5-yl)oxazole-4-carboxamide |
| 39 | 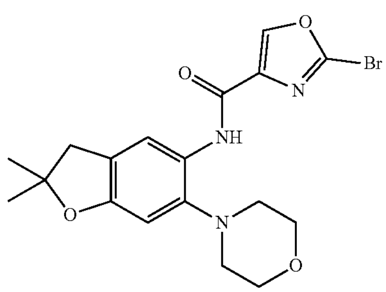 [SMILES: CC1(C)Cc2cc(NC(=O)c3coc(Br)n3)c(N3CCOCC3)cc2O1] | 2-bromo-N-(2,2-dimethyl-6-morpholino-3H-benzofuran-5-yl)oxazole-4-carboxamide |
| 40 | 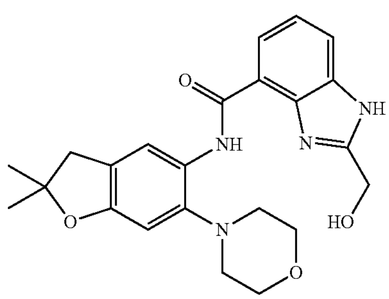 [SMILES: CC1(C)Cc2cc(NC(=O)c3cccc4[nH]c(CO)nc34)c(N3CCOCC3)cc2O1] | N-(2,2-dimethyl-6-morpholino-3H-benzofuran-5-yl)-2-(hydroxymethyl)-1H-benzimidazole-4-carboxamide |
| 41 | 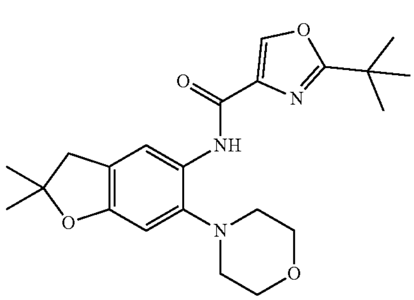 [SMILES: CC1(C)Cc2cc(NC(=O)c3coc(C(C)(C)C)n3)c(N3CCOCC3)cc2O1] | 2-tert-butyl-N-(2,2-dimethyl-6-morpholino-3H-benzofuran-5-yl)oxazole-4-carboxamide |

TABLE 1-continued

Exemplary compounds of the present invention. Salts of such compounds are also contemplated. See the Examples section for preparation of such compounds.

| # | Structure | Name |
|---|-----------|------|
| 42 | 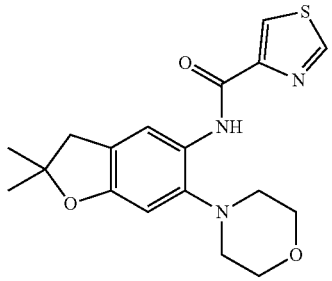 [SMILES: CC1(C)Cc2cc(NC(=O)c3cscn3)c(N3CCOCC3)cc2O1] | N-(2,2-dimethyl-6-morpholino-3H-benzofuran-5-yl)thiazole-4-carboxamide |
| 43 | 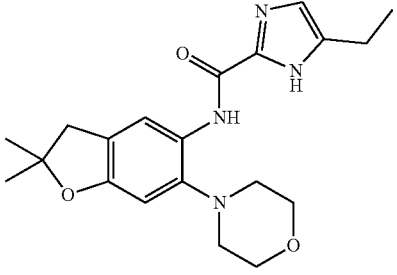 [SMILES: CCc1cnc(C(=O)Nc2cc3c(cc2N2CCOCC2)OC(C)(C)C3)[nH]1] | N-(2,2-dimethyl-6-morpholino-3H-benzofuran-5-yl)-5-ethyl-1H-imidazole-2-carboxamide |
| 44 | 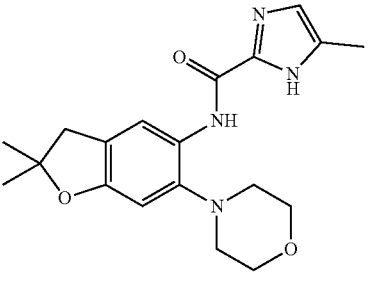 | N-(2,2-dimethyl-6-morpholino-3H-benzofuran-5-yl)-5-methyl-1H-imidazole-2-carboxamide |
| 45 | 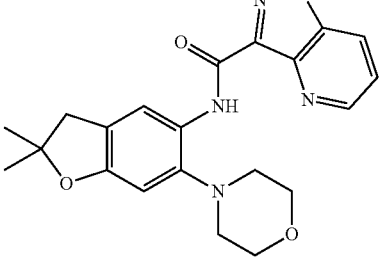 | N-(2,2-dimethyl-6-morpholino-3H-benzofuran-5-yl)-1H-pyrazolo[4,3-b]pyridine-3-carboxamide |
| 46 | 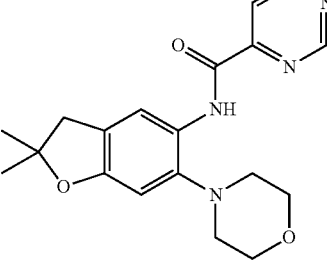 | N-(2,2-dimethyl-6-morpholino-3H-benzofuran-5-yl)pyrimidine-4-carboxamide |

TABLE 1-continued

Exemplary compounds of the present invention. Salts of such compounds are also contemplated. See the Examples section for preparation of such compounds.

| # | Structure | Name |
|---|-----------|------|
| 47 | 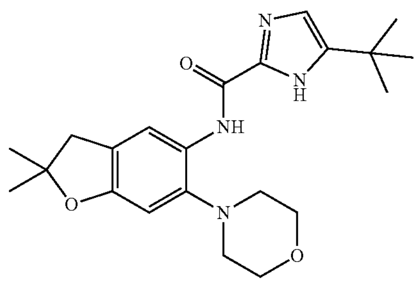 [SMILES: CC1(C)Cc2cc(NC(=O)c3ncc(C(C)(C)C)[nH]3)c(N3CCOCC3)cc2O1] | 5-tert-butyl-N-(2,2-dimethyl-6-morpholino-3H-benzofuran-5-yl)-1H-imidazole-2-carboxamide |
| 48 | 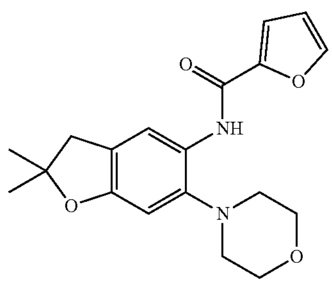 [SMILES: CC1(C)Cc2cc(NC(=O)c3ccco3)c(N3CCOCC3)cc2O1] | N-(2,2-dimethyl-6-morpholino-3H-benzofuran-5-yl)furan-2-carboxamide |
| 49 | 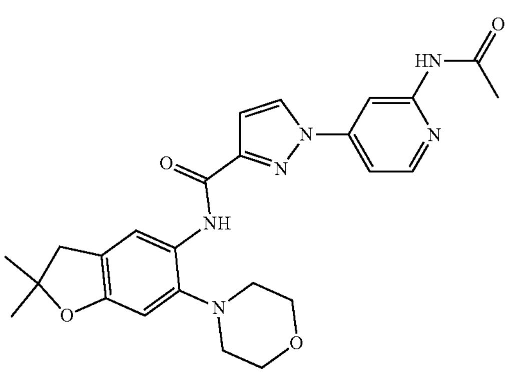 [SMILES: CC(=O)Nc1cc(-n2ccc(C(=O)Nc3cc4c(cc3N3CCOCC3)OC(C)(C)C4)n2)ccn1] | 1-(2-acetamido-4-pyridyl)-N-(2,2-dimethyl-6-morpholino-3H-benzofuran-5-yl)pyrazole-3-carboxamide |
| 50 | 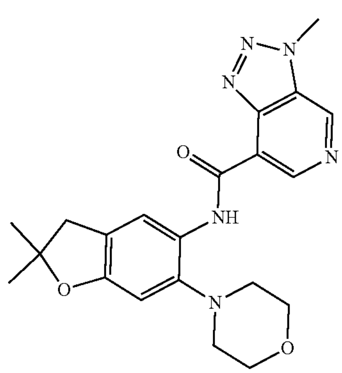 [SMILES: Cn1nnc2c(C(=O)Nc3cc4c(cc3N3CCOCC3)OC(C)(C)C4)cncc21] | N-(2,2-dimethyl-6-morpholino-3H-benzofuran-5-yl)-3-methyl-triazolo[4,5-c]pyridine-7-carboxamide |

TABLE 1-continued

Exemplary compounds of the present invention. Salts of such compounds are also contemplated. See the Examples section for preparation of such compounds.

| # | Structure | Name |
|---|---|---|
| 51 | 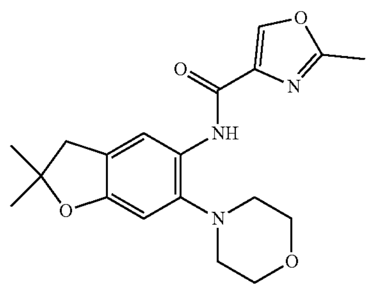 | N-(2,2-dimethyl-6-morpholino-3H-benzofuran-5-yl)-2-methyl-oxazole-4-carboxamide |
| 52 | 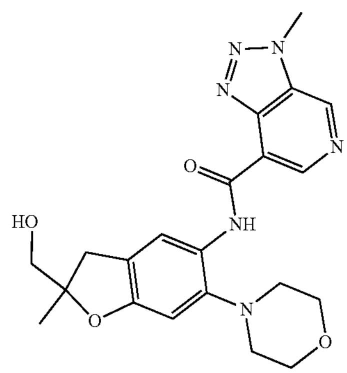 [SMILES: Cn1nnc2c(C(=O)Nc3cc4c(cc3N3CCOCC3)OC(C)(CO)C4)cncc21] | N-[2-(hydroxymethyl)-2-methyl-6-morpholino-3H-benzofuran-5-yl]-3-methyl-triazolo[4,5-c]pyridine-7-carboxamide |
| 53 | 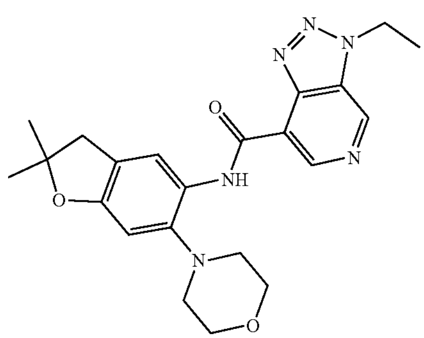 [SMILES: CCn1nnc2c(C(=O)Nc3cc4c(cc3N3CCOCC3)OC(C)(C)C4)cncc21] | N-(2,2-dimethyl-6-morpholino-3H-benzofuran-5-yl)-3-ethyl-triazolo[4,5-c]pyridine-7-carboxamide |
| 54 | 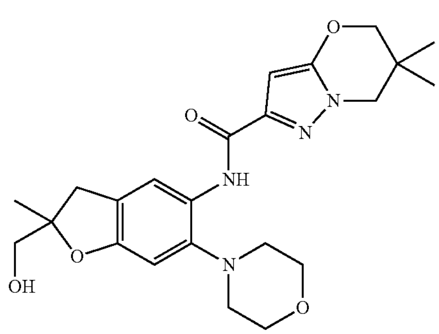 | N-[2-(hydroxymethyl)-2-methyl-6-morpholino-3H-benzofuran-5-yl]-6,6-dimethyl-5,7-dihydropyrazolo[5,1-b][1,3]oxazine-2-carboxamide |

TABLE 1-continued

Exemplary compounds of the present invention. Salts of such compounds are also contemplated. See the Examples section for preparation of such compounds.

| # | Structure | Name |
|---|---|---|
| 55 | 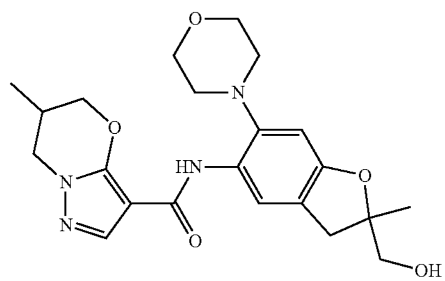 [SMILES: CC1COc2c(C(=O)Nc3cc4c(cc3N3CCOCC3)OC(C)(CO)C4)cnn2C1] | N-[2-(hydroxymethyl)-2-methyl-6-morpholino-3H-benzofuran-5-yl]-6-methyl-6,7-dihydro-5H-pyrazolo[5,1-b][1,3]oxazine-3-carboxamide |
| 56 | 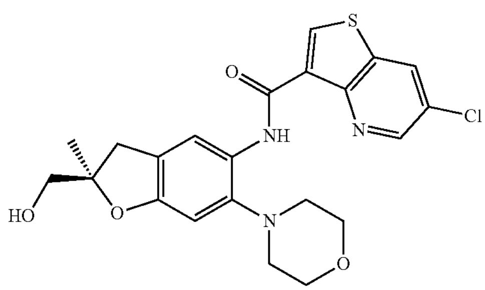 [SMILES: C[C@]1(CO)Cc2cc(NC(=O)c3csc4cc(Cl)cnc34)c(N3CCOCC3)cc2O1] | 6-chloro-N-[rac-(2R)-2-(hydroxymethyl)-2-methyl-6-morpholino-3H-benzofuran-5-yl]thieno[3,2-b]pyridine-3-carboxamide |
| 57 | 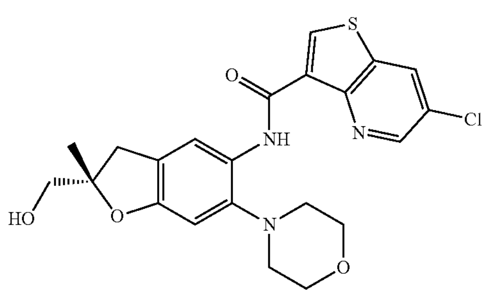 [SMILES: C[C@@]1(CO)Cc2cc(NC(=O)c3csc4cc(Cl)cnc34)c(N3CCOCC3)cc2O1] | 6-chloro-N-[rac-(2S)-2-(hydroxymethyl)-2-methyl-6-morpholino-3H-benzofuran-5-yl]thieno[3,2-b]pyridine-3-carboxamide |
| 58 | 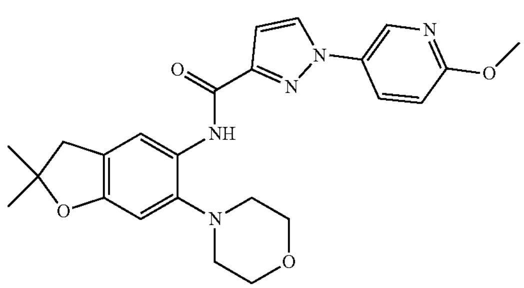 | N-(2,2-dimethyl-6-morpholino-3H-benzofuran-5-yl)-1-(6-methoxy-3-pyridyl)pyrazole-3-carboxamide |
| 59 | 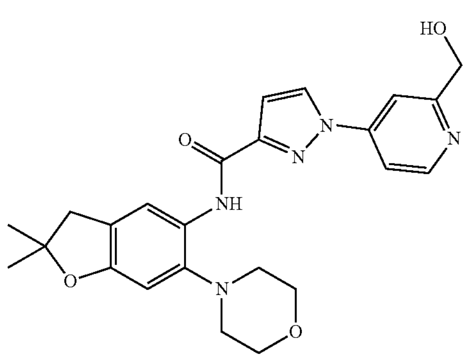 [SMILES: CC1(C)Cc2cc(NC(=O)c3ccn(-c4ccnc(CO)c4)n3)c(N3CCOCC3)cc2O1] | N-(2,2-dimethyl-6-morpholino-3H-benzofuran-5-yl)-1-[2-(hydroxymethyl)-4-pyridyl]pyrazole-3-carboxamide |

TABLE 1-continued

Exemplary compounds of the present invention. Salts of such compounds are also contemplated. See the Examples section for preparation of such compounds.

| # | Structure | Name |
|---|---|---|
| 60 | 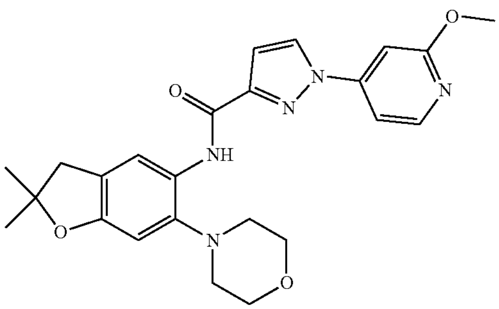 | N-(2,2-dimethyl-6-morpholino-3H-benzofuran-5-yl)-1-(2-methoxy-4-pyridyl)pyrazole-3-carboxamide |
| 61 | 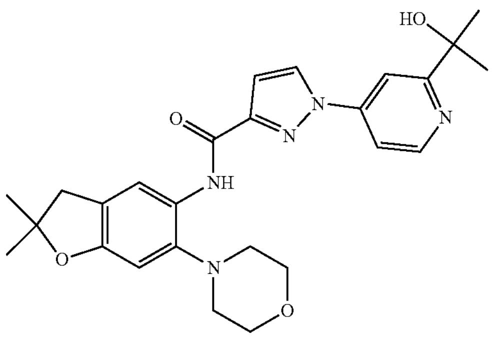 [SMILES: CC1(C)Cc2cc(NC(=O)c3ccn(-c4ccnc(C(C)(C)O)c4)n3)c(N3CCOCC3)cc2O1] | N-(2,2-dimethyl-6-morpholino-3H-benzofuran-5-yl)-1-[2-(1-hydroxy-1-methyl-ethyl)-4-pyridyl]pyrazole-3-carboxamide |
| 62 | 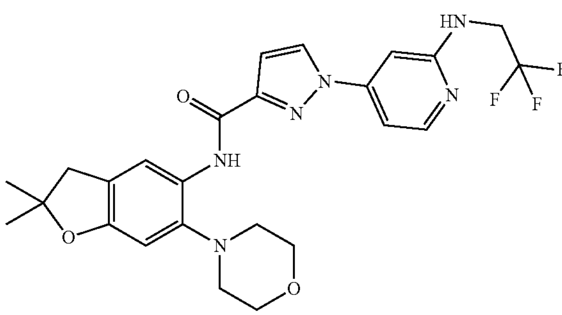 [SMILES: CC1(C)Cc2cc(NC(=O)c3ccn(-c4ccnc(NCC(F)(F)F)c4)n3)c(N3CCOCC3)cc2O1] | N-(2,2-dimethyl-6-morpholino-3H-benzofuran-5-yl)-1-[2-(2,2,2-trifluoroethylamino)-4-pyridyl]pyrazole-3-carboxamide |
| 63 | 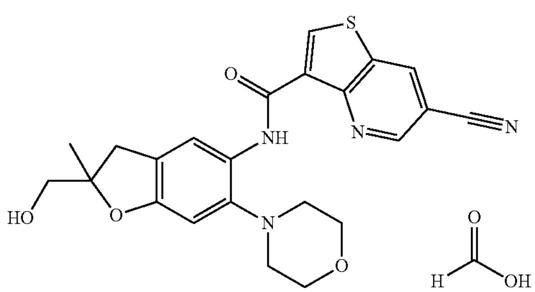 [SMILES: CC1(CO)Cc2cc(NC(=O)c3csc4cc(C#N)cnc34)c(N3CCOCC3)cc2O1 ; O=CO] | 6-cyano-N-[2-(hydroxymethyl)-2-methyl-6-morpholino-3H-benzofuran-5-yl]thieno[3,2-b]pyridine-3-carboxamide; formic acid |
| 64 | 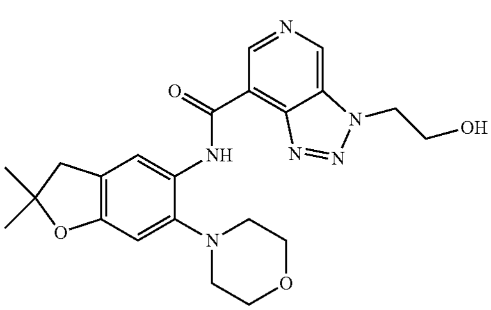 [SMILES: CC1(C)Cc2cc(NC(=O)c3cncc4c3nnn4CCO)c(N3CCOCC3)cc2O1] | N-(2,2-dimethyl-6-morpholino-3H-benzofuran-5-yl)-3-(2-hydroxyethyl)triazolo[4,5-c]pyridine-7-carboxamide |

TABLE 1-continued

Exemplary compounds of the present invention. Salts of such compounds are also contemplated. See the Examples section for preparation of such compounds.

| # | Structure | Name |
|---|---|---|
| 65 | 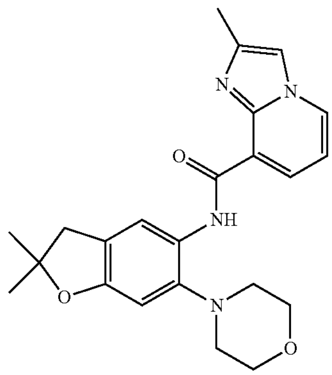 [SMILES: Cc1cn2cccc(C(=O)Nc3cc4c(cc3N3CCOCC3)OC(C)(C)C4)c2n1] | N-(2,2-dimethyl-6-morpholino-3H-benzofuran-5-yl)-2-methyl-imidazo[1,2-a]pyridine-8-carboxamide |
| 66 | 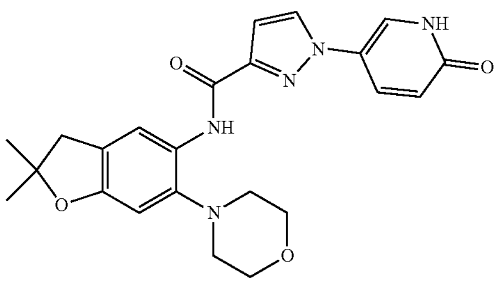 [SMILES: CC1(C)Cc2cc(NC(=O)c3ccn(-c4ccc(=O)[nH]c4)n3)c(N3CCOCC3)cc2O1] | N-(2,2-dimethyl-6-morpholino-3H-benzofuran-5-yl)-1-(6-oxo-1H-pyridin-3-yl)pyrazole-3-carboxamide |
| 67 | 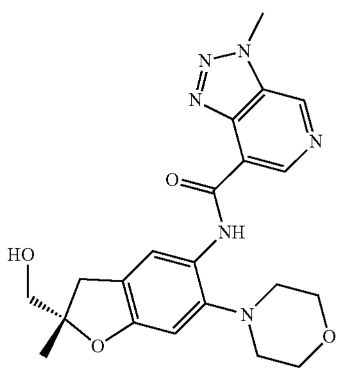 [SMILES: Cn1nnc2c(C(=O)Nc3cc4c(cc3N3CCOCC3)O[C@](C)(CO)C4)cncc21] | 3-methyl-N-[rac-(2S)-2-(hydroxymethyl)-2-methyl-6-morpholino-3H-benzofuran-5-yl]triazolo[4,5-c]pyridine-7-carboxamide |
| 68 | 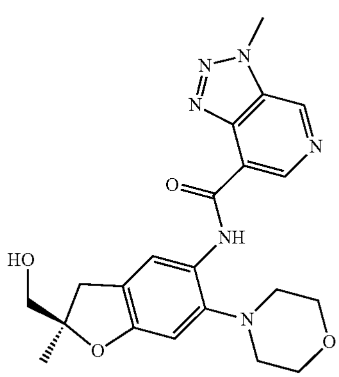 [SMILES: Cn1nnc2c(C(=O)Nc3cc4c(cc3N3CCOCC3)O[C@@](C)(CO)C4)cncc21] | 3-methyl-N-[rac-(2R)-2-(hydroxymethyl)-2-methyl-6-morpholino-3H-benzofuran-5-yl]triazolo[4,5-c]pyridine-7-carboxamide |

TABLE 1-continued

Exemplary compounds of the present invention. Salts of such compounds are also contemplated. See the Examples section for preparation of such compounds.

| # | Structure | Name |
|---|---|---|
| 69 | 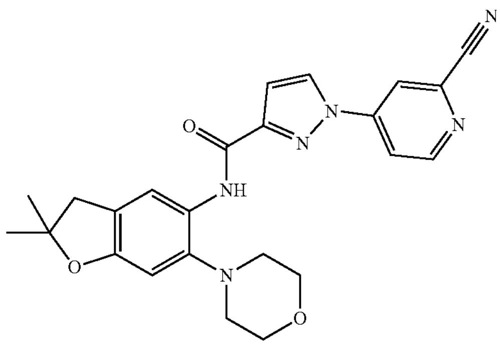 [SMILES: CC1(C)Cc2cc(NC(=O)c3ccn(-c4ccnc(C#N)c4)n3)c(N3CCOCC3)cc2O1] | 1-(2-cyano-4-pyridyl)-N-(2,2-dimethyl-6-morpholino-3H-benzofuran-5-yl)pyrazole-3-carboxamide |
| 70 | 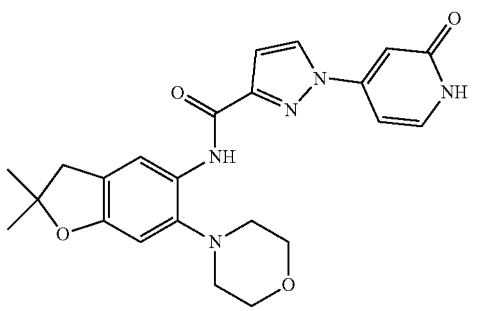 [SMILES: CC1(C)Cc2cc(NC(=O)c3ccn(-c4cc[nH]c(=O)c4)n3)c(N3CCOCC3)cc2O1] | N-(2,2-dimethyl-6-morpholino-3H-benzofuran-5-yl)-1-(2-oxo-1H-pyridin-4-yl)pyrazole-3-carboxamide |
| 71 | 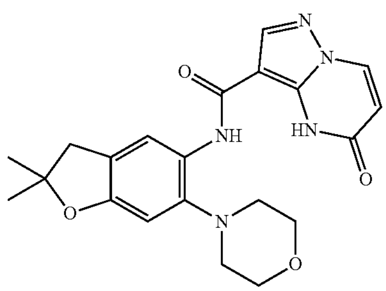 [SMILES: CC1(C)Cc2cc(NC(=O)c3cnn4ccc(=O)[nH]c34)c(N3CCOCC3)cc2O1] | N-(2,2-dimethyl-6-morpholino-3H-benzofuran-5-yl)-5-oxo-4H-pyrazolo[1,5-a]pyrimidine-3-carboxamide |

Synthesis of IRAK4 Inhibitors

Compounds of the present invention can be made by a variety of methods depicted in the illustrative synthetic reaction schemes shown and described below. The starting materials and reagents used in preparing these compounds generally are either available from commercial suppliers, such as Aldrich Chemical Co., or are prepared by methods known to those skilled in the art following procedures set forth in references such as Fieser and Fieser's *Reagents for Organic Synthesis*; Wiley & Sons: New York, vol. 1-21; R. C. LaRock, *Comprehensive Organic Transformations*, 2nd edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds.) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: New York, 1991, vol. 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

For illustrative purposes, reaction Schemes below provide routes for synthesizing the compounds of the invention as well as key intermediates. For a more detailed description of the individual reaction steps, see the Examples section below. Those skilled in the art will appreciate that other synthetic routes may be used. Although some specific starting materials and reagents are depicted in the Schemes and discussed below, other starting materials and reagents can be substituted to provide a variety of derivatives or reaction conditions. In addition, many of the compounds prepared by the methods described below can be further modified in light of this disclosure using conventional chemistry well known to those skilled in the art.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, or, about 20° C.

Some compounds in following schemes are depicted with generalized substituents; however, one skilled in the art will immediately appreciate that the nature of the R groups can varied to afford the various compounds contemplated in this invention. Moreover, the reaction conditions are exemplary and alternative conditions are well known. The reaction sequences in the following examples are not meant to limit the scope of the invention as set forth in the claims.

Methods of Treatment with and Uses of IRAK 4 Inhibitors

Compounds of the present invention are useful as IRAK4 inhibitors. Accordingly, in one embodiment is provided a method of contacting a cell, such as an ex vivo cell, with a compound of the present invention to inhibit IRAK4 activity in the cell.

Also provided is a pharmaceutical composition comprising a compound of Formula 0, or a stereoisomer or pharmaceutically acceptable salt thereof, and a pharmaceutically acceptable excipient, carrier or diluent. Compounds of the invention, including pharmaceutical compositions comprising such compounds, may be used in the methods described herein.

Further provided is a method of preventing, treating, or lessening the severity of a disease or condition responsive to the inhibition of IRAK4 in a patient, comprising administering to the patient a therapeutically effective amount of a compound of the present invention, or a stereoisomer or pharmaceutically acceptable salt thereof.

Also provided is a method for treating cancer in a patient, comprising administering to the patient a therapeutically effective amount of a compound of the present invention, or a stereoisomer or pharmaceutically acceptable salt thereof.

Further provided is a method for treating an inflammatory or autoimmune disease in a patient, comprising administering to the patient a therapeutically effective amount of a compound of the present invention, or a stereoisomer or pharmaceutically acceptable salt thereof. In some embodiments, the disease is selected from the group consisting of Crohn's disease, ulcerative colitis, inflammatory bowel disease (IBD), asthma, graft versus host disease, allograft rejection, chronic obstructive pulmonary disease (COPD), rheumatoid arthritis, systemic lupus erythematosus, lupus nephritis, cutaneous lupus, psoriasis, systemic onset juvenile idiopathic arthritis, multiple sclerosis, neuropathic pain, gout, and gouty arthritis.

In some embodiments, other diseases and conditions responsive to the inhibition of IRAK4 that can be treated using a compound of the present invention include metabolic syndromes, atherosclerosis, and neurodegeneration.

Further provided is the use of a compound of the present invention, or a stereoisomer or pharmaceutically acceptable salt thereof, in therapy. In some embodiments, use of a compound of the present invention, or a stereoisomer or pharmaceutically acceptable salt thereof, is provided in the treatment of an inflammatory disease. In some embodiments, use of a compound of the present invention, or a stereoisomer or pharmaceutically acceptable salt thereof, is provided for the preparation of a medicament for the treatment of an inflammatory disease. Furthermore, in some embodiments, a compound of the present invention, or a stereoisomer or pharmaceutically acceptable salt thereof, is provided for use in the treatment of an inflammatory disease.

In some embodiments, a disease or condition that may be treated is selected from the group consisting of acute kidney injury, acute respiratory distress syndrome, acute lung injury, adult onset Still's disease, allergic airway syndrome, allergic rhinitis, allograft rejection, asthma, atherosclerosis, atopic dermatitis, bronchitis, calcium pyrophosphate deposition disease (CPPD) also known as pseudo gout, cerebrovascular accident (e.g., stroke), chronic kidney disease, chronic obstructive pulmonary disease (COPD), contact dermatitis, Crohn's disease, cryopyrin-associated periodic syndromes (CAPS), cutaneous lupus, delayed hypersensitivity, diabetes, endometriosis, gout, gouty arthritis, graft vs host disease, graft rejection, inflammatory bowel disease (IBD), inflammatory myositis (e.g., polymyositis, dermatomyositis), interstitial lung disease, lupus, lupus nephritis, metabolic syndrome, multiple sclerosis, neurodegeneration, neuropathic pain, non-alcoholic fatty liver disease, obesity, psoriasis, rheumatoid arthritis, rhinitis, scleroderma, sepsis, systemic lupus erythematosus, systemic onset juvenile idiopathic arthritis, systemic sclerosis and ulcerative colitis.

Also provided is a method of inhibiting IRAK4 in a patient in need of therapy, comprising administering to the patient a compound of the present invention.

Dosage & Administration

The present invention provides pharmaceutical compositions or medicaments containing the compounds of the invention and at least one therapeutically inert carrier, diluent or excipient, as well as methods of using the compounds of the invention to prepare such compositions and medicaments. In one example, compounds of Formula 0, or a stereoisomer or pharmaceutically acceptable salt thereof, with the desired degree of purity may be formulated by mixing with physiologically acceptable carriers, i.e., carriers that are non-toxic to recipients at the dosages and concentrations employed into a dosage form at ambient temperature and at the appropriate pH. The pH of the formulation depends mainly on the particular use and the concentration of compound, but typically ranges anywhere from about 3 to about 8. In one example, a compound of Formula 0 is formulated in an acetate buffer, at pH 5. In another embodiment, the compounds of Formula 0 are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the severity of the disorder, the particular patient being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit IRAK4 activity. Typically such amount may be below the amount that is toxic to normal cells, or the patient as a whole.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Sustained-release preparations may be prepared. Suitable examples of sustained-release preparations include semipermeable matrices of solid hydrophobic polymers containing a compound of Formula 0, or a stereoisomer or pharmaceutically acceptable salt thereof, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides, copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

A dose to treat human patients may range from about 0.1 mg to about 1000 mg of a compound of Formula 0, or a stereoisomer or pharmaceutically acceptable salt thereof. A typical dose may be about 1 mg to about 300 mg of the compound. A dose may be administered once a day (QD), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal, epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, H. C., et al., Ansel's *Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, R. C., *Handbook of Pharmaceutical Excipients*, Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

For oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

An example of a suitable oral dosage form is a tablet containing about 25 mg, 50 mg, 100 mg, 250 mg or 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5-400 mg, of the invention in a suitable buffer solution, e.g. a phosphate buffer, adding a tonicifier, e.g. a salt such as sodium chloride, if desired. The solution may be filtered, e.g., using a 0.2 micron filter, to remove impurities and contaminants.

In one embodiment, the pharmaceutical composition also includes at least one additional anti-proliferative agent.

An embodiment, therefore, includes a pharmaceutical composition comprising a compound of Formula 0, or a stereoisomer or pharmaceutically acceptable salt thereof. A further embodiment includes a pharmaceutical composition comprising a compound of Formula 0, or a stereoisomer or pharmaceutically acceptable salt thereof, together with a pharmaceutically acceptable carrier or excipient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of Formula 0 may be employed alone or in combination with other therapeutic agents for the treatment of a disease or disorder described herein. The second compound of the pharmaceutical combination formulation or dosing regimen preferably has complementary activities to the compound of Formula 0 such that they do not adversely affect each other. The combination therapy may provide "synergy" and prove "synergistic", i.e., the effect achieved when the active ingredients used together is greater than the sum of the effects that results from using the compounds separately.

The combination therapy may be administered as a simultaneous or sequential regimen. When administered sequentially, the combination may be administered in two or more administrations. The combined administration includes co-administration, using separate formulations or a single pharmaceutical formulation, and consecutive administration in either order, wherein preferably there is a time period while both (or all) active agents simultaneously exert their biological activities.

Combination therapies according to the present invention thus comprise the administration of at least one compound of Formula 0, or a stereoisomer or pharmaceutically acceptable salt thereof, and the use of at least one other treatment method. The amounts of the compound(s) of Formula 0 and the other pharmaceutically active agent(s) and the relative timings of administration will be selected in order to achieve the desired combined therapeutic effect.

In some embodiments, a second agent that may be employed in combination therapy with a compound described herein may be an inhibitor of Bruton's tyrosine kinase (BTK), such as a small molecule BTK inhibitor. In some embodiments, the second agent may be prednisone.

Articles of Manufacture

In another embodiment of the invention, an article of manufacture, or "kit", containing materials useful for the treatment of the diseases and disorders described above is provided. In one embodiment, the kit comprises a container comprising a compound of Formula 0, or a stereoisomer or pharmaceutically acceptable salt thereof. The kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of Formula 0 or a formulation thereof which is effective for treating the condition and may have a sterile access port (for example, the container may be an intravenous solution bag or a vial having a stopper pierceable by a hypodermic injection needle). At least one active agent in the composition is a compound of Formula 0. Alternatively, or additionally, the article of manufacture may further comprise a second container comprising a pharmaceutical diluent, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In another embodiment, the kits are suitable for the delivery of solid oral forms of a compound of Formula 0, such as tablets or capsules. Such a kit can include a number of unit dosages. An example of such a kit is a "blister pack". Blister packs are well known in the packaging industry and are widely used for packaging pharmaceutical unit dosage forms.

The following examples illustrate the preparation and biological evaluation of compounds within the scope of the invention. These examples and preparations which follow are provided to enable those skilled in the art to more clearly understand and to practice the present invention. They should not be considered as limiting the scope of the invention, but merely as being illustrative and representative thereof.

Preparation of Intermediate:
2,2-Dimethyl-6-morpholino-3H-benzofuran-5-amine

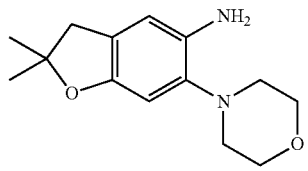

a. 2-Chloro-4-((2-methylallyl)oxy)-1-nitrobenzene

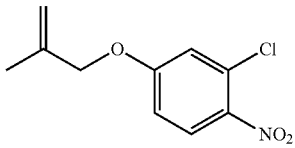

To a solution of 3-chloro-4-nitrophenol (25.2 g, 145 mmol) in acetonitrile (184 mL) was added 3-bromo-2-methylpropene (16.1 mL, 159 mmol) and potassium carbonate (28.0 g, 203 mmol). The reaction mixture was stirred at 55° C. for 18 h, diluted with isopropyl acetate, filtered and the precipitate was washed with isopropyl acetate and dichloromethane. The combined filtrates were concentrated under reduced pressure and purified by silica gel chromatography (eluting gradient 0-40% 3:1 isopropyl acetate in methanol: heptane) to afford the title compound as a light yellow oil (32.7 g, 99%). $^1$H NMR (400 MHz, dimethyl sulfoxide-$d_6$) δ 8.10 (d, J=9.1 Hz, 1H), 7.34 (d, J=2.7 Hz, 1H), 7.14 (dd, J=9.2, 2.7 Hz, 1H), 5.13-5.03 (m, 1H), 5.05-4.97 (m, 1H), 4.66 (s, 2H), 1.83-1.68 (m, 3H).

b. 4-(5-((2-Methylallyl)oxy)-2-nitrophenyl)morpholine

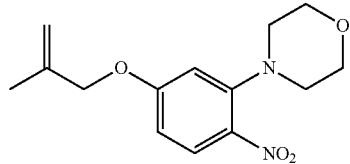 [SMILES: C=C(C)COc1ccc([N+](=O)[O-])c(N2CCOCC2)c1]

To a mixture of 2-chloro-4-((2-methylallyl)oxy)-1-nitrobenzene (3.01 g, 13.2 mmol), and potassium carbonate (6.03 g, 43.7 mmol) in dimethyl sulfoxide (20.1 mL, 280 mmol) was added morpholine (1.15 g, 13.2 mmol) and the mixture was heated to 100° C. in a sealed tube for 1 h. The mixture was cooled to room temperature and diluted with water and ethyl acetate. The organic phase was extracted and washed with saturated sodium bicarbonate solution, water and brine and dried over sodium sulfate before concentration under reduced pressure. The crude residue was purified by silica gel chromatography (eluting gradient 0-50% isopropyl acetate:heptane) to afford the title compound as a bright yellow solid (3.22 g, 11.6 mmol, 88%). $^1$H NMR (400 MHz, dimethyl sulfoxide-$d_6$) δ 7.90 (d, J=9.0 Hz, 1H), 6.71 (d, J=2.6 Hz, 1H), 6.68 (dd, J=9.0, 2.6 Hz, 1H), 5.08 (d, J=0.8

Hz, 1H), 4.99 (s, 1H), 4.59 (s, 2H), 3.76-3.63 (m, 4H), 3.06-2.95 (m, 4H), 1.82-1.72 (m, 3H).

c. 2-(2-Methylallyl)-5-morpholino-4-nitrophenol

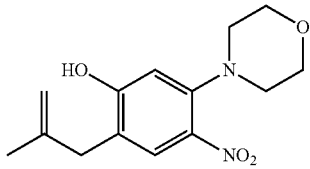 [SMILES: C=C(C)Cc1cc([N+](=O)[O-])c(N2CCOCC2)cc1O]

Five separate reactions containing 4-(5-((2-methylallyl)oxy)-2-nitrophenyl)morpholine (5.0 g, 18 mmol) in N,N-dimethylformamide (15 mL, 190 mmol) were heated at 220° C. in the microwave for 60 min. The reaction mixtures were combined, concentrated under reduced pressure and brought up in isopropyl acetate and washed with water and brine. The combined aqueous phases were extracted with isopropyl acetate. The combined organic phases were dried over sodium sulfate before concentration under reduced pressure. The crude residue was purified by silica gel chromatography (eluting gradient 0-50% isopropyl acetate in heptane) to afford the title compound as a dark orange oil (3.53 g, 12.7 mmol, 12%). $^1$H NMR (400 MHz, dimethyl sulfoxide-$d_6$) δ 10.72 (s, 1H), 7.74 (s, 1H), 6.59 (s, 1H), 4.80-4.74 (m, 1H), 4.67-4.60 (m, 1H), 3.71 (q, J=4.0, 3.6 Hz, 4H), 3.20 (s, 2H), 2.95-2.90 (m, 4H), 1.66 (s, 3H). $^1$H NMR (400 MHz, Chloroform-d) δ 7.82 (s, 1H), 6.54 (s, 1H), 6.02 (s, 1H), 5.03-4.96 (m, 1H), 4.94-4.92 (m, 1H), 3.92-3.83 (m, 4H), 3.36 (s, 2H), 3.04 (dd, J=5.5, 3.7 Hz, 4H), 1.75 (s, 3H).

d. 4-(2,2-Dimethyl-5-nitro-2,3-dihydrobenzofuran-6-yl)morpholine

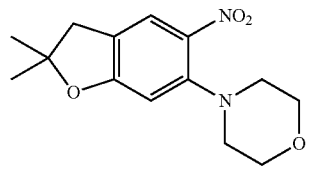 [SMILES: CC1(C)Cc2cc([N+](=O)[O-])c(N3CCOCC3)cc2O1]

2-(2-Methylallyl)-5-morpholino-4-nitrophenol (1.0 g, 3.6 mmol) was dissolved in methanol (12 mL) and cooled to 0° C. A solution of 35% aqueous HCl (12 mL) was added and the reaction mixture was allowed to warm to ambient temperature and then heated at reflux for 60 h. The reaction was cooled to room temperature, neutralized with saturated sodium bicarbonate and extracted with isopropyl acetate. The organic phase was dried over sodium sulfate, filtered, and absorbed onto celite under reduced pressure. The crude residue was purified by silica gel chromatography (eluting gradient 0-30% isopropyl acetate in heptanes) to afford the title compound as a yellow foam (520 mg, 1.87 mmol, 52%). $^1$H NMR (400 MHz, dimethyl sulfoxide-$d_6$) δ 7.85 (t, J=1.2 Hz, 1H), 6.60 (s, 1H), 3.76-3.61 (m, 4H), 3.01 (d, J=1.1 Hz, 2H), 2.98-2.90 (m, 4H), 1.44 (s, 6H). $^1$H NMR (400 MHz, Chloroform-d) δ 7.85 (t, J=1.2 Hz, 1H), 6.44 (s, 1H), 3.90-3.79 (m, 4H), 3.05-3.01 (m, 4H), 3.00 (d, J=1.1 Hz, 2H), 1.51 (s, 6H).

e. 2,2-Dimethyl-6-morpholino-3H-benzofuran-5-amine

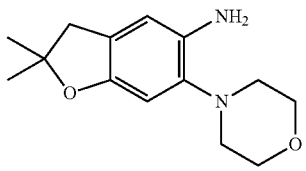 [SMILES: CC1(C)Cc2cc(N)c(N3CCOCC3)cc2O1]

The mixture of 4-(2,2-dimethyl-5-nitro-3H-benzofuran-6-yl)morpholine (60 mg, 0.22 mmol) and 10% palladium on carbon (30 mg) in methanol (8 mL) was stirred under a hydrogen atmosphere at 25° C. for 1 h. After filtration through a plug of celite and concentration, 2,2-dimethyl-6-morpholino-3H-benzofuran-5-amine (50 mg) was afforded as a yellow oil, which was used without further purification. MS (ESI): m/z=249.2 [M+1]$^+$.

Preparation of Intermediate (6-Chloro-2-methyl-5-nitro-2,3-dihydrobenzofuran-2-yl)methanol

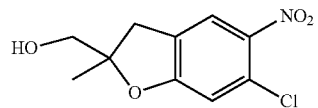 [SMILES: CC1(CO)Cc2cc([N+](=O)[O-])c(Cl)cc2O1]

a. Methyl 3-(4-chloro-2-fluoro-phenyl)-2-hydroxy-2-methyl-propanoate

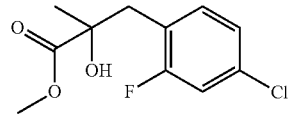 [SMILES: COC(=O)C(C)(O)Cc1ccc(Cl)cc1F]

To a solution of magnesium (1.35 g, 56.3 mmol) and iodine (100 mg, 0.39 mmol) in diethyl ether (50 mL) heated at reflux was added 1-(bromomethyl)-4-chloro-2-fluoro-benzene (5.0 g, 22.4 mmol) drop wise. The reaction was stirred for 30 min. The solution was then added to a solution of methyl pyruvate (2.3 g, 22.5 mmol) in diethyl ether (50 mL) at −78° C. and stirred for 30 min followed by warming to room temperature for 2 h. Saturated ammonium chloride and ethyl acetate (200 mL) were added and the organic phase was separated and dried over sodium sulfate. The reaction was filtered and the filtrate was concentrated under reduced pressure. The residue was purified by silica gel chromatography (eluting gradient 1:20 to 1:10 ethyl acetate: petroleum ether) to afford methyl 3-(4-chloro-2-fluoro-phenyl)-2-hydroxy-2-methyl-propanoate (2.8 g, 51%) as a yellow oil. $^1$H NMR (400 MHz, CDCl$_3$): δ 7.33-7.25 (m, 1H), 7.18-7.09 (m, 2H), 3.73 (s, 3H), 3.03 (s, 2H), 1.39 (s, 3H).

b. 6-Chloro-2-methyl-3H-benzofuran-2-carboxylic acid

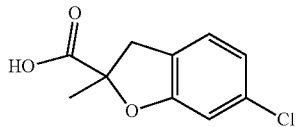

A mixture of methyl 3-(4-chloro-2-fluoro-phenyl)-2-hydroxy-2-methyl-propanoate (493.0 mg, 2 mmol) and potassium tert-butanolate (561 mg, 5 mmol) in tetrahydrofuran (10 mL) was stirred at 60° C. for 18 h. After cooling to room temperature, water and a 1 N hydrochloric acid solution were added until pH=3. Ethyl acetate (20 mL) was added and the organic phase was separated and dried over sodium sulfate. The reaction was filtered, and the filtrate was concentrated under reduced pressure. The residue was purified by silica gel chromatography (eluting gradient 1:1 to 2:1 ethyl acetate: petroleum ether) to afford 6-chloro-2-methyl-3H-benzofuran-2-carboxylic acid (271 mg, 64%) as a yellow solid. $^1$H NMR (400 MHz, CDCl$_3$) δ 10.95-10.24 (m, 1H), 7.04 (d, J 8.0 Hz, 1H), 6.87 (dd, J 1.6, 9.2 Hz, 1H), 6.85 (s, 1H), 3.59 (d, J 16 Hz, 1H), 3.13 (d, J 16 Hz, 1H), 1.73, (s, 3H).

c. Chloro-2-methyl-5-nitro-3H-benzofuran-2-carboxylic acid

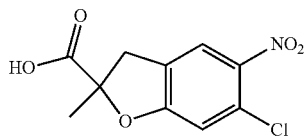 [SMILES: CC1(C(=O)O)Cc2cc([N+](=O)[O-])c(Cl)cc2O1]

To a solution of 6-chloro-2-methyl-3H-benzofuran-2-carboxylic acid (230 mg, 1.08 mmol) in dichloromethane (10 mL) at 25° C. was slowly added fuming nitric acid (0.5 mL). The resulting solution was stirred for 5 min. Water and ethyl acetate (20 mL) were added and the organic phase was separated and dried over sodium sulfate. The reaction was filtered, and the filtrate was concentrated under reduced pressure. The residue was purified by silica gel chromatography (eluting gradient 1:4 to 1:3 ethyl acetate: petroleum ether) to afford 6-chloro-2-methyl-5-nitro-3H-benzofuran-2-carboxylic acid (150 mg, 54%) as an orange solid. $^1$H NMR (400 MHz, CDCl$_3$) δ 7.84 (s, 1H), 6.99 (s, 1H), 3.68 (d, J=16.8 Hz, 1H), 3.23 (d, J=16.8 Hz, 1H), 1.80 (s, 3H).

d. (6-Chloro-2-methyl-5-nitro-3H-benzofuran-2-yl)methanol

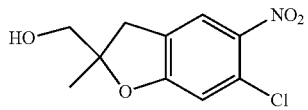 [SMILES: CC1(CO)Cc2cc([N+](=O)[O-])c(Cl)cc2O1]

A mixture of 6-chloro-2-methyl-5-nitro-3H-benzofuran-2-carboxylic acid (1.93 g, 7.5 mmol) and borane (1 M in tetrahydrofuran, 14.0 mL, 14 mmol) in tetrahydrofuran (75 mL) was stirred at 25° C. for 2 h. Methanol (10 mL) was slowly added and the reaction was concentrated under reduced pressure. The residue was purified by silica gel chromatography (eluting 1:1 ethyl acetate: petroleum ether) to afford (6-chloro-2-methyl-5-nitro-3H-benzofuran-2-yl)methanol (580 mg, 32%) as a yellow oil. $^1$H NMR (400 MHz, dimethyl sulfoxide-d$_6$): δ 7.84 (s, 1H), 6.99 (s, 1H), 6.60-5.80 (m, 1H), 3.68 (d, J=16.8 Hz, 1H), 3.23 (d, J=16.8 Hz, 1H), 1.80 (s, 3H). MS (ESI): m/z=244.1 [M+1]$^+$.

Preparation of Intermediate (5-Amino-2-methyl-6-morpholino-2,3-dihydrobenzofuran-2-yl)methanol

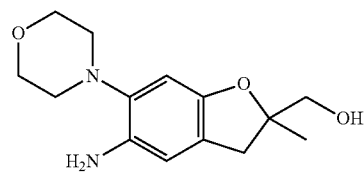

a. (2-Methyl-6-morpholino-5-nitro-2,3-dihydrobenzofuran-2-yl)methanol

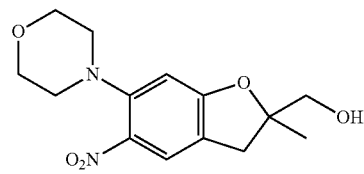 [SMILES: CC1(CO)Cc2cc([N+](=O)[O-])c(N3CCOCC3)cc2O1]

A mixture of (6-chloro-2-methyl-5-nitro-2,3-dihydrobenzofuran-2-yl)methanol (900 mg, 3.70 mmol) was stirred in morpholine (5 mL) at 120° C. for 18 h. The mixture was concentrated under reduced pressure and the residue purified by silica gel chromatography (eluent 1:1 ethyl acetate: petroleum ether) to afford (2-methyl-6-morpholino-5-nitro-2,3-dihydrobenzofuran-2-yl)methanol (780 mg, 72%) as a yellow oil. MS (ESI): m/z=295.1 [M+1]$^+$.

b. (5-Amino-2-methyl-6-morpholino-2,3-dihydrobenzofuran-2-yl)methanol

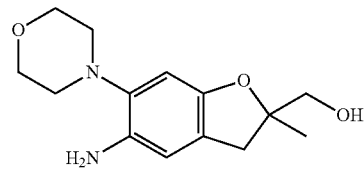

A mixture of (2-methyl-6-morpholino-5-nitro-3H-benzofuran-2-yl)methanol (780 mg, 2.65 mmol) and 10% palladium on carbon (200 mg) in methanol (30 mL) was stirred at 25° C. under a hydrogen atmosphere for 1 h. The reaction was filtered, and the filtrate was concentrated under reduced pressure to afford (5-amino-2-methyl-6-morpholino-2,3-dihydrobenzofuran-2-yl)methanol (550 mg) as a light green oil, which was used without further purification. MS (ESI): m/z=265.1 [M+1]⁺.

Example 1. N-(2,2-Dimethyl-6-morpholino-2,3-dihydrobenzofuran-5-yl)-6,7-dihydro-5H-pyrazolo[5,1-b][1,3]oxazine-3-carboxamide

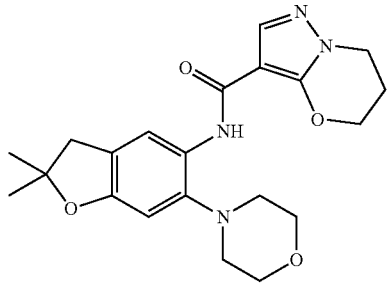 [SMILES: CC1(C)Cc2cc(NC(=O)c3cnn4c3OCCC4)c(N3CCOCC3)cc2O1]

A mixture of 6,7-dihydro-5H-pyrazolo[5,1-b][1,3]oxazine-3-carboxylic acid (130 mg, 0.76 mmol), (7-azabenzotriazol-1-yloxy)tripyrrolidinophosphonium hexafluorophosphate (360 mg, 0.66 mmol), 2,4,6-trimethylpyridine (0.088 mL, 0.66 mmol), and 2,2-dimethyl-6-morpholino-3H-benzofuran-5-amine (150 mg, 0.60 mmol) in N,N-dimethylformamide (2.0 mL) was stirred at room temperature overnight. After concentration, the residue was purified by preparative HPLC ((Gemini NX, 5*3 cm c18, 5 um; A: acetonitrile 20-60%; B: 0.1% ammonium hydroxide in water) to afford N-(2,2-dimethyl-6-morpholino-2,3-dihydrobenzofuran-5-yl)-6,7-dihydro-5H-pyrazolo[5,1-b][1,3]oxazine-3-carboxamide (230 mg, 0.57 mmol, 95% yield) as a solid. ¹H NMR (400 MHz, DMSO-d₆) δ 8.99 (s, 1H), 8.17 (s, 1H), 7.67 (s, 1H), 6.68 (s, 1H), 4.67-4.57 (m, 2H), 4.15 (t, J=6.1 Hz, 2H), 3.80-3.70 (m, 4H), 2.97 (s, 2H), 2.79-2.71 (m, 4H), 2.35-2.24 (m, 2H), 1.39 (s, 6H). MS (ESI): m/z=399.2 [M+1]⁺.

The following compounds were made in a manner similar to that described for Example 1:

| Ex. | Name | Structure | NMR, MS |
|---|---|---|---|
| 2 | N-(2,2-Dimethyl-6-morpholino-2,3-dihydrobenzofuran-5-yl)-6-hydroxypyridazine-3-carboxamide | 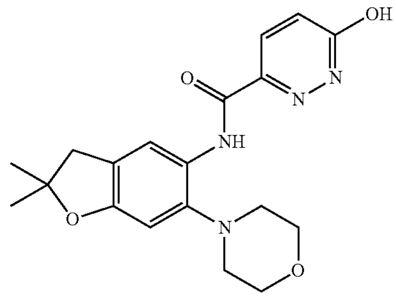 [SMILES: CC1(C)Cc2cc(NC(=O)c3ccc(O)nn3)c(N3CCOCC3)cc2O1] | ¹H NMR (400 MHz, DMSO-d₆) δ 13.59 (s, 1H), 10.04 (s, 1H), 8.14 (d, J = 1.0 Hz, 1H), 7.94 (d, J = 9.8 Hz, 1H), 7.03 (d, J = 9.8 Hz, 1H), 6.71 (s, 1H), 3.89-3.72 (m, 4H), 3.00 (d, J = 1.1 Hz, 2H), 2.88-2.70 (m, 4H), 1.41 (s, 6H), MS (ESI): m/z = 371.1 [M + 1]⁺. |
| 3 | 4-Amino-N-(2,2-dimethyl-6-morpholino-2,3-dihydrobenzofuran-5-yl)thieno[3,2-d]pyrimidine-7-carboxamide | 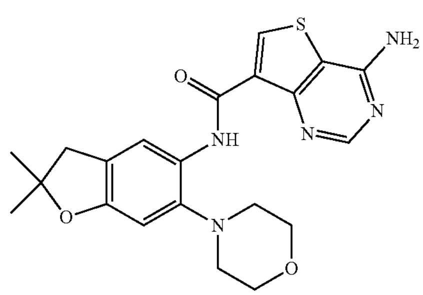 [SMILES: CC1(C)Cc2cc(NC(=O)c3csc4c(N)ncnc34)c(N3CCOCC3)cc2O1] | ¹H NMR (400 MHz, DMSO-d₆) δ 11.71 (s, 1H), 8.86 (s, 1H), 8.62 (s, 1H), 8.23 (q, J = 0.9 Hz, 1H), 7.86 (s, 2H), 6.66 (s, 1H), 3.89-3.73 (m, 4H), 3.00 (d, J = 1.1 Hz, 2H), 2.90-2.74 (m, 4H), 1.42 (s, 6H). MS (ESI): m/z = 426.1 [M + 1]⁺. |
| 4 | N-(2,2-Dimethyl-6-morpholino-2,3-dihydrobenzofuran-5-yl)-1H-benzo[d][1,2,3]triazole-4-carboxamide | 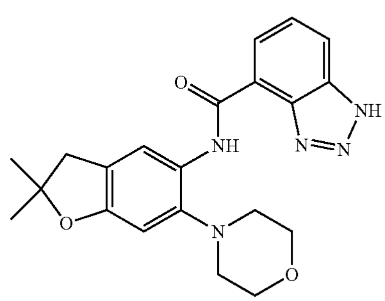 [SMILES: CC1(C)Cc2cc(NC(=O)c3cccc4[nH]nnc34)c(N3CCOCC3)cc2O1] | ¹H NMR (400 MHz, DMSO-d₆) δ 11.75 (s, 1H), 8.42 (s, 1H), 8.15 (dd, J = 7.3, 0.7 Hz, 1H), 8.09 (d, J = 8.2 Hz, 1H), 7.69 (dd, J = 8.2, 7.4 Hz, 1H), 6.76 (s, 1H), 3.88 (m, 4H), 3.03 (s, 2H), 2.92-2.80 (m, 4H), 1.43 (s, 6H). MS (ESI): m/z = 394.1 [M + 1]⁺. |

-continued

| Ex. | Name | Structure | NMR, MS |
|---|---|---|---|
| 5 | 5-Cyano-N-(2,2-dimethyl-6-morpholino-2,3-dihydrobenzofuran-5-yl)-6-methylpicolinamide | 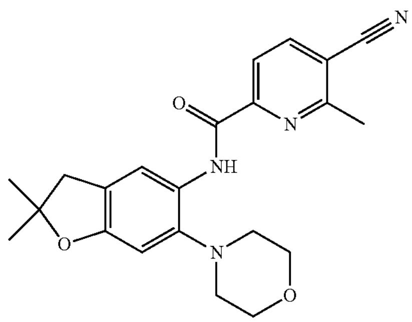 [SMILES: Cc1nc(C(=O)Nc2cc3c(cc2N2CCOCC2)OC(C)(C)C3)ccc1C#N] | $^1$H NMR (400 MHz, DMSO-$d_6$) δ 10.94 (s, 1H), 8.51 (d, J = 8.0 Hz, 1H), 8.32 (d, J = 1.1 Hz, 1H), 8.13 (dd, J = 8.1, 0.7 Hz, 1H), 6.77 (s, 1H), 3.91-3.81 (m, 4H), 3.02 (d, J = 1.1 Hz, 2H), 2.85 (s, 3H), 2.85-2.82 (m, 4H), 1.42 (s, 6H). MS (ESI): m/z = 393.2 [M + 1]$^+$. |
| 6 | N-(2,2-Dimethyl-6-morpholino-2,3-dihydrobenzofuran-5-yl)-2-methylthiazole-4-carboxamide | 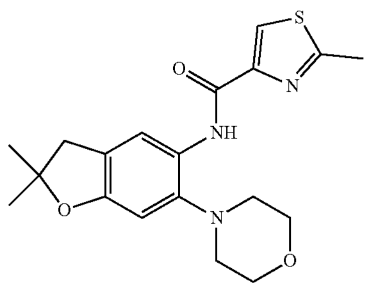 | $^1$H NMR (400 MHz, DMSO-$d_6$) δ 10.24 (s, 1H), 8.22 (d, J = 2.9 Hz, 2H), 6.70 (s, 1H), 3.92-3.75 (m, 4H), 3.00 (d, J = 1.1 Hz, 2H), 2.85-2.78 (m, 4H), 2.77 (s, 3H), 1.41 (s, 6H). MS (ESI): m/z = 374.1 [M + 1]$^+$. |
| 7 | N-(2,2-Dimethyl-6-morpholino-2,3-dihydrobenzofuran-5-yl)-6-methylpyrazine-2-carboxamide | 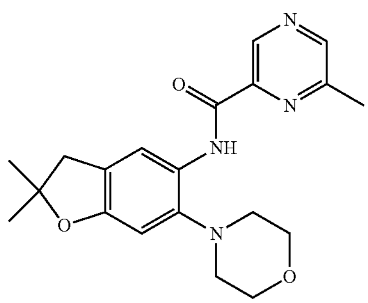 | $^1$H NMR (400 MHz, DMSO-$d_6$) δ 10.78 (s, 1H), 9.11 (s, 1H), 8.85 (s, 1H), 8.30 (d, J = 1.1 Hz, 1H), 6.75 (s, 1H), 3.90-3.77 (m, 4H), 3.02 (d, J = 1.4 Hz, 2H), 2.89-2.72 (m, 4H), 2.68 (s, 3H), 1.42 (s, 6H). MS (ESI): m/z = 369.1 [M + 1]$^+$. |
| 8 | N-(2,2-Dimethyl-6-morpholino-2,3-dihydrobenzofuran-5-yl)-6-fluoropicolinamide | 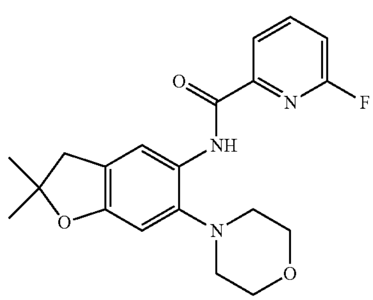 [SMILES: CC1(C)Cc2cc(NC(=O)c3cccc(F)n3)c(N3CCOCC3)cc2O1] | $^1$H NMR (400 MHz, DMSO-$d_6$) δ 10.60 (s, 1H), 8.36-8.20 (m, 2H), 8.09 (ddd, J = 7.5, 2.4, 0.8 Hz, 1H), 7.51 (ddd, J = 8.3, 2.3, 0.8 Hz, 1H), 6.74 (s, 1H), 3.89-3.82 (m, 4H), 3.02 (d, J = 1.2 Hz, 2H), 2.86-2.78 (m, 4H), 1.42 (s, 6H). MS (ESI): m/z = 372.1 [M + 1]$^+$. |
| 9 | N-(2,2-Dimethyl-6-morpholino-2,3-dihydrobenzofuran-5-yl)-2-(methylsulfonyl)pyrimidine-4-carboxamide | 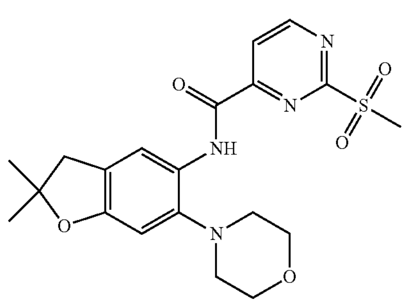 | $^1$H NMR (400 MHz, DMSO-$d_6$) δ 10.88 (s, 1H), 9.37 (d, J = 5.0 Hz, 1H), 8.40 (d, J = 5.0 Hz, 1H), 8.32 (d, J = 1.1 Hz, 1H), 6.80 (s, 1H), 3.93-3.83 (m, 4H), 3.52 (s, 3H), 3.03 (d, J = 1.3 Hz, 2H), 2.85-2.74 (m, 4H), 1.42 (s, 6H). MS (ESI): m/z = 433.1 [M + 1]$^+$. |

| Ex. | Name | Structure | NMR, MS |
|---|---|---|---|
| 10 | N-(2,2-Dimethyl-6-morpholino-2,3-dihydrobenzofuran-5-yl)furo[2,3-c]pyridine-2-carboxamide | 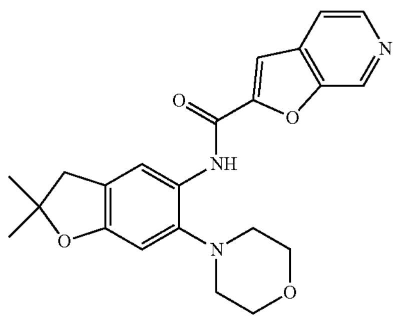 [SMILES: CC1(C)Cc2cc(NC(=O)c3cc4ccncc4o3)c(N3CCOCC3)cc2O1] | $^1$H NMR (400 MHz, DMSO-$d_6$) δ 9.80 (s, 1H), 9.15 (d, J = 1.0 Hz, 1H), 8.51 (d, J = 5.2 Hz, 1H), 8.00 (s, 1H), 7.85 (dd, J = 5.2, 1.1 Hz, 1H), 7.76 (s, 1H), 6.74 (s, 1H), 3.90-3.79 (m, 4H), 3.02 (d, J = 1.4 Hz, 2H), 2.90-2.78 (m, 4H), 1.42 (s, 6H). MS (ESI): m/z = 394.1 [M + 1]$^+$. |
| 11 | N-(2,2-Dimethyl-6-morpholino-2,3-dihydrobenzofuran-5-yl)pyrazine-2-carboxamide | 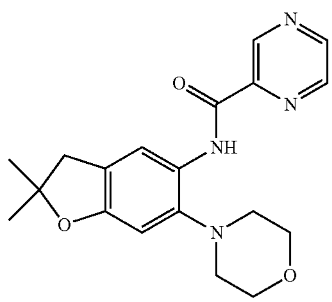 [SMILES: CC1(C)Cc2cc(NC(=O)c3cnccn3)c(N3CCOCC3)cc2O1] | MS (ESI): m/z = 355.1 [M + 1]$^+$. |
| 12 | N-(2,2-Dimethyl-6-morpholino-2,3-dihydrobenzofuran-5-yl)-2-oxo-1,2-dihydropyridine-3-carboxamide | 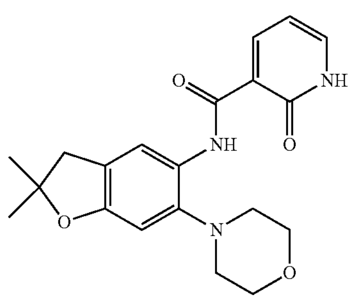 [SMILES: CC1(C)Cc2cc(NC(=O)c3ccc[nH]c3=O)c(N3CCOCC3)cc2O1] | $^1$H NMR (400 MHz, DMSO-$d_6$) δ 12.65 (d, J = 5.8 Hz, 1H), 12.19 (s, 1H), 8.43 (dd, J = 7.2, 2.2 Hz, 1H), 8.35 (d, J = 1.0 Hz, 1H), 7.75 (td, J = 6.2, 2.3 Hz, 1H), 6.62 (s, 1H), 6.52 (dd, J = 7.3, 6.2 Hz, 1H), 3.90-3.79 (m, 4H), 2.97 (d, J = 1.2 Hz, 2H), 2.81-2.73 (m, 4H), 1.40 (s, 6H). MS (ESI): m/z = 370.2 [M + 1]$^+$. |
| 13 | N-(2,2-Dimethyl-6-morpholino-2,3-dihydrobenzofuran-5-yl)-5-methylpyrazine-2-carboxamide | 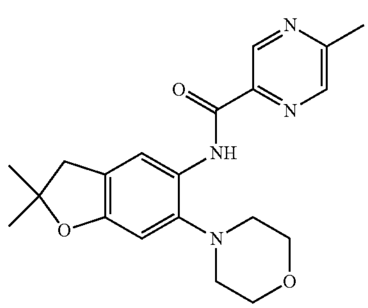 | $^1$H NMR (400 MHz, DMSO-$d_6$) δ 10.62 (s, 1H), 9.16 (d, J = 1.4 Hz, 1H), 8.75 (dd, J = 1.5, 0.6 Hz, 1H), 8.25 (d, J = 1.1 Hz, 1H), 6.72 (s, 1H), 3.90-3.70 (m, 4H), 3.02 (d, J = 1.3 Hz, 2H), 2.88-2.75 (m, 4H), 2.63 (s, 3H), 1.42 (s, 6H). MS (ESI): m/z = 369.2 [M + 1]$^+$. |
| 14 | N-(2,2-Dimethyl-6-morpholino-2,3-dihydrobenzofuran-5-yl)-1,2,5-thiadiazole-3-carboxamide | 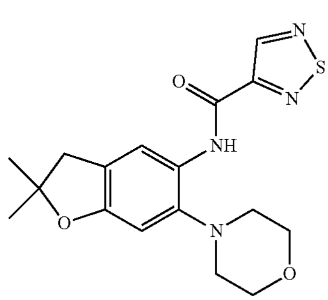 [SMILES: CC1(C)Cc2cc(NC(=O)c3cnsn3)c(N3CCOCC3)cc2O1] | $^1$H NMR (400 MHz, DMSO-$d_6$) δ 9.97 (s, 1H), 9.30 (s, 1H), 8.12 (d, J = 1.0 Hz, 1H), 6.74 (s, 1H), 3.86-3.73 (m, 4H), 3.02 (d, J = 1.2 Hz, 2H), 2.86-2.77 (m, 4H), 1.42 (s, 6H). MS (ESI): m/z = 361.1 [M + H]$^+$. |

| Ex. | Name | Structure | NMR, MS |
|---|---|---|---|
| 15 | N-(2,2-Dimethyl-6-morpholino-2,3-dihydrobenzofuran-5-yl)imidazo[1,2-b]pyridazine-3-carboxamide | 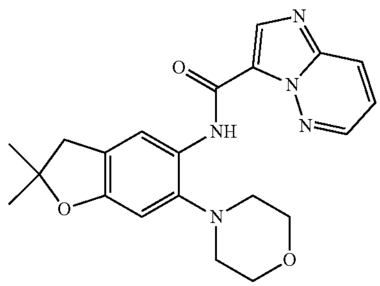 [SMILES: CC1(C)Cc2cc(NC(=O)c3cnc4cccnn34)c(N3CCOCC3)cc2O1] | $^1$H NMR (400 MHz, DMSO-d$_6$) δ 11.00 (s, 1H), 8.96 (dd, J = 4.6, 1.5 Hz, 1H), 8.43 (s, 1H), 8.42 (dd, J = 9.3, 1.5 Hz, 1H), 8.31 (s, 1H), 7.54 (dd, J = 9.2, 4.6 Hz, 1H), 6.74 (s, 1H), 3.88-3.76 (m, 4H), 3.01 (s, 2H), 2.90-2.76 (m, 4H), 1.42 (s, 6H). MS (ESI): m/z = 394.1 [M + H]$^+$. |
| 16 | (S)-N-(2-(Hydroxymethyl)-2-methyl-6-morpholino-2,3-dihydrobenzofuran-5-yl)-1-methyl-1H-pyrazole-3-carboxamide | | Example 16, Peak 1: $^1$H NMR (400 MHz, DMSO-d$_6$) δ 9.72 (s, 1H), 8.14 (s, 1H), 7.86 (d, J = 2.3 Hz, 1H), 6.71 (d, J = 2.3 Hz, 1H), 6.67 (s, 1H), 5.02 (t, J = 5.3 Hz, 1H), 3.96 (s, 3H), 3.87-3.77 (m, 4H), 3.42 (h, J = 5.9, 5.4 Hz, 2H), 3.19 (d, J = 16.5 Hz, 1H), 2.87-2.75 (m, 5H), 1.33 (s, 3H). MS (ESI): m/z = 373.2 [M + 1]$^+$. | and

| Ex. | Name | Structure | NMR, MS |
|---|---|---|---|
| 17 | (R)-N-(2-(Hydroxymethyl)-2-methyl-6-morpholino-2,3-dihydrobenzofuran-5-yl)-1-methyl-1H-pyrazole-3-carboxamide (absolute stereochemistry assigned arbitrarily) | | Example 17, Peak 2: $^1$H NMR (400 MHz, DMSO-d$_6$) δ 9.72 (s, 1H), 8.14 (s, 1H), 7.86 (d, J = 2.3 Hz, 1H), 6.71 (d, J = 2.3 Hz, 1H), 6.67 (s, 1H), 5.02 (t, J = 5.3 Hz, 1H), 3.96 (s, 3H), 3.87-3.77 (m, 4H), 3.42 (h, J = 5.9, 5.4 Hz, 2H), 3.19 (d, J = 16.5 Hz, 1H), 2.87-2.75 (m, 5H), 1.33 (s, 3H). MS (ESI): m/z = 373.2 [M + 1]$^+$. |
| 18 | N-[(2S)-2-(Hydroxymethyl)-2-methyl-6-morpholino-3H-benzofuran-5-yl]pyrrolo[1,2-b]pyridazine-7-carboxamide | | Example 18, Peak 1: $^1$H NMR (400 MHz, CDCl$_3$) δ 11.34 (s, 1H), 8.45 (s, 1H), 8.39-8.38 (m, 1H), 7.95 (d, J = 7.2 Hz, 1H), 7.82 (d, J = 4.4 Hz, 1H), 6.83 (dd, J = 8.8, 4.4 Hz, 1H), 6.69 (d, J = 4.8 Hz, 1H), 6.67 (s, 1H), 3.94-3.91 (m, 4H), 3.68 (d, J = 4.0 Hz, 2H), 3.25 (d, J = 16.0 Hz, 1H), 2.96-2.92 (m, 5H), 1.96-1.88 (m, 1H), 1.47 (s, 3H). LCMS (ESI): m/z = 431.2 [M + Na]$^+$. | and

| Ex. | Name | Structure | NMR, MS |
|---|---|---|---|
| 19 | N-[(2R)-2-(Hydroxymethyl)-2-methyl-6-morpholino-3H-benzofuran-5-yl]pyrrolo[1,2-b]pyridazine-7-carboxamide (absolute stereochemistry assigned arbitrarily) | | Example 19, Peak 2: $^1$H NMR (400 MHz, CDCl$_3$) δ 11.34 (s, 1H), 8.45 (s, 1H), 8.39-8.38 (m, 1H), 7.95 (d, J = 9.2 Hz, 1H), 7.82 (d, J = 4.4 Hz, 1H), 6.83 (dd, J = 8.8, 4.4 Hz, 1H), 6.69 (d, J = 4.8 Hz, 1H), 6.67 (s, 1H), 3.94-3.91 (m, 4H), 3.68 (d, J = 6.4 Hz, 2H), 3.25 (d, J = 15.6 Hz, 1H), 2.97-2.93 (m, 5H), 1.90 (t, J = 6.4 Hz, 1H), 1.47 (s, 3H). LCMS (ESI): m/z = 409.1 [M + H]$^+$. |

Preparation of Intermediate Pyrrolo[1,2-b]pyridazine-7-carboxylic acid (for Examples 18 and 19)

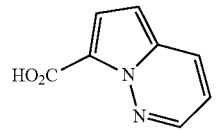

a. 2-Pyridazin-1-ium-1-ylpropanedinitrile

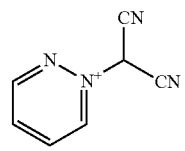 [SMILES: N#CC(C#N)[n+]1ccccn1]

To a solution of oxirane-2,2,3,3-tetracarbonitrile (2.0 g, 13.9 mmol) in tetrahydrofuran (30 mL) was added pyridazine (1.1 g, 13.7 mmol) at 0° C. under the nitrogen and stirred at 0° C. for 8 h. The resulting precipitate was filtered, washed with tetrahydrofuran (10 mL) and dried to afford 2-pyridazin-1-ium-1-ylpropanedinitrile (1.1 g, 55%) as a green solid, which was directly used in the next step without purification.

b. 6-Trimethylsilylpyrrolo[1,2-b]pyridazine-7-carbonitrile

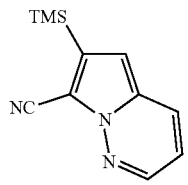 [SMILES: C[Si](C)(C)c1cc2cccnn2c1C#N]

To a solution of 2-pyridazin-1-ium-1-ylpropanedinitrile (1.1 g, 7.6 mmol) in toluene (5 mL) was added bis(trimethylsilyl)acetylene (1.3 g, 7.6 mmol), and the mixture was stirred at 110° C. for 48 h. The reaction was diluted with water (10 mL) and extracted with dichloromethane (10 mL×3). The combined organic phase was washed with brine (10 mL×3), dried over sodium sulfate, filtered and concentrated. The residue was purified by flash chromatography (eluting gradient: 0-30% ethyl acetate in petroleum ether) to afford 6-trimethylsilylpyrrolo[1,2-b]pyridazine-7-carbonitrile (600 mg, 39%) as a yellow solid. LCMS (ESI): m/z=215.9 [M+H]$^+$.

c. Pyrrolo[1,2-b]pyridazine-7-carbonitrile

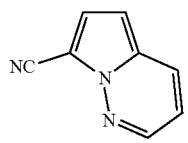 [SMILES: N#Cc1ccc2cccnn12]

To a solution of tetrabutylammonium fluoride (450 mg, 1.7 mmol) in tetrahydrofuran (5 mL) was added 6-trimethylsilylpyrrolo[1,2-b]pyridazine-7-carbonitrile (370 mg, 1.72 mmol) and stirred at 25° C. for 2 h. The reaction was diluted with water (10 mL) and extracted with dichloromethane (10 mL×3). The combined organic phase was washed with brine (10 mL×3), dried over sodium sulfate, filtered and concentrated. The residue was purified by flash chromatography (eluting gradient: 0-50% ethyl acetate in petroleum ether) to afford pyrrolo[1,2-b]pyridazine-7-carbonitrile (230 mg, 94%) as a white solid. $^1$H NMR (400 MHz, CDCl$_3$): δ 8.40-8.35 (m, 1H), 8.04 (dd, J 9.2, 1.6 Hz, 1H), 7.43 (d, J 4.8 Hz, 1H), 6.96 (dd, J 9.2, 4.4 Hz, 1H), 6.65 (d, J 4.4 Hz).

d. Pyrrolo[1,2-b]pyridazine-7-carboxylic acid

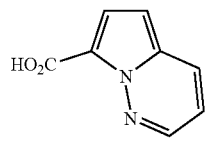 [SMILES: O=C(O)c1ccc2cccnn12]

To a solution of pyrrolo[1,2-b]pyridazine-7-carbonitrile (320 mg, 2.2 mmol) in ethanol (5 mL) and water (5 mL) was added sodium hydroxide (890 mg, 22.3 mmol). The reaction mixture was stirred at 100° C. for 72 h, after which it was diluted with water (10 mL) and extracted with dichloromethane (10 mL). The aqueous layer was acidified to pH=5 with 2 M hydrochloric acid and extracted with dichloromethane (10 mL×3). The combined organic phase was washed with brine (10 mL×3), dried over sodium sulfate, filtered and concentrated to afford pyrrolo[1,2-b]pyridazine-7-carboxylic acid (300 mg, 83%) as a gray solid, which was used without purification.

Example 20. N-(2,2-Dimethyl-6-morpholino-2,3-dihydrobenzofuran-5-yl)-1H-benzo[d]imidazole-4-carboxamide

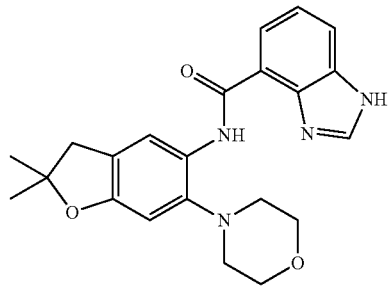 [SMILES: CC1(C)Cc2cc(NC(=O)c3cccc4[nH]cnc34)c(N3CCOCC3)cc2O1]

a. 1H-Benzo[d]imidazole-4-carbonyl chloride

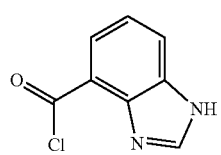 [SMILES: O=C(Cl)c1cccc2[nH]cnc12]

To a stirred solution of 1H-benzimidazole-4-carboxylic acid (200.0 mg, 1.2 mmol) in tetrahydrofuran (5 mL) was added thionyl chloride (0.6 mL, 8.3 mmol) and two drops of N,N-dimethylformamide. The mixture was stirred at 50° C. for 2 h under nitrogen and concentrated to give crude 1H-benzimidazole-4-carbonyl chloride (220 mg, 99%) as a white solid, which was used in next step directly without purification.

b. N-(2,2-Dimethyl-6-morpholino-2,3-dihydrobenzofuran-5-yl)-1H-benzo[d]imidazole-4-carboxamide

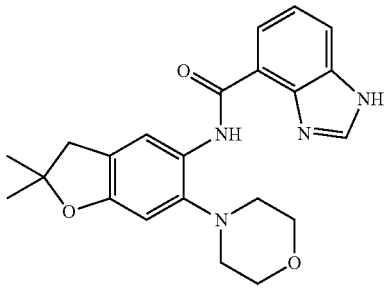

To a stirred solution of 2,2-dimethyl-6-morpholino-3H-benzofuran-5-amine (100 mg, 0.4 mmol) in dichloromethane (6 mL) was added 1H-benzimidazole-4-carbonyl chloride (80 mg, 0.4 mmol) and N,N-diisopropylethylamine (156 mg, 1.2 mmol). The mixture was stirred at 35° C. for 2 h under nitrogen and concentrated. The residue was purified by preparative HPLC (acetonitrile 40-70%/0.05% ammonium hydroxide in water) to give N-(2,2-dimethyl-6-morpholino-3H-benzofuran-5-yl)-1H-benzimidazole-4-carboxamide (118 mg, 74%) as a light brown solid. $^1$H NMR (400 MHz, CD$_3$OD) δ 8.39 (s, 1H), 8.19 (s, 1H), 8.11-8.03 (m, 1H), 7.82-7.74 (m, 1H), 7.42 (t, J=7.6 Hz, 1H), 6.63 (s, 1H), 3.90 (br s, 4H), 3.04 (s, 2H), 2.91 (t, J=4.4 Hz, 4H), 1.46 (s, 6H). LCMS (ESI): m/z=393.0 [M+H]$^+$.

The following compounds were made in a manner similar to that described for Example 20.

| Ex. | Name | Structure | NMR, MS |
|---|---|---|---|
| 21 | N-(2,2-Dimethyl-6-morpholino-2,3-dihydrobenzofuran-5-yl)-3H-imidazo[4,5-c]pyridine-7-carboxamide | 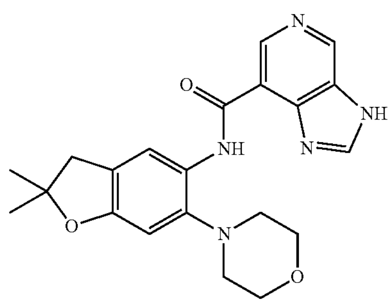 [SMILES: CC1(C)Cc2cc(NC(=O)c3cncc4[nH]cnc34)c(N3CCOCC3)cc2O1] | $^1$H NMR (400 MHz, CDCl$_3$) δ 9.18 (br s, 2H), 8.36-8.32 (m, 2H), 6.69 (s, 1H), 3.98-3.90 (m, 4H), 3.05 (s, 2H), 2.96-2.88 (m, 4H), 1.50 (s, 6H). LCMS (ESI): m/z = 394.2 [M + H]$^+$. |
| 22 | N-(2,2-Dimethyl-6-morpholino-2,3-dihydrobenzofuran-5-yl)-6-(trifluoromethyl)picolinamide | 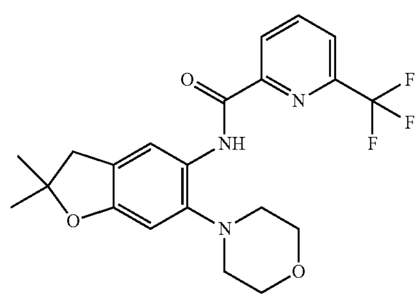 [SMILES: CC1(C)Cc2cc(NC(=O)c3cccc(C(F)(F)F)n3)c(N3CCOCC3)cc2O1] | $^1$H NMR (400 MHz, CDCl$_3$) δ 10.98 (s, 1H), 8.51 (d, J = 8.0 Hz, 1H), 8.44 (s, 1H), 8.13 (t, J = 8.0 Hz, 1H), 7.87 (d, J = 7.6 Hz, 1H), 6.68 (s, 1H), 3.95 (t, J = 4.8 Hz, 4H), 3.05 (s, 2H), 2.90 (t, J = 4.8 Hz, 4H), 1.50 (s, 6H). LCMS (ESI): m/z = 422.0 [M + H]$^+$. |
| 23 | N-[(2S)-2-(Hydroxymethyl)-2-methyl-6-morpholino-3H-benzofuran-5-yl]pyrrolo[2,1-f][1,2,4]triazine-7-carboxamide | 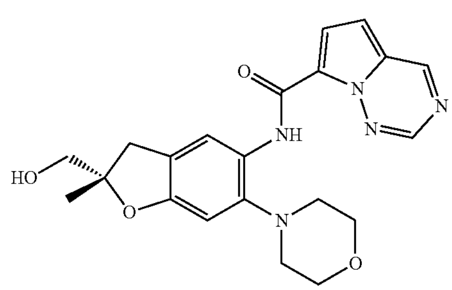 [SMILES: C[C@@]1(CO)Cc2cc(NC(=O)c3ccc4cncnn34)c(N3CCOCC3)cc2O1] | Example 23, Peak 1: $^1$H NMR (400 MHz, CDCl$_3$) δ 11.20 (s, 1H), 9.11 (s, 1H), 8.77 (s, 1H), 8.42 (s, 1H), 7.81 (d, J = 4.8 Hz, 1H), 6.99 (d, J = 4.8 Hz, 1H), 6.67 (s, 1H), 3.91 (t, J = 4.4 Hz, 4H), 3.68-3.63 (m, 2H), 3.24 (d, J = 15.6 Hz, 1H), 2.95-2.85 (m, 5H), 1.99 (t, J = 6.4 Hz, 1H), 1.45 (s, 3H). LCMS (ESI): m/z = 410.2 [M + H]$^+$. |

| Ex. | Name | Structure | NMR, MS |
|---|---|---|---|
| | and | | |
| 24 | N-[(2R)-2-(Hydroxymethyl)-2-methyl-6-morpholino-3H-benzofuran-5-yl]pyrrolo[2,1-f][1,2,4]triazine-7-carboxamide (absolute stereochemistry assigned arbitrarily) | 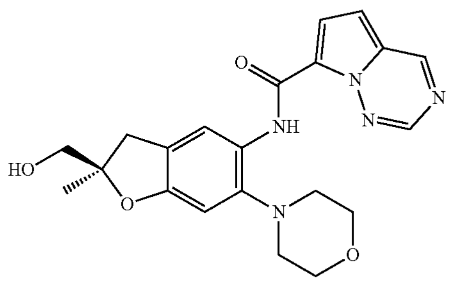 [SMILES: C[C@]1(CO)Cc2cc(NC(=O)c3ccc4cncnn34)c(N3CCOCC3)cc2O1] | Example 24, Peak 2: $^1$H NMR (400 MHz, CDCl$_3$) δ 11.23 (s, 1H), 9.13 (s, 1H), 8.79 (s, 1H), 8.44 (s, 1H), 7.83 (d, J = 4.8 Hz, 1H), 7.02 (d, J = 4.8 Hz, 1H), 6.69 (s, 1H), 3.94 (t, J = 4.0 Hz, 4H), 3.68-3.64 (m, 2H), 3.27 (d, J = 15.6 Hz, 1H), 2.98-2.88 (m, 5H), 2.06 (br s, 1H), 1.47 (s, 3H). LCMS (ESI): m/z = 410.2 [M + H]$^+$. |

Intermediate Pyrrolo[2,1-f][1,2,4]triazine-7-carboxylic acid (for Examples 23 and 24)

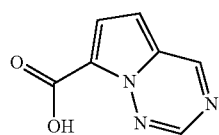 [SMILES: O=C(O)c1ccc2cncnn12]

a. Ethyl 1-amino-5-formyl-pyrrole-2-carboxylate

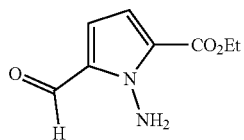 [SMILES: CCOC(=O)c1ccc(C=O)n1N]

To a mixture of ammonium chloride (6.34 g, 118 mmol) in diethyl ether (210 mL) at −20° C. was added concentrated ammonia solution (9.66 mL, 71.8 mmol), followed by sodium hypochlorite (10% by mass; 76.2 mL, 102 mmol) via a constant pressure dropping funnel. The mixture was stirred at −10° C. for 30 min. After separation, the organic layer was washed with brine that was pre-cooled to 0° C., and dried over anhydrous calcium chloride at −40° C. for 1 h before use.

In a separate flask, ethyl 5-formyl-1H-pyrrole-2-carboxylate (3.0 g, 18.0 mmol) was dissolved in N,N-dimethylformamide (30 mL), and brought to 0° C. in an ice bath. Sodium hydride (860 mg, 21.5 mmol) was added in portions and the mixture was stirred for 1 h at 25° C. The above mentioned chloramine solution in diethyl ether was added in one portion, and the mixture was stirred at 25° C. for 16 h under nitrogen. The reaction mixture was quenched with saturated aqueous sodium thiosulfate (10 mL) at 0° C. and diluted with water (20 mL). The diethyl ether layer was separated, and the aqueous layer was extracted once with ethyl acetate (100 mL). The organic layers were combined, washed with water (10 mL×4), dried over anhydrous sodium sulfate, and concentrated under reduced pressure to afford ethyl 1-amino-5-formyl-pyrrole-2-carboxylate (3.3 g, crude) as a light yellow solid, which was used without further purification. LCMS (ESI): m/z=182.9 [M+H]$^+$.

b. Ethyl pyrrolo[2,1-f][1,2,4]triazine-7-carboxylate

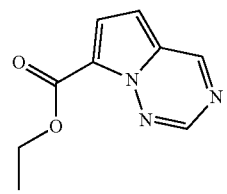

To a solution of ethyl 1-amino-5-formyl-pyrrole-2-carboxylate (3.3 g, 18 mmol) in ethanol (100 mL) was added formamidinium acetate (9.4 g, 91 mmol). The reaction mixture was stirred at 85° C. for 2 h under nitrogen, after which it was concentrated, diluted with water (20 mL) and extracted with dichloromethane (100 mL×3). The combined organic phase was washed with brine (10 mL×2), dried over sodium sulfate, filtered and concentrated. The residue was purified by flash chromatography (eluting gradient: 0-16% ethyl acetate in petroleum ether) to afford ethyl pyrrolo[2,1-J][1,2,4]triazine-7-carboxylate (1.1 g, 32%) as a red solid. $^1$H NMR (400 MHz, CDCl$_3$): δ 9.09 (s, 1H), 8.74 (s, 1H), 7.56 (d, J 4.8 Hz, 1H), 6.87 (d, J 5.2 Hz, 1H), 4.46 (q, J 7.2 Hz, 2H), 1.42 (t, J 7.2 Hz, 3H). LCMS (ESI): m/z=191.9 [M+H]$^+$.

c. Pyrrolo[2,1-f][1,2,4]triazine-7-carboxylic acid

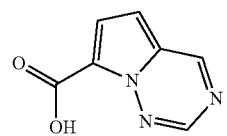 [SMILES: O=C(O)c1ccc2cncnn12]

To a solution of ethyl pyrrolo[2,1-J][1,2,4]triazine-7-carboxylate (500 mg, 2.6 mmol) in tetrahydrofuran (20 mL), methanol (5 mL) and water (10 mL) was added lithium hydroxide monohydrate (165 mg, 3.92 mmol). The reaction mixture was stirred at 25° C. for 2 h, after which it was concentrated and acidified with 1 M hydrochloric acid to pH=4-5. The resulting precipitate was filtered, washed with water (10 mL) and petroleum ether (20 mL), and dried to afford pyrrolo[2,1-J][1,2,4]triazine-7-carboxylic acid (360 mg, 84%) as a light yellow solid. $^1$H NMR (400 MHz, DMSO-d$_6$): δ 13.03 (br s, 1H), 9.34 (s, 1H), 8.77 (s, 1H), 7.52 (d, J 4.8 Hz, 1H), 7.03 (d, J 4.4 Hz, 1H). LCMS (ESI): m/z=163.9 [M+H]$^+$.

Example 25. N-(2,2-Dimethyl-6-morpholino-2,3-dihydrobenzofuran-5-yl)-2-methyl-3H-imidazo[4,5-c]pyridine-7-carboxamide

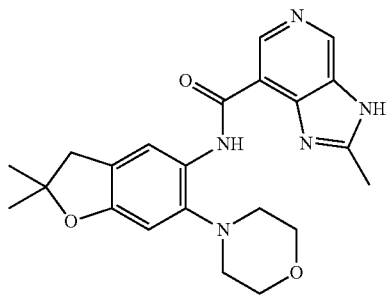

a. Ethyl 4-amino-5-nitronicotinate

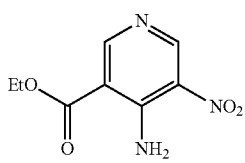 [SMILES: CCOC(=O)c1cncc([N+](=O)[O-])c1N]

To a solution of 4-aminonicotinic acid (5.0 g, 36 mmol) in sulfuric acid (50 mL) was added potassium nitrate (3.7 g, 37 mmol). The reaction mixture was stirred at 30° C. for 20 min and 75° C. for 3 h. Upon cooling to room temperature, ethanol (20 mL) was added, and the resulting mixture was stirred at 60° C. for 18 h. The mixture was brought to room temperature and slowly added to ice cold aqueous potassium acetate. Sodium bicarbonate was added to adjust to pH=8, and the mixture was extracted with ethyl acetate (300 mL). The organic phase was dried over sodium sulfate and concentrated. The residue was purified by silica gel chromatography (eluting gradient: 0-10% ethyl acetate in petroleum ether) to give ethyl 4-amino-5-nitronicotinate (2.9 g, 38%) as a yellow solid. $^1$H NMR (400 MHz, CDCl$_3$): δ 9.30 (s, 1H), 9.05 (s, 1H), 4.41 (q, J 7.2 Hz, 2H), 1.43 (t, J 7.2 Hz, 3H).

b. Ethyl 4,5-diaminonicotinate

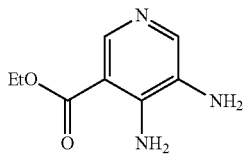

To a solution of ethyl 4-amino-5-nitronicotinate (2.0 g, 9.5 mmol) in ethanol (50 mL) was added palladium on carbon (10 wt %, 1.5 g, 1.42 mmol). The mixture was stirred at 30° C. for 12 h under H$_2$ (15 psi) and filtered. The filtrate was concentrated to afford ethyl 4,5-diaminonicotinate (1.6 g, 96% yield) as a white solid. $^1$H NMR (400 MHz, CDCl$_3$): δ 8.63 (s, 1H), 7.97 (s, 1H), 4.37 (q, J 7.2 Hz, 2H), 1.42 (t, J 7.2 Hz, 3H).

c. Ethyl 2-methyl-3H-imidazo[4,5-c]pyridine-7-carboxylate

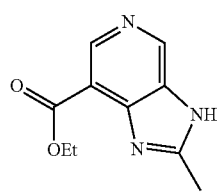

A solution of ethyl 4,5-diaminopyridine-3-carboxylate (100 mg, 0.55 mmol), triethyl orthoacetate (450 mg, 2.8 mmol) in acetic acid (1 mL) was stirred at 120° C. for 30 min. The reaction was diluted with water (20 mL) and extracted with dichloromethane (20 mL×2). The combined organic phase was dried over sodium sulfate and concentrated. The residue was purified by silica gel chromatography (eluting gradient: 0-5% methanol in dichloromethane) to afford ethyl 2-methyl-3H-imidazo[4,5-c]pyridine-7-carboxylate (80 mg, 71%) as a yellow solid. $^1$H NMR (400 MHz, CDCl$_3$): δ 9.11 (s, 1H), 8.97 (s, 1H), 4.50 (q, J=7.2 Hz, 2H), 2.72 (s, 3H), 1.48 (t, J=7.2 Hz, 3H).

d. 2-Methyl-3H-imidazo[4,5-c]pyridine-7-carboxylic acid

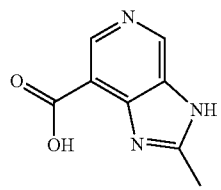

To a solution of ethyl 2-methyl-3H-imidazo[4,5-c]pyridine-7-carboxylate (80 mg, 0.39 mmol) in tetrahydrofuran (2 mL), water (2 mL) and methanol (1 mL) was added lithium hydroxide (18 mg, 0.78 mmol). The mixture was stirred at 30° C. for 12 h and concentrated to afford the crude title product, which was directly used without further purification.

e. N-(2,2-Dimethyl-6-morpholino-2,3-dihydrobenzofuran-5-yl)-2-methyl-3H-imidazo[4,5-c]pyridine-7-carboxamide

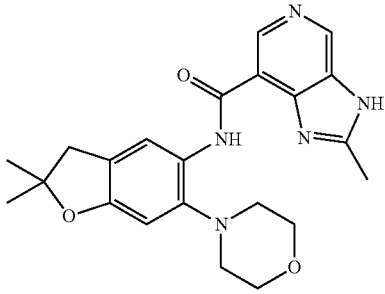

To a solution of 2,2-dimethyl-6-morpholino-3H-benzofuran-5-amine (483 mg, 1.95 mmol), (1-(bis(dimethylamino)methylene)-1H-1,2,3-triazolo[4,5-b]pyridinium 3-oxide hexafluorophosphate) (1.5 g, 3.89 mmol), and N,N-diisopropylethylamine (1.61 mL, 9.74 mmol) in N,N-dimethylformamide (10 mL) was added 2-methyl-3H-imidazo[4,5-c]pyridine-7-carboxylic acid (345 mg, 1.95 mmol). The reaction mixture was stirred at 30° C. for 12 h, after which it was diluted with water (100 mL) and extracted with dichloromethane (100 mL). The organic phase was washed with water (20 mL×2), dried over sodium sulfate and concentrated. The residue was purified by silica gel chromatography (eluting gradient: 0-5% methanol in dichloromethane) to afford N-(2,2-dimethyl-6-morpholino-2,3-dihydrobenzofuran-5-yl)-2-methyl-3H-imidazo[4,5-c]pyridine-7-carboxamide (200 mg, 25%) as a yellow solid.
$^1$H NMR (400 MHz, DMSO-d$_6$): δ 11.37 (br s, 1H), 8.98 (s, 1H), 8.94 (s, 1H), 8.26 (s, 1H), 6.66 (s, 1H), 3.83 (t, J 4.0 Hz, 4H), 3.00 (s, 2H), 2.83 (t, J 4.0 Hz, 4H), 2.74 (s, 3H), 1.42 (s, 6H). LCMS (ESI): m/z=408.1 [M+H]$^+$.

The following compounds were made in a manner similar to that described for Example 25.

| Ex. | Name | Structure | NMR, MS |
|---|---|---|---|
| 26 | (S)-N-(2,2-Dimethyl-6-morpholino-2,3-dihydrobenzofuran-5-yl)-2-(3-methylmorpholino)oxazole-4-carboxamide | 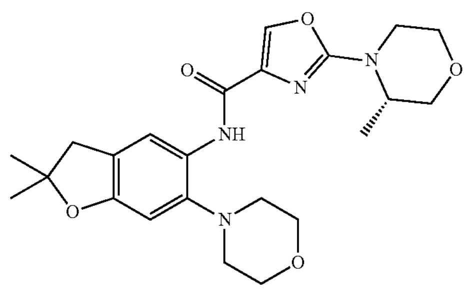 [SMILES: C[C@H]1COCCN1c1nc(C(=O)Nc2cc3c(cc2N2CCOCC2)OC(C)(C)C3)co1] | $^1$H NMR (400 MHz, CDCl$_3$): δ 9.76 (s, 1H), 8.32 (s, 1H), 7.83 (s, 1H), 6.60 (s, 1H), 4.13-3.98 (m, 2H), 3.92 (t, J = 4.4 Hz, 4H), 3.80-3.77 (m, 2H), 3.68-3.67 (m, 2H), 3.51-3.41 (m, 1H), 3.02 (s, 2H), 2.88 (t, J = 4.4 Hz, 4H), 1.48 (s, 6 H), 1.39 (d, J = 6.8 Hz, 3H). LCMS (ESI): m/z = 443.1 [M + H]$^+$. |
| 27 | N-(2,2-Dimethyl-6-morpholino-2,3-dihydrobenzofuran-5-yl)picolinamide | 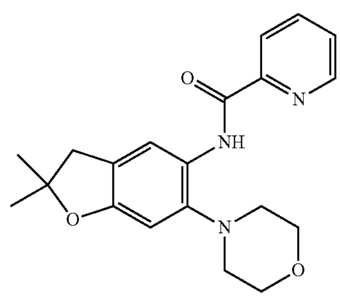 [SMILES: CC1(C)Cc2cc(NC(=O)c3ccccn3)c(N3CCOCC3)cc2O1] | 1H NMR (400 MHz, CDCl$_3$) δ 8.68-8.62 (m, 1H), 8.38 (s, 1H), 8.28 (d, J = 8.0 Hz, 1H), 7.90 (dt, J = 8.0, 1.6 Hz, 1H), 7.48-7.45 (m, 1H), 6.61 (s, 1H), 3.96 (t, J = 4.4 Hz, 4H), 3.03 (s, 2H), 2.91 (t, J = 4.4 Hz, 4H), 1.48 (s, 6H). LCMS (ESI): m/z = 354.1 [M + H]$^+$. |
| 28 | N-(2,2-Dimethyl-6-morpholino-3H-benzofuran-5-yl)-1H-pyrrolo[3,2-b]pyridine-3-carboxamide | 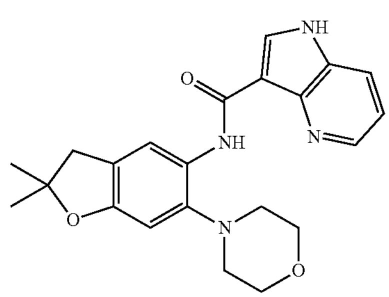 [SMILES: CC1(C)Cc2cc(NC(=O)c3c[nH]c4cccnc34)c(N3CCOCC3)cc2O1] | $^1$H NMR (400 MHz, DMSO-d$_6$) δ 12.09 (br s, 1H), 11.09 (s, 1H), 8.59 (d, J = 4.8 Hz, 1H), 8.32 (s, 1H), 8.28 (s, 1H), 7.96 (d, J = 8.4 Hz, 1H), 7.33 (dd, J = 8.4, 4.8 Hz, 1H), 6.66 (s, 1H), 3.86-3.84 (m, 4H), 2.99 (s, 2H), 2.83-2.81 (m, 4H), 1.41 (s, 6H). LCMS (ESI): m/z = 393.2 [M + H]$^+$. |

| Ex. | Name | Structure | NMR, MS |
|---|---|---|---|
| 29 | N-[2,2-Dimethyl-6-(5-methyl-2-pyridyl)-3H-benzofuran-5-yl]-2-methyl-oxazole-5-carboxamide | 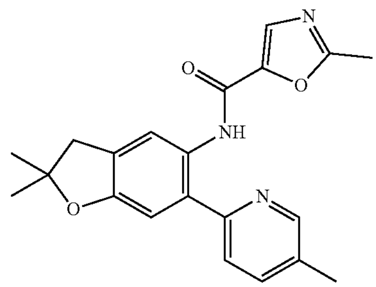 | $^1$H NMR (400 MHz, CDCl$_3$) δ 13.25 (s, 1H), 8.50 (s, 1H), 8.44 (s, 1H), 7.68-7.62 (m, 3H), 7.05 (s, 1H), 3.11 (s, 2H), 2.62 (s, 3H), 2.42 (s, 3H), 1.52 (s, 6H). LCMS (ESI): m/z = 364.1 [M + H]$^+$. |
| 30 | N-(2,2-Dimethyl-6-morpholino-2,3-dihydrobenzofuran-5-yl)thiophene-2-carboxamide | 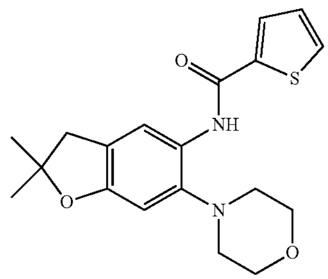 | $^1$H NMR (400 MHz, CD$_3$OD): δ 7.81 (m, 2H), 7.73 (d, J = 4.4 H, 1H), 7.22-7.20 (m, 1H), 6.63 (s, 1H), 3.84 (m, 4H), 3.02 (s, 2H), 2.87-2.88 (m, 1H), 1.45 (s, 6H). LCMS (ESI): m/z = 359 [M + H]$^+$. |
| 31 | N-(2,2-Dimethyl-6-morpholino-2,3-dihydrobenzofuran-5-yl)-5-methylfuran-2-carboxamide | 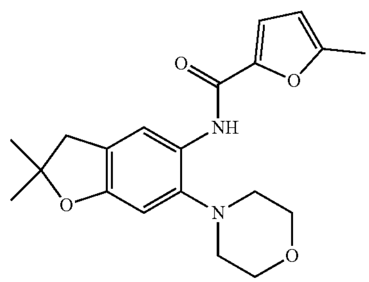 | $^1$H NMR (400 MHz, DMSO-d$_6$) δ 9.31 (s, 1H), 8.03 (s, 1H), 7.11 (d, J = 3.3 Hz, 1H), 6.70 (s, 1H), 6.34 (dd, J = 3.4, 1.2 Hz, 1H), 3.83-3.75 (m, 4H), 2.99 (d, J = 1.1 Hz, 2H), 2.84-2.77 (m, 4H), 2.41 (d, J = 0.9 Hz, 3H), 1.40 (s, 6H). LCMS (ESI): m/z = 357.1 [M + H]$^+$. |
| 32 | N-(2,2-Dimethyl-6-morpholino-2,3-dihydrobenzofuran-5-yl)-2-(3-methylmorpholino)thiazole-4-carboxamide | 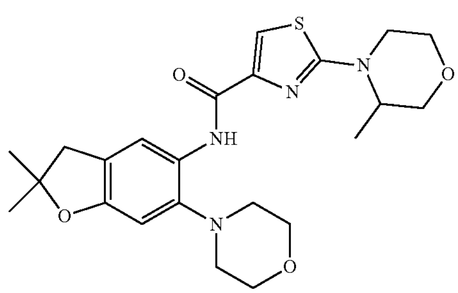 [SMILES: CC1COCCN1c1nc(C(=O)Nc2cc3c(cc2N2CCOCC2)OC(C)(C)C3)cs1] | $^1$H NMR (400 MHz, DMSO-d$_6$): δ 9.99 (s, 1H), 8.23 (s, 1H), 7.58 (s, 1H), 6.72 (s, 1H), 4.11-4.10 (m, 1H), 3.94 (d, J = 10.4 Hz, 1H), 3.78-3.73 (m, 5H), 3.63-3.58 (m, 2H), 3.43-3.42 (m, 1H), 2.99 (s, 2H), 2.78 (m, 4H), 1.41 (s, 6H), 1.31 (d, J = 6.8 Hz). LCMS (ESI): m/z = 459.2 [M + H]$^+$. |
| 33 | N-(2,2-Dimethyl-6-morpholino-2,3-dihydrobenzofuran-5-yl)-2-(4-methyl-1H-imidazol-1-yl)oxazole-4-carboxamide | 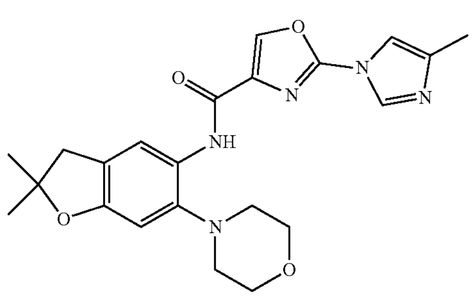 | $^1$H NMR (400 MHz, DMSO-d$_6$): δ 9.74 (s, 1H), 8.78 (s, 1H), 8.30 (d, J = 1.2 Hz, 1H), 8.18 (s, 1H), 7.50 (s, 1H), 6.74 (s, 1H), 3.86-3.84 (m, 4H), 3.02 (s, 2H), 2.84-2.81 (m, 4H), 2.22 (s, 2H), 1.42 (s, 6H). LCMS (ESI): m/z = 424.0 [M + H]$^+$. |

| Ex. | Name | Structure | NMR, MS |
|---|---|---|---|
| 34 | N-(2,2-Dimethyl-6-morpholino-2,3-dihydrobenzofuran-5-yl)-2-(pyrimidin-4-yl)oxazole-4-carboxamide | 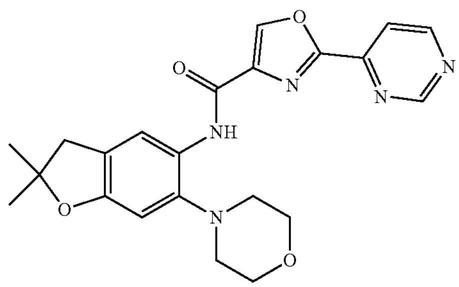 [SMILES: CC1(C)Cc2cc(NC(=O)c3coc(-c4ccncn4)n3)c(N3CCOCC3)cc2O1] | $^1$H NMR (400 MHz, DMSO-$d_6$): δ 9.93 (s, 1H), 9.42 (d, J = 1.2 Hz, 1H), 9.16 (d, J = 5.2 Hz, 1H), 9.09 (s, 1H), 8.20 (s, 12H), 8.16-8.14 (m, 1H), 6.78 (s, 1H), 3.90-3.87 (m, 4H), 3.03 (s, 2H), 2.86-2.84 (m, 4H), 1.43 (s, 6H). LCMS (ESI): m/z = 422.1 [M + H]$^+$. |
| 35 | N-(2,2-Dimethyl-6-morpholino-2,3-dihydrobenzofuran-5-yl)-2-(2-methylpyridin-4-yl)oxazole-4-carboxamide | 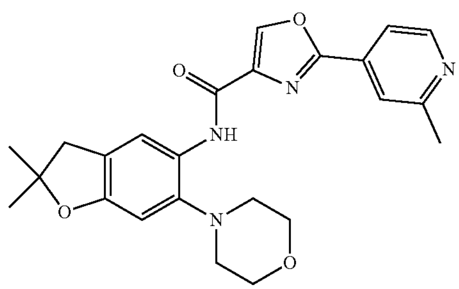 [SMILES: Cc1cc(-c2nc(C(=O)Nc3cc4c(cc3N3CCOCC3)OC(C)(C)C4)co2)ccn1] | $^1$H NMR (400 MHz, DMSO-$d_6$): δ 9.98 (s, 1H), 9.00 (s, 1H), 8.71 (d, J = 5.2 Hz, 1H), 8.18 (s, 1H), 7.84 (s, 1H), 7.75 (d, J = 4.8 Hz, 1H), 6.75 (s, 1H), 3.88-3.87 (m, 4H), 3.00 (s, 2H), 2.83-2.82 (m, 4H), 1.40 (s, 6H). LCMS (ESI): m/z = 435.1 [M + H]$^+$. |
| 36 | N-(2,2-Dimethyl-6-morpholino-2,3-dihydrobenzofuran-5-yl)-2-morpholinothiazole-4-carboxamide | 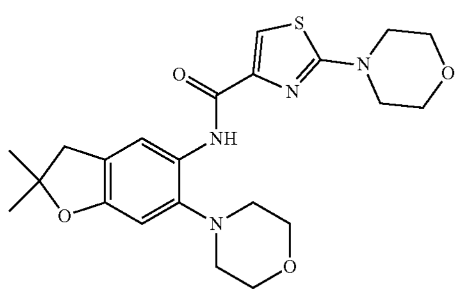 | $^1$H NMR (400 MHz, CD$_3$OD): δ 8.15 (s, 1H), 7.52 (s, 1H), 6.64 (s, 1H), 3.88-3.83 (m, 8H), 3.60-3.57 (m, 4H), 3.01 (s, 2H), 2.86-2.84 (m, 4H), 1.44 (s, 6H). LCMS (ESI): m/z = 445.1 [M + H]$^+$. |
| 37 | N-(2,2-Dimethyl-6-morpholino-2,3-dihydrobenzofuran-5-yl)-2-morpholinooxazole-4-carboxamide | 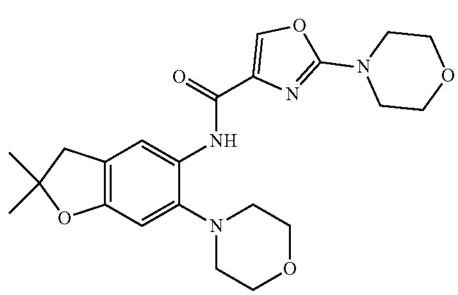 | $^1$H NMR (400 MHz, CD$_3$OD): δ 8.14 (s, 1H), 7.96 (s, 1H), 6.63 (s, 1H), 3.91-3.88 (m, 4H), 3.81-3.89 (m, 4H), 3.58-3.55 (m, 4H), 3.01 (s, 2H), 2.85-2.84 (m, 4H), 1.44 (s, 6H). LCMS (ESI): m/z = 429.0 [M + H]$^+$. |
| 38 | 2-Cyclopropyl-N-(2,2-dimethyl-6-morpholino-2,3-dihydrobenzofuran-5-yl)oxazole-4-carboxamide | 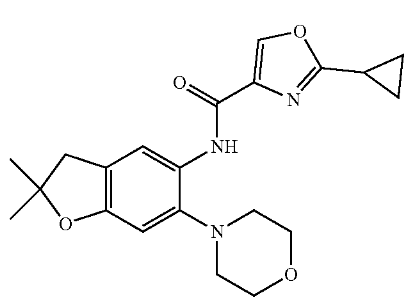 [SMILES: CC1(C)Cc2cc(NC(=O)c3coc(C4CC4)n3)c(N3CCOCC3)cc2O1] | $^1$H NMR (400 MHz, CD$_3$OD): δ 8.25 (s, 1H), 8.13 (s, 1H), 6.63 (s, 1H), 3.92-3.90 (m, 4H), 3.01 (s, 2H), 2.87-2.85 (m, 4H), 2.18 (m, 1H), 1.44 (s, 6H), 1.17-1.12 (m, 4H). LCMS (ESI): m/z = 384.2 [M + H]$^+$. |

| Ex. | Name | Structure | NMR, MS |
|---|---|---|---|
| 39 | 2-Bromo-N-(2,2-dimethyl-6-morpholino-2,3-dihydrobenzofuran-5-yl)oxazole-4-carboxamide | 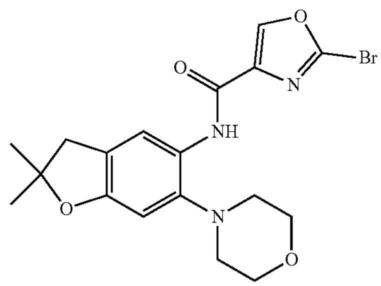 | $^1$H NMR (400 MHz, CD$_3$OD): δ 8.55 (s, 1H), 8.11 (s, 1H), 6.65 (s, 1H), 3.92-3.90 (m, 4H), 3.01 (s, 2H), 2.88-2.85 (m, 4H), 1.44 (s, 6H). LCMS (ESI): m/z = 429.1 [M + H]$^+$. |
| 40 | N-(2,2-Dimethyl-6-morpholino-2,3-dihydrobenzofuran-5-yl)-2-(hydroxymethyl)-1H-benzo[d]imidazole-4-carboxamide | 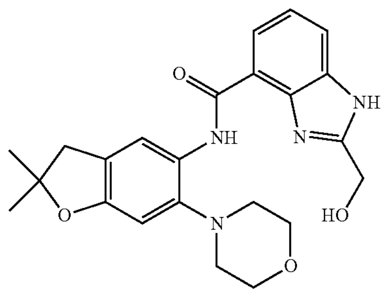 [SMILES: CC1(C)Cc2cc(NC(=O)c3cccc4[nH]c(CO)nc34)c(N3CCOCC3)cc2O1] | $^1$H NMR (400 MHz, DMSO-d$_6$): δ 12.91 (br. s, 1H), 11.67 (s, 1H), 8.21 (s, 1H), 7.96 (d, J = 7.2 Hz, 1H), 7.69 (d, J = 7.2 Hz, 1H), 7.36-7.32 (m, 1H), 4.92 (d, J = 5.2 Hz, 2H), 3.81-3.79 (m, 4H), 3.00 (s, 2H), 2.84-2.82 (m, 4H), 1.43 (s, 6H). LCMS (ESI): m/z = 423.1 [M + H]$^+$. |
| 41 | 2-(tert-Butyl)-N-(2,2-dimethyl-6-morpholino-2,3-dihydrobenzofuran-5-yl)oxazole-4-carboxamide | 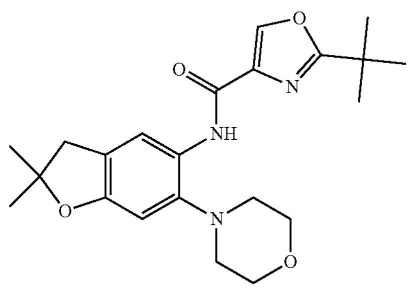 [SMILES: CC1(C)Cc2cc(NC(=O)c3coc(C(C)(C)C)n3)c(N3CCOCC3)cc2O1] | $^1$H NMR (400 MHz, CD$_3$OD): δ 8.33 (s, 1H), 8.17 (s, 1H), 6.65 (s, 1H), 3.94-3.92 (m, 4H), 3.02 (s, 2H), 2.88-2.86 (m, 4H), 1.46 (s, 9H), 1.44 (s, 6H). LCMS (ESI): m/z = 400.1 [M + H]$^+$. |
| 42 | N-(2,2-Dimethyl-6-morpholino-2,3-dihydrobenzofuran-5-yl)thiazole-4-carboxamide | 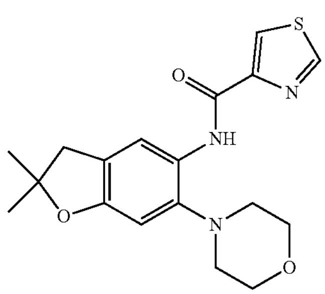 [SMILES: CC1(C)Cc2cc(NC(=O)c3cscn3)c(N3CCOCC3)cc2O1] | $^1$H NMR (400 MHz, CD$_3$OD): δ 9.11 (s, 1H), 8.34 (s, 1H), 8.19 (s, 1H), 6.65 (s, 1H), 3.93-3.91 (m, 4H), 3.04 (s, 2H), 2.89-2.88 (m, 4H), 1.45 (s, 6H). LCMS (ESI): m/z = 359.9 [M + H]$^+$. |
| 43 | N-(2,2-Dimethyl-6-morpholino-2,3-dihydrobenzofuran-5-yl)-5-ethyl-1H-imidazole-2-carboxamide | 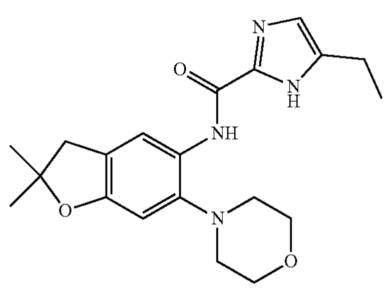 [SMILES: CCc1cnc(C(=O)Nc2cc3c(cc2N2CCOCC2)OC(C)(C)C3)[nH]1] | $^1$H NMR (400 MHz, CD$_3$OD): δ 8.04 (s, 1H), 7.01-6.89 (m, 1H), 6.63 (s, 1H), 3.92 (m, 4H), 3.02 (s, 2H), 2.86 (m, 4H), 2.68 (m, 2H), 1.45 (s, 6H), 2.93 (t, J = 7.6 Hz, 3H). LCMS (ESI): m/z = 371.1 [M + H]$^+$. |

| Ex. | Name | Structure | NMR, MS |
|---|---|---|---|
| 44 | N-(2,2-Dimethyl-6-morpholino-2,3-dihydrobenzofuran-5-yl)-5-methyl-1H-imidazole-2-carboxamide | 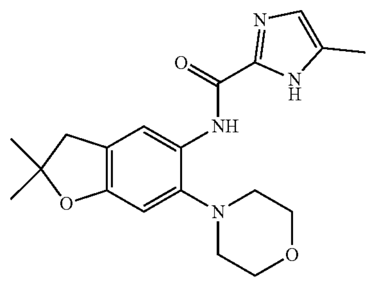 | $^1$H NMR (400 MHz, CD$_3$OD): δ 8.05 (s, 1H), 7.03-6.87 (m, 1H), 6.64 (s, 1H), 3.93 (m, 4H), 3.04 (s, 2H), 2.88 (m, 4H), 2.33-2.30 (m, 3H), 1.47 (s, 6H). LCMS (ESI): m/z = 357.0 [M + H]$^+$. |
| 45 | N-(2,2-Dimethyl-6-morpholino-2,3-dihydrobenzofuran-5-yl)-1H-pyrazolo[4,3-b]pyridine-3-carboxamide | 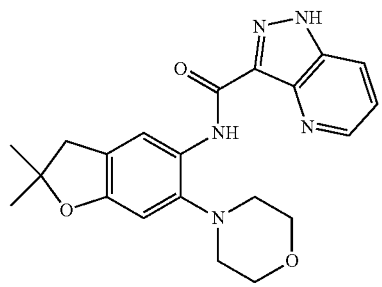 [SMILES: CC1(C)Cc2cc(NC(=O)c3n[nH]c4cccnc34)c(N3CCOCC3)cc2O1] | $^1$H NMR (400 MHz, DMSO-d$_6$): δ 11.07 (s, 1H), 8.78 (d, J = 4.8 Hz, 1H), 8.33 (s, 1H), 8.21 (d, J = 7.6 Hz, 1H), 7.55 (d, J = 8.4 Hz, 1H), 6.71 (s, 1H), 3.83 (m, 4H), 3.02 (s, 2H), 2.83 (m, 4H), 1.42 (s, 6H). LCMS (ESI): m/z = 394.2 [M + H]$^+$. |
| 46 | N-(2,2-Dimethyl-6-morpholino-2,3-dihydrobenzofuran-5-yl)pyrimidine-4-carboxamide | 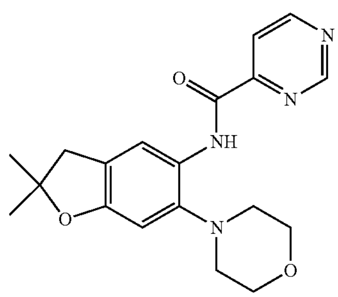 [SMILES: CC1(C)Cc2cc(NC(=O)c3ccncn3)c(N3CCOCC3)cc2O1] | $^1$H NMR (400 MHz, DMSO-d$_6$): δ 10.85 (s, 1H), 9.45 (s, 1H), 9.12 (d, J = 5.2 Hz, 1H), 8.25 (s, 1H), 8.13 (d, J = 4.8 Hz, 1H), 6.73 (s, 1H), 3.84-3.82 (m, 4H), 3.01 (s, 2H), 2.83-2.81 (m, 4H), 1.41 (s, 6H). LCMS (ESI): m/z = 354.9 [M + H]$^+$. |
| 47 | 5-(tert-Butyl)-N-(2,2-dimethyl-6-morpholino-2,3-dihydrobenzofuran-5-yl)-1H-imidazole-2-carboxamide | 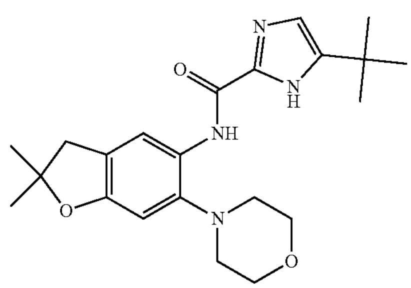 [SMILES: CC1(C)Cc2cc(NC(=O)c3ncc(C(C)(C)C)[nH]3)c(N3CCOCC3)cc2O1] | $^1$H NMR (400 MHz, CD$_3$OD): δ 8.08 (s, 1H), 7.00-6.96 (m, 1H), 6.62 (s, 1H), 3.93 (m, 4H), 3.01 (s, 2H), 2.87 (m, 4H), 1.44 (s, 6H), 1.35 (s, 9H). LCMS (ESI): m/z = 399.1 [M + H]$^+$. |
| 48 | N-(2,2-Dimethyl-6-morpholino-2,3-dihydrobenzofuran-5-yl)furan-2-carboxamide | 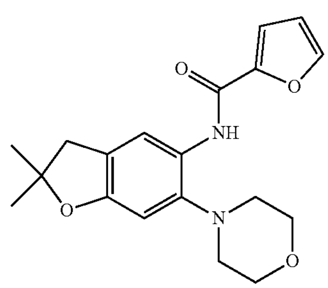 [SMILES: CC1(C)Cc2cc(NC(=O)c3ccco3)c(N3CCOCC3)cc2O1] | $^1$H NMR (400 MHz, CD$_3$OD): δ 8.02 (s, 1H), 7.77 (s, 1H), 7.21 (d, J = 3.6 Hz, 1H), 6.65 (s, 1H), 3.89-3.86 (m, 4H), 3.02 (s, 2H), 2.88-2.85 (m, 4H), 1.44 (s, 6H). LCMS (ESI): m/z = 342.9 [M + H]$^+$. |

| Ex. | Name | Structure | NMR, MS |
|---|---|---|---|
| 49 | 1-(2-Acetamido-4-pyridyl)-N-(2,2-dimethyl-6-morpholino-3H-benzofuran-5-yl)pyrazole-3-carboxamide | 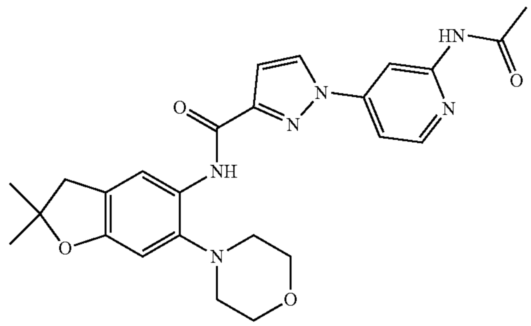 [SMILES: CC(=O)Nc1cc(-n2ccc(C(=O)Nc3cc4c(cc3N3CCOCC3)OC(C)(C)C4)n2)ccn1] | $^1$H NMR (400 MHz, DMSO-$d_6$): δ 10.76 (s, 1H), 9.79 (s, 1H), 8.79-8.79 (m, 1H), 8.72-8.72 (m, 1H), 8.47-8.46 (m, 1H), 8.19 (s, 1H), 7.68-7.66 (m, 1H), 7.09-7.09 (m, 1H), 6.72 (s, 1H), 3.84-3.82 (m, 4H), 3.02 (m, 2H), 2.82-2.80 (m, 4H), 2.14 (s, 3H), 1.41 (s, 6H). MS (ESI): m/z = 477.2 [M + 1]$^+$. |
| 50 | N-(2,2-Dimethyl-6-morpholino-3H-benzofuran-5-yl)-3-methyl-triazolo[4,5-c]pyridine-7-carboxamide | 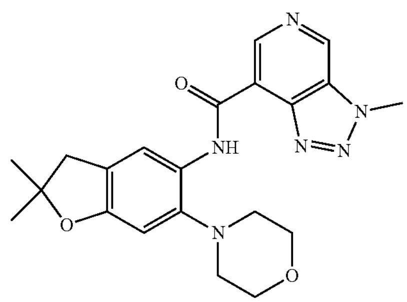 | $^1$H NMR (400 MHz, DMSO-$d_6$): δ 11.39 (s, 1H), 9.65 (s, 1H), 9.10 (s, 1H), 8.44 (s, 1H), 6.80 (s, 1H), 4.59 (s, 3H), 3.89 (s, 4H), 3.04 (s, 2H), 2.94-2.76 (m, 4H), 1.43 (s, 6H). MS (ESI): m/z = 409.2 [M + H]$^+$. |
| 51 | N-(2,2-Dimethyl-6-morpholino-3H-benzofuran-5-yl)-2-methyl-oxazole-4-carboxamide | 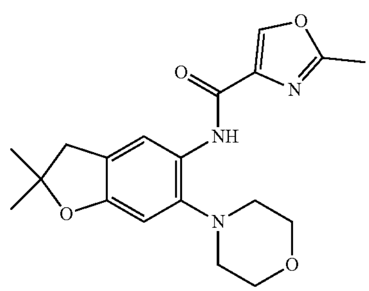 | $^1$H NMR (400 MHz, CDCl$_3$): δ 9.80 (s, 1H), 8.27 (s, 1H), 8.14 (s, 1H), 6.90 (s, 1H), 3.94-3.96 (t, 4H), 3.02 (s, 2H), 2.87-2.89 (t, 4H), 2.53 (s, 3H), 1.48 (s, 6H). MS (ESI): m/z = 358 [M + 1]$^+$. |
| 52 | N-(2-(Hydroxymethyl)-2-methyl-6-morpholino-2,3-dihydrobenzofuran-5-yl)-3-methyl-3H-[1,2,3]triazolo[4,5-c]pyridine-7-carboxamide | 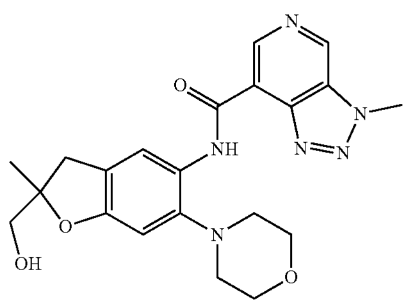 | $^1$H NMR (400 MHz, DMSO-$d_6$): δ 11.39 (s, 1H), 9.65 (s, 1H), 9.10 (s, 1H), 8.43 (s, 1H), 6.79 (s, 1H), 5.07 (t, J = 5.8 Hz, 2H), 4.59 (s, 3H), 3.89 (s, 4H), 3.53-3.38 (m, 2H), 3.24 (d, J = 16.2 Hz, 1H), 2.94-2.77 (m, 4H), 1.36 (s, 3H). MS (ESI): m/z = 425.2 [M + 1]$^+$. |
| 53 | N-(2,2-Dimethyl-6-morpholino-3H-benzofuran-5-yl)-3-ethyl-triazolo[4,5-c]pyridine-7-carboxamide | 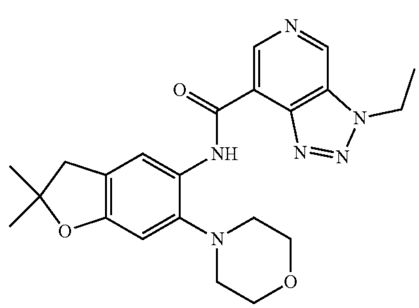 [SMILES: CCn1nnc2c(C(=O)Nc3cc4c(cc3N3CCOCC3)OC(C)(C)C4)cncc21] | $^1$H NMR (400 MHz, DMSO-$d_6$): δ 11.40 (s, 1H), 9.71 (s, 1H), 9;.10 (s, 1H), 8.45 (s, 1H), 6.80 (s, 1H), 5.03 (q, J = 7.4 Hz, 2H), 3.94-3.85 (m, 2H), 3.04 (s, 1H), 2.93-2.75 (m, 2H), 1.64 (t, J = 7.3 Hz, 2H). MS (ESI): m/z = 423.2 [M + 1]$^+$. |

| Ex. | Name | Structure | NMR, MS |
|---|---|---|---|
| 54 | N-[2-(Hydroxymethyl)-2-methyl-6-morpholino-3H-benzofuran-5-yl]-6,6-dimethyl-5,7-dihydropyrazolo[5,1-b][1,3]oxazine-2-carboxamide | 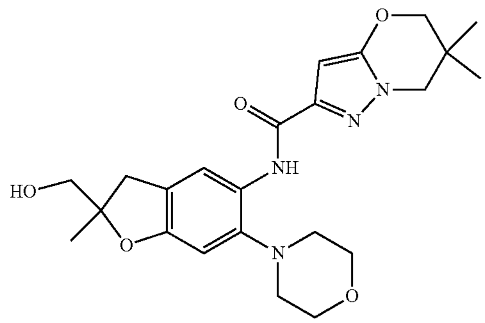 [SMILES: CC1(C)COc2cc(C(=O)Nc3cc4c(cc3N3CCOCC3)OC(C)(CO)C4)nn2C1] | $^1$H NMR (400 MHz, DMSO-$d_6$): δ 9.72 (s, 1H), 8.13 (s, 1H), 6.67 (s, 1H), 5.97 (s, 1H), 5.04 (t, J = 5.6 Hz, 1H), 4.02 (s, 2H), 3.97 (s, 2H), 3.81 (t, J = 4.4 Hz, 4H), 3.47-3.38 (m, 2H), 3.18 (d, J = 16 Hz, 1H), 2.86-2.74 (m, 5H), 1.33 (s, 3H), 1.08 (s, 6H). MS (ESI): m/z = 443.2 [M + 1]$^+$. |
| 55 | N-[2-(Hydroxymethyl)-2-methyl-6-morpholino-3H-benzofuran-5-yl]-6-methyl-6,7-dihydro-5H-pyrazolo[5,1-b][1,3]oxazine-3-carboxamide | 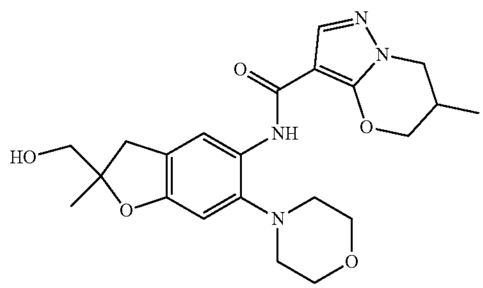 [SMILES: CC1COc2c(C(=O)Nc3cc4c(cc3N3CCOCC3)OC(C)(CO)C4)cnn2C1] | $^1$H NMR (400 MHz, CDCl$_3$): δ 9.71 (s, 1H), 8.29 (s, 1H), 6.60 (s, 1H), 6.09 (s, 1H), 4.29 (m, 2H), 3.95-3.90 (t, 5H), 3.81-3.75 (m, 1H) 3.65 (s, 2H), 3.24-3.20 (m, 1H), 2.94-2.87 (m, 5H), 2.51-2.55 (s, 1H), 1.45 (s, 3H), 1.16-1.18 (d, 3H). MS (ESI): m/z = 429.2 [M + 1]$^+$. |

Examples 56 and 57. (R)-6-Chloro-N-(2-(hydroxymethyl)-2-methyl-6-morpholino-2,3-dihydrobenzofuran-5-yl)thieno[3,2-b]pyridine-3-carboxamide and (S)-6-Chloro-N-(2-(hydroxymethyl)-2-methyl-6-morpholino-2,3-dihydrobenzofuran-5-yl)thieno[3,2-b]pyridine-3-carboxamide

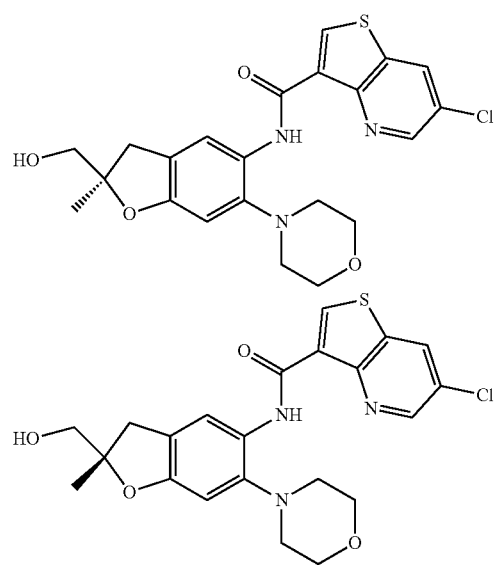

A mixture of the title compounds (60 mg, 26%) was made in a manner analogous to Example 25 as an off-white solid. Upon chiral resolution (R)-6-chloro-N-(2-(hydroxymethyl)-2-methyl-6-morpholino-2,3-dihydrobenzofuran-5-yl)thieno[3,2-b]pyridine-3-carboxamide and (S)-6-chloro-N-(2-(hydroxymethyl)-2-methyl-6-morpholino-2,3-dihydrobenzofuran-5-yl)thieno[3,2-b]pyridine-3-carboxamide were isolated as solids with absolute stereochemistry assigned arbitrarily.

Example 56, peak 1: $^1$H NMR (400 MHz, dimethyl sulfoxide-$d_6$): δ 11.49 (s, 1H), 8.99 (s, 1H), 8.95-8.91 (m, 2H), 8.22 (s, 1H), 6.68 (s, 1H), 3.79-3.77 (m, 4H), 3.45-3.43 (m, 2H), 3.32 (m, 1H), 2.83-2.81 (m, 5H), 1.35 (s, 3H). MS (ESI): m/z=460.1 [M+1]$^+$.

Example 57, peak 2: $^1$H NMR (400 MHz, dimethyl sulfoxide-$d_6$): δ 11.49 (s, 1H), 8.99 (s, 1H), 8.95-8.91 (m, 2H), 8.22 (s, 1H), 6.68 (s, 1H), 3.79-3.77 (m, 4H), 3.45-3.43 (m, 2H), 3.32 (m, 1H), 2.83-2.81 (m, 5H), 1.35 (s, 3H). MS (ESI): m/z=460.1 [M+1]$^+$.

Preparation of Intermediate 2-(tert-Butyl)-1H-imidazole-4-carboxylic acid (for Example 47)

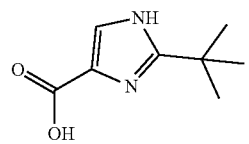

a. Ethyl 2-(tert-butyl)-1H-imidazole-4-carboxylate

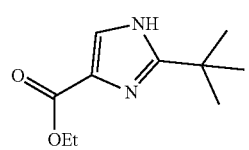

To a mixture of ethyl 1H-imidazole-4-carboxylate (1.0 g, 7.1 mmol), 2,2-dimethylpropanoic acid (2.5 mL, 21 mmol), silver nitrate (730 mg, 4.3 mmol), sulfuric acid (5 mL) in water (45 mL) was added a solution of ammonium persulfate (4.9 g, 21 mmol) in water (15 mL). The mixture was then heated to 75° C. for 30 min. The reaction mixture was cooled to 10° C. and slowly added to ammonia in water (30%, 200 mL). The mixture was extracted with ethyl acetate (30 mL×3). The organic phase was evaporated under reduced pressure, and the residue was purified by silica gel column (eluting with 50% ethyl acetate in petroleum ether). Ethyl 2-tert-butyl-1H-imidazole-4-carboxylate (300 mg, 6% yield) was obtained as a white solid. $^1$H NMR (400 MHz, CDCl$_3$): δ 9.52 (m, 1H), 7.54 (s, 1H), 7.20 (s, 1H), 4.27 (q, J=7.2 Hz, 2H), 1.34 (s, 9H), 1.30 (t, J=7.2 Hz, 3H).

b. 2-(tert-Butyl)-1H-imidazole-4-carboxylic acid

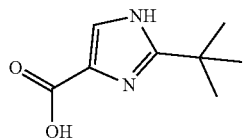

To a solution of ethyl 2-tert-butyl-1H-imidazole-4-carboxylate (200 mg, 1.0 mmol) in tetrahydrofuran (2.0 mL) was added sodium hydroxide (82 mg, 2.0 mmol) in water (2.0 mL). The mixture was stirred at 50° C. for 12 h. The reaction mixture was evaporated under reduced pressure to remove tetrahydrofuran (2.0 mL), and the mixture was adjusted to pH=6 with 2 M hydrochloric acid. The resulting precipitate was collected by filtration. 2-tert-Butyl-1H-imidazole-4-carboxylic acid (60 mg, 35% yield) was obtained as a yellow solid. $^1$H NMR (400 MHz, DMSO-d$_6$): δ 7.91 (s, 1H), 1.37 (s, 9H).

Preparation of Intermediate
4-Ethyl-1H-imidazole-2-carboxylic acid (for Example 43)

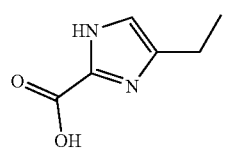

a. Ethyl 4-vinyl-1H-imidazole-2-carboxylate

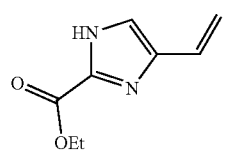

A mixture of ethyl 4-bromo-1H-imidazole-2-carboxylate (500 mg, 2.3 mmol), 4,4,5,5-tetramethyl-2-vinyl-1,3,2-dioxaborolane (700 mg, 4.6 mmol), 1,1'-bis(diphenylphosphino)ferrocene-palladium(II)dichloride (170 mg) and cesium carbonate (820 mg, 2.5 mmol) in 1,4-dioxane (2.0 mL) and water (2.0 mL) was heated to 85° C. for 8 h. The mixture was filtered, and the filtrate was evaporated under reduced pressure. The residue was purified by silica-gel column chromatography (eluting gradient: 15:1 to 1:1 petroleum ether: ethyl acetate). Ethyl 4-vinyl-1H-imidazole-2-carboxylate (160 mg, 38% yield) was obtained as a colorless oil. LCMS (ESI): m/z=167.1 [M+H]$^+$.

b. Ethyl 4-ethyl-1H-imidazole-2-carboxylate

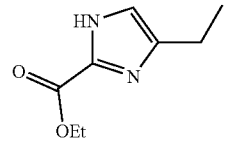

A mixture of ethyl 4-vinyl-1H-imidazole-2-carboxylate (160 mg, 0.96 mmol) and palladium on carbon (58 mg) in ethanol (5.0 mL) was stirred at 12° C. for 12 h under hydrogen (15 psi). The mixture was filtered, and the filtrate was evaporated under reduced pressure. Ethyl 4-ethyl-1H-imidazole-2-carboxylate (80 mg, 0.48 mmol, 49% yield) was obtained as a colorless oil and was used without purification. $^1$H NMR (400 MHz, CDCl$_3$): δ 6.89 (d, J 21 Hz, 1H), 4.45-4.39 (m, 2H), 2.72-2.67 (m, 2H), 1.41 (t, J 5.6 Hz, 3H), 1.37-1.24 (m, 3H).

c. 4-Ethyl-1H-imidazole-2-carboxylic acid

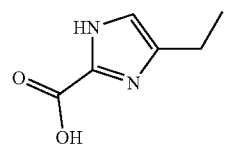

The title compound was prepared in an analogous manner to Intermediate 2-(tert-Butyl)-1H-imidazole-4-carboxylic acid, Step b to afford 4-ethyl-1H-imidazole-2-carboxylic acid (50 mg crude) as a white solid. LCMS (ESI): m/z=141.2 [M+H]$^+$.

Preparation of Intermediate
4-(tert-Butyl)-1H-imidazole-2-carboxylic acid

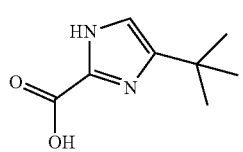

a. Ethyl 4-(tert-butyl)-1H-imidazole-2-carboxylate

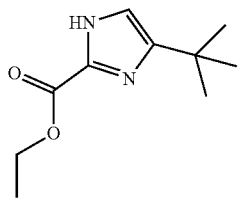

A solution of 2,2-dimethylpropanoic acid (4.91 mL, 42.8 mmol) and silver nitrate (1.45 g, 8.56 mmol) in a mixture of sulfuric acid (5.43 mL, 102 mmol) in water (180 mL) was degassed and purged with nitrogen for 3 times. Ethyl 1H-imidazole-2-carboxylate (2.00 g, 14.3 mmol) was added to the mixture. A solution of ammonium persulfate (9.77 g, 42.8 mmol) in water (50 mL) was added to the mixture. The reaction mixture was stirred at 75° C. for 30 min under nitrogen. The reaction was terminated by pouring it onto ice. The resulting mixture was made alkaline with 30% ammonium hydroxide solution (200 mL), and extracted with DCM (200 mL×3). The combined extracts were washed with brine (300 mL), stirred with saturated aqueous sodium sulfite (300 mL) for 30 min. The layers were separated, and the organic layer was dried with anhydrous sodium sulfate, filtered and concentrated under reduced pressure to give a residue. The residue was purified by silica gel chromatography (eluting gradient: petroleum ether: ethyl acetate=20:1 to 0:1). Ethyl 4-tert-butyl-1H-imidazole-2-carboxylate (200 mg, 5.71% yield) was obtained as a yellow oil. LCMS (ESI): m/z=197.1 [M+H]$^+$.

b. 4-(tert-Butyl)-1H-imidazole-2-carboxylic Acid

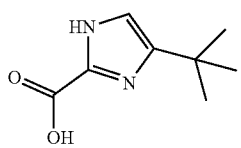

The title compound was prepared in an analogous manner to Intermediate 2-(tert-Butyl)-1H-imidazole-4-carboxylic acid, Step b to afford 4-tert-butyl-1H-imidazole-2-carboxylic acid (100 mg, crude) as a white solid. $^1$H NMR (400 MHz, DMSO-d$_6$): δ 7.49 (s, 1H), 1.38 (s, 9H).

Preparation of Intermediate 7-Hydroxypyrazolo[1,5-a]pyrimidine-3-carboxylic Acid

a. Ethyl 7-hydroxypyrazolo[1,5-a]pyrimidine-3-carboxylate

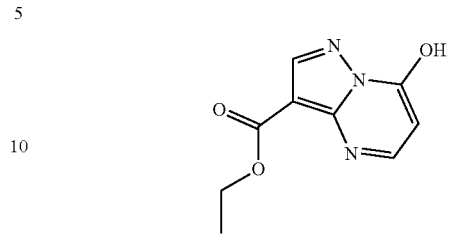

A mixture of ethyl 5-amino-1H-pyrazole-4-carboxylate (3.50 g, 22.6 mmol), ethyl 3,3-diethoxypropanoate (5.26 mL, 27.1 mmol) in acetic acid (20 mL) was degassed and purged with nitrogen for three times, and then the mixture was stirred at 100° C. for 2 h under nitrogen. The mixture was filtered and concentrated under reduced pressure to give a residue. The residue was purified by silica gel column chromatography (eluting gradient: petroleum ether/ethyl acetate=20:1 to 0:1). Ethyl 7-hydroxypyrazolo[1,5-a]pyrimidine-3-carboxylate (500 mg, 2.17 mmol, 9.63% yield) was obtained as a yellow solid.

b. 7-Hydroxypyrazolo[1,5-a]pyrimidine-3-carboxylic Acid

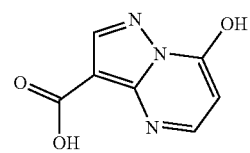 [SMILES: O=C(O)c1cnn2c(O)ccnc12]

The title compound was prepared in an analogous manner to Intermediate 2-(tert-Butyl)-1H-imidazole-4-carboxylic acid, Step b to afford 7-hydroxypyrazolo[1,5-a]pyrimidine-3-carboxylic acid (250 mg) was obtained as a white solid. The product was used without purification. $^1$H NMR (400 MHz, DMSO-d$_6$): δ 8.17 (s, 1H), 7.80 (d, J 7.2 Hz, 1H), 5.89 (d, J 7.2 Hz, 1H). LCMS (ESI): m/z=180.1 [M+H]$^+$.

Preparation of Intermediate 2-(Hydroxymethyl)-1H-benzo[d]imidazole-4-carboxylic Acid

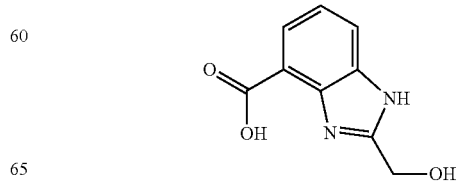

a. Methyl 3-(2-acetoxyacetamido)-2-aminobenzoate

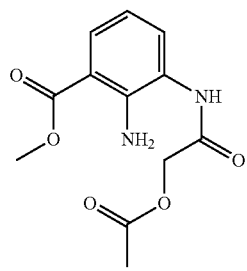 [SMILES: COC(=O)c1cccc(NC(=O)COC(C)=O)c1N]

To a solution of methyl 2,3-diaminobenzoate (2.00 g, 12.0 mmol) and N,N-diisopropylethylamine (2.52 mL, 14.5 mmol) in dichloromethane (20 mL) at −30° C. was added dropwise a solution of (2-chloro-2-oxo-ethyl) acetate (1.43 mL, 13.2 mmol) in dichloromethane (20 mL). The mixture was stirred at 15° C. for 12 h. The reaction was quenched by addition of saturated ammonium chloride solution (40 mL). The mixture was extracted with ethyl acetate (40 mL×3). The combined organic layers were washed with saturated sodium chloride solution (30 mL×3), dried over sodium sulfate, filtered and concentrated to afford methyl 3-[(2-acetoxyacetyl)amino]-2-amino-benzoate (2.00 g, 7.51 mmol, 62% yield) as a dark green solid. The product was used without purification. LCMS (ESI): m/z=267.1 [M+H]⁺.

b. Methyl 2-(acetoxymethyl)-1H-benzo[d]imidazole-4-carboxylate

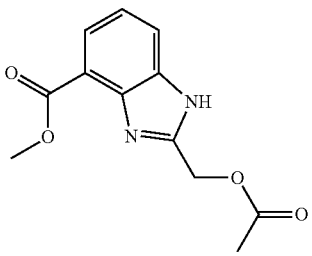 [SMILES: COC(=O)c1cccc2[nH]c(COC(C)=O)nc12]

A mixture of methyl 3-[(2-acetoxyacetyl)amino]-2-amino-benzoate (2.00 g, 7.51 mmol) in acetic acid (15 mL) was stirred at 100° C. for 30 min. The reaction mixture was concentrated under reduced pressure to remove acetic acid. The residue was purified by silica gel column chromatography (petroleum ether/ethyl acetate=5:1 to 0:1) to afford methyl 2-(acetoxymethyl)-1H-benzimidazole-4-carboxylate (400 mg, 1.61 mmol, 21% yield) as a yellow solid. LCMS (ESI): m/z=249.1 [M+H]⁺.

c. 2-(Hydroxymethyl)-1H-benzo[d]imidazole-4-carboxylic Acid

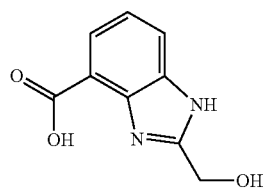 [SMILES: O=C(O)c1cccc2[nH]c(CO)nc12]

The title compound was prepared in an analogous manner to Intermediate 2-(tert-Butyl)-1H-imidazole-4-carboxylic acid, Step B to afford 2-(hydroxymethyl)-1H-benzo[d]imidazole-4-carboxylic acid (120 mg, 39% yield) as a yellow solid. ¹H NMR (400 MHz, DMSO-d₆): δ 7.80 (d, J 8.4 Hz, 1H), 7.75 (d, J 7.6 Hz, 1H), 7.24 (t, J 7.2 Hz, 1H), 4.69 (s, 2H).

Preparation of Intermediate
2-bromooxazole-4-carboxylic Acid

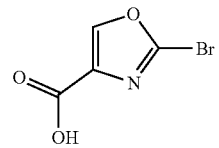

The title compound was prepared in an analogous manner to Intermediate 2-(tert-Butyl)-1H-imidazole-4-carboxylic acid, Step B to afford 2-bromooxazole-4-carboxylic acid (200 mg, 1.04 mmol, 46% yield) as a white solid. LCMS (ESI): m/z=191.9 [M+H]⁺.

Preparation of Intermediate
2-Morpholinooxazole-4-carboxylic Acid

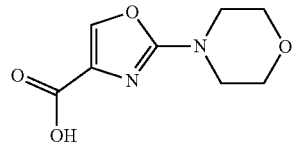 [SMILES: O=C(O)c1coc(N2CCOCC2)n1]

a. Ethyl 2-morpholinooxazole-4-carboxylate

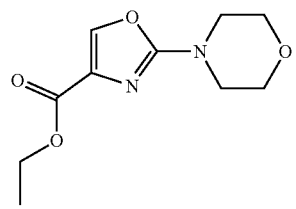 [SMILES: CCOC(=O)c1coc(N2CCOCC2)n1]

To a solution of morpholine (748 mg, 8.59 mmol) in tetrahydrofuran (5 mL) was added ethyl 2-bromooxazole- 4-carboxylate (500 mg, 2.27 mmol). The mixture was heated and stirred at 90° C. for 18 h and then concentrated. The residue was purified by silica gel column (petroleum ether: ethyl acetate=5:1 to 1:1) to give ethyl 2-morpholinooxazole-4-carboxylate (400 mg, 1.77 mmol, 78% yield) as a white solid. LCMS (ESI): m/z=227.1 [M+H]⁺.

b. 2-Morpholinooxazole-4-carboxylic Acid

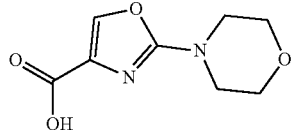 [SMILES: O=C(O)c1coc(N2CCOCC2)n1]

The title compound was prepared in an analogous manner to Intermediate 2-(tert-Butyl)-1H-imidazole-4-carboxylic acid, Step B to afford 2-morpholinooxazole-4-carboxylic acid (100 mg, 28% yield) as a white solid.

Preparation of Intermediate
2-(2-Methylpyridin-4-yl)oxazole-4-carboxylic Acid

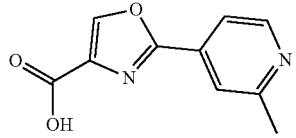

a. Ethyl
2-(2-methylpyridin-4-yl)oxazole-4-carboxylate

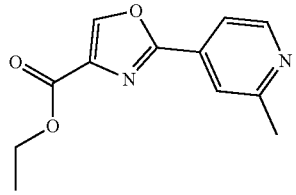 [SMILES: CCOC(=O)c1coc(-c2ccnc(C)c2)n1]

To a mixture of ethyl 2-bromooxazole-4-carboxylate (500 mg, 2.27 mmol) and (2-methylpyridin-4-yl)boronic acid (622 mg, 4.55 mmol) in acetonitrile (5 mL) was added cesium carbonate (1.48 g, 4.55 mmol) and 1,1'-bis(diphenylphosphino)ferrocene-palladium(II)dichloride dichloromethane complex (185 mg). The mixture was heated and stirred at 85° C. for 12 h. The mixture was filtered, and the filtrate was concentrated and purified by preparatory thin layer chromatography (petroleum ether: ethyl acetate=1:1) to give ethyl 2-(2-methylpyridin-4-yl)oxazole-4-carboxylate (200 mg, 38%) as a light brown solid. ¹H NMR (400 MHz, CDCl₃): δ 8.66 (d, J 5.6 Hz, 1H), 8.34 (s, 1H), 7.87 (s, 1H), 7.75 (d, J 4.8 Hz, 1H), 4.45 (q, J 7.2 Hz, 2H), 1.42 (t, J 7.2 Hz, 3H). LCMS (ESI): m/z=233.1 [M+H]⁺.

b. 2-(2-methylpyridin-4-yl)oxazole-4-carboxylic Acid

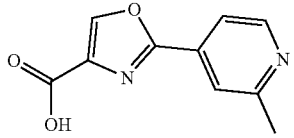

The title compound was prepared in an analogous manner to Intermediate 2-(tert-Butyl)-1H-imidazole-4-carboxylic acid, Step B to afford 2-(2-methylpyridin-4-yl)oxazole-4-carboxylic acid (50 mg, 52% yield) as a white solid. LCMS (ESI): m/z=205.1 [M+H]⁺.

Preparation of Intermediate
2-(Pyrimidin-4-yl)oxazole-4-carboxylic Acid

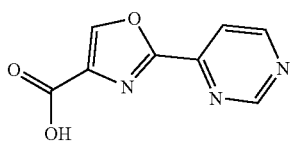 [SMILES: O=C(O)c1coc(-c2ccncn2)n1]

a. Ethyl 2-(pyrimidin-4-yl)oxazole-4-carboxylate

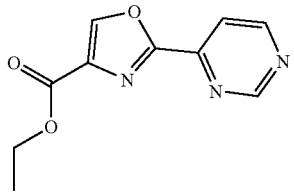 [SMILES: CCOC(=O)c1coc(-c2ccncn2)n1]

A mixture of ethyl 2-bromooxazole-4-carboxylate (500 mg, 2.27 mmol), tributyl(pyrimidin-4-yl)stannane (1.01 g, 2.72 mmol), copper (I) iodide (43 mg, 0.23 mmol), cesium fluoride (690 mg, 4.54 mmol) and Pd(PPh₃)₄ (262 mg, 0.23 mmol) in N,N-dimethylformamide (15 mL) was degassed and purged with nitrogen three times. The mixture was stirred at 8° C. for 1 h under nitrogen. The reaction was quenched by the addition water (20 mL), diluted with ethyl acetate (10 mL), and extracted with ethyl acetate (20 mL×3). The combined organic layers were washed with a sub-saturated aqueous sodium chloride solution (30 mL×3), dried with anhydrous sodium sulfate, filtered and concentrated under reduced pressure to give a residue. The crude product was purified by preparatory thin layer chromatography (petroleum ether: ethyl acetate=15:1 to 1:1) to afford ethyl 2-pyrimidin-4-yloxazole-4-carboxylate (100 mg, 18% yield) as a yellow solid. LCMS (ESI): m/z=220 [M+H]⁺.

b. 2-(pyrimidin-4-yl)oxazole-4-carboxylic Acid

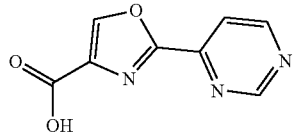

The title compound was prepared in an analogous manner to Intermediate 2-(tert-Butyl)-1H-imidazole-4-carboxylic acid, Step B to afford 2-pyrimidin-4-yloxazole-4-carboxylic acid (40 mg) as a white solid. LCMS (ESI): m/z=192 [M+H]⁺.

Preparation of Intermediate
2-(4-Methyl-1H-imidazol-1-yl)oxazole-4-carboxylic Acid

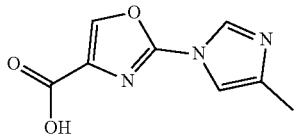

a. Ethyl 2-(4-methyl-1H-imidazol-1-yl)oxazole-4-carboxylate

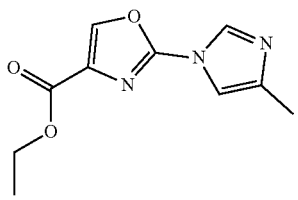 [SMILES: CCOC(=O)c1coc(-n2cnc(C)c2)n1]

To a mixture of ethyl 2-bromooxazole-4-carboxylate (1 g, 4.5 mmol) and 4-methyl-1H-imidazole (448 mg, 5.45 mmol) in N,N-dimethylformamide (1 mL) was added N,N-diisopropylethylamine (1.59 mL, 9.09 mmol) and the mixture was heated and stirred at 100° C. for 12 h. The mixture was purified by silica gel column (eluting gradient:petroleum ether/ethyl acetate=10:1 to 0:1) to give ethyl 2-(4-methyl-1H-imidazol-1-yl)oxazole-4-carboxylate (0.3 g, crude) as a light brown solid. LCMS (ESI): m/z=222.1 [M+H]⁺.

b. 2-(4-methyl-1H-imidazol-1-yl)oxazole-4-carboxylic Acid

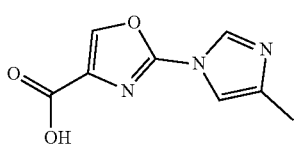

The title compound was prepared in an analogous manner to Intermediate 2-(tert-Butyl)-1H-imidazole-4-carboxylic acid, Step B to afford 2-(4-methylimidazol-1-yl)oxazole-4-carboxylic acid (150 mg, 57% yield) as a white solid. ¹H NMR (400 MHz, DMSO-d₆): δ 8.75 (s, 1H), 8.29 (s, 1H), 7.51 (s, 1H), 2.18 (s, 3H).

Preparation of Intermediate
2-morpholinothiazole-4-carboxylic Acid

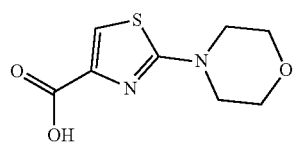 [SMILES: O=C(O)c1csc(N2CCOCC2)n1]

a. Methyl 2-morpholinothiazole-4-carboxylate

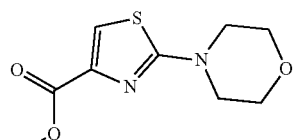

A mixture of methyl 2-bromothiazole-4-carboxylate (1.00 g, 4.50 mmol) and morpholine (1.19 mL, 13.5 mmol) in tetrahydrofuran (10 mL) was degassed and purged with nitrogen for three times, and then the mixture was stirred at 70° C. for 12 h under nitrogen. The reaction mixture was concentrated under reduced pressure. The residue was purified by silica gel column chromatography (petroleum ether/ethyl acetate=10:1 to 8:1) to afford methyl 2-morpholinothiazole-4-carboxylate (500 mg, 41% yield) as a white solid. LCMS (ESI): m/z=229.3[M+H]⁺.

b. 2-Morpholinothiazole-4-carboxylic Acid

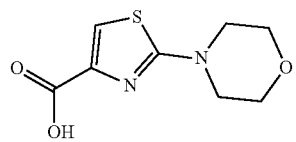 [SMILES: O=C(O)c1csc(N2CCOCC2)n1]

The title compound was prepared in an analogous manner to Intermediate 2-(tert-Butyl)-1H-imidazole-4-carboxylic acid, Step B to afford 2-morpholinothiazole-4-carboxylic acid (200 mg, 53% yield) as a white solid. ¹H NMR (400 MHz, DMSO-d₆): δ 7.61 (s, 1H), 3.70-3.67 (m, 4H), 3.38-3.35 (m, 4H).

Preparation of Intermediate
2-(3-Methylmorpholino)thiazole-4-carboxylic Acid

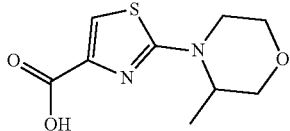

a. Methyl
2-(3-methylmorpholino)thiazole-4-carboxylate

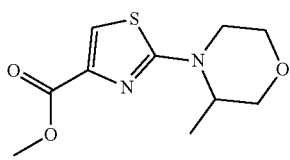 [SMILES: COC(=O)c1csc(N2CCOCC2C)n1]

A mixture of methyl 2-bromothiazole-4-carboxylate (500 mg, 2.25 mmol), 3-methylmorpholine (342 mg, 3.37 mmol), cesium fluoride (479 mg, 3.15 mmol), cesium carbonate (1.03 g, 3.15 mmol) in dimethyl sulfoxide (5.0 mL) was degassed and purged with nitrogen for three times. The mixture was irradiated under microwave conditions and stirred at 110° C. for 9 h. The reaction mixture was concentrated under reduced pressure. The residue was purified by silica-gel column chromatography (petroleum ether/ethyl acetate=15:1 to 1:1) to afford methyl 2-(3-methylmorpholino)thiazole-4-carboxylate (120 mg, 22% yield) as a white solid. LCMS (ESI): m/z=242.9 [M+H]$^+$.

b. 2-(3-Methylmorpholino)thiazole-4-carboxylic Acid

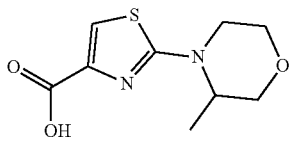

The title compound was prepared in an analogous manner to Intermediate 2-(tert-Butyl)-1H-imidazole-4-carboxylic acid, Step B to afford 2-(3-methylmorpholin-4-yl)thiazole-4-carboxylic acid (50 mg, 53% yield) as a white solid. LCMS (ESI): m/z=228.8 [M+H]$^+$.

Example 58. N-(2,2-Dimethyl-6-morpholino-3H-benzofuran-5-yl)-1-(6-methoxy-3-pyridyl)pyrazole-3-carboxamide

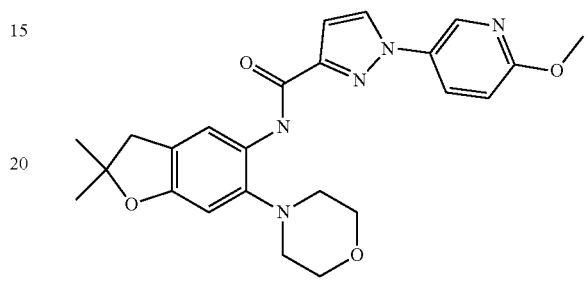

A mixture of 1,4-diazabicyclo[2.2.2]octane-trimethylaluminum (686 mg, 2.68 mmol), 2,2-dimethyl-6-morpholino-3H-benzofuran-5-amine (319 mg, 1.29 mmol) and methyl 1-(6-methoxy-3-pyridyl)pyrazole-3-carboxylate (250 mg, 1.07 mmol) in toluene (15 mL) was stirred at 120° C. for 16 h in a sealed tube. Methanol was added, and the reaction was cooled to room temperature and concentrated under reduced pressure. The residue was purified by silica gel chromatography (eluting with 7:3 ethyl acetate: petroleum ether) to afford N-(2,2-dimethyl-6-morpholino-3H-benzofuran-5-yl)-1-(6-methoxy-3-pyridyl)pyrazole-3-carboxamide (94%) as an off-white solid. $^1$H NMR (400 MHz, DMSO-d$_6$): δ 9.89 (s, 1H), 8.76-8.75 (m, 1H), 8.62-8.61 (m, 1H), 8.27-8.24 (m, 1H), 8.20 (s, 1H), 7.09-7.04 (m, 2H), 6.73 (s, 1H), 3.93 (s, 3H), 3.81 (m, 4H), 3.01 (m, 2H), 2.83 (m, 4H), 1.41 (s, 6H). MS (ESI): m/z=450.2 [M+1]$^+$.

The following compounds were made in a manner similar to that described for Example 58.

| Ex. | Name | Structure | NMR, MS |
|---|---|---|---|
| 59 | N-(2,2-Dimethyl-6-morpholino-3H-benzofuran-5-yl)-1-[2-(hydroxymethyl)-4-pyridyl]pyrazole-3-carboxamide | 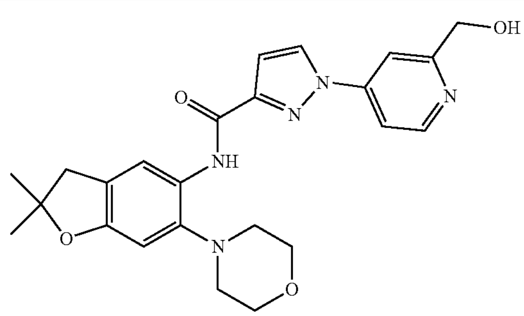 [SMILES: CC1(C)Cc2cc(NC(=O)c3ccn(-c4ccnc(CO)c4)n3)c(N3CCOCC3)cc2O1] | $^1$H NMR (400 MHz, CD$_3$OD): δ 8.63-8.61 (m, 2H), 8.24-8.19 (m, 2H), 7.84-7.83 (m, 1H), 7.11-7.10 (m, 1H), 6.69 (s, 1H), 4.80 (s, 2H), 3.98-3.96 (m, 4H), 3.04 (m, 2H), 2.92-2.90 (m, 4H), 1.46 (s, 6H). MS (ESI): m/z = 450.2 [M + 1]$^+$. |

-continued

| Ex. | Name | Structure | NMR, MS |
|---|---|---|---|
| 60 | N-(2,2-Dimethyl-6-morpholino-3H-benzofuran-5-yl)-1-(2-methoxy-4-pyridyl)pyrazole-3-carboxamide | 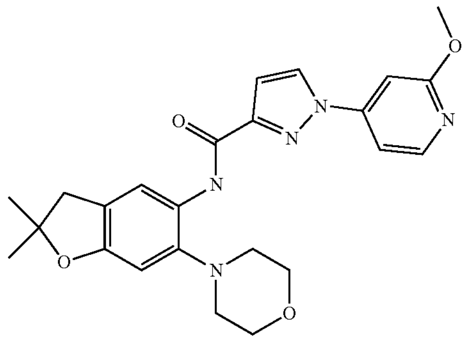 [SMILES: COc1cc(-n2ccc(C(=O)Nc3cc4c(cc3N3CCOCC3)OC(C)(C)C4)n2)ccn1] | $^1$H NMR (400 MHz, DMSO) d$_6$): δ 9.95 (s, 1H), 8.88-8.87 (m, 1H), 8.362-8.348 (m, 1H), 8.187 (s, 1H), 7.634 (m, 1H), 7.428 (s, 1H), 7.096-7.090 (m, 1H), 6.756 (s, 1H), 3.941 (s, 3H), 3.839 (m, 4H), 3.015 (m, 2H), 2.836 (m, 4H), 1.416 (s, 6H). MS (ESI): m/z = 450.2 [M + 1]$^+$. |
| 61 | N-(2,2-Dimethyl-6-morpholino-3H-benzofuran-5-yl)-1-[2-(1-hydroxy-1-methyl-ethyl)-4-pyridyl]pyrazole-3-carboxamide | 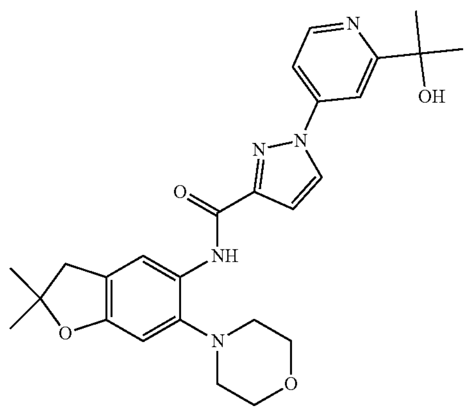 [SMILES: CC1(C)Cc2cc(NC(=O)c3ccn(-c4ccnc(C(C)(C)O)c4)n3)c(N3CCOCC3)cc2O1] | $^1$H NMR (400 MHz, CD$_3$OD-d$_6$): δ 8.647-8.612 (m, 2H), 8.362-8.357 (m, 1H), 8.201 (s, 1H), 7.807-7.788 (m, 1H), 7.117-7.111 (m, 1H), 6.694 (s, 1H), 3.993-3.971 (m, 4H), 3.055 (m, 2H), 2.930-2.908 (m, 4H), 1.632 (s, 6H), 1.416 (s, 6H). MS (ESI): m/z = 478.3 [M + 1]$^+$. |
| 62 | N-(2,2-Dimethyl-6-morpholino-3H-benzofuran-5-yl)-1-[2-(2,2,2-trifluoroethyl amino)-4-pyridyl]pyrazole-3-carboxamide | 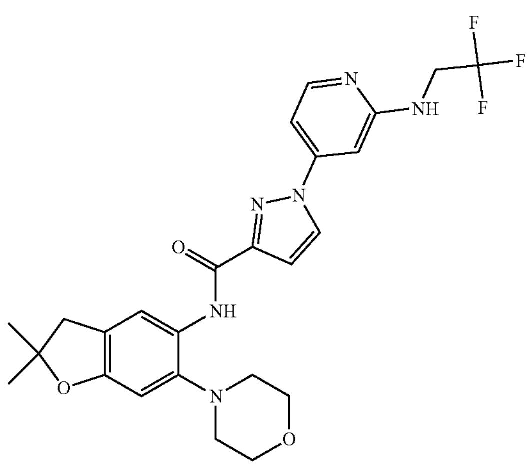 [SMILES: CC1(C)Cc2cc(NC(=O)c3ccn(-c4ccnc(NCC(F)(F)F)c4)n3)c(N3CCOCC3)cc2O1] | $^1$H NMR (400 MHz, CDCl$_3$-d$_6$): δ 10.005 (s, 1H), 8.321 (s, 1H), 8.248-8.234 (m, 1H), 8.022-8.016 (m, 1H), 7.110-7.044 (m, 2H), 6.962-6.958 (m, 1H), 6.632 (s, 1H), 4.920-4.886 (m, 1H), 4.213-4.174 (m, 2H), 3.984-3.962 (m, 4H), 3.035 (m, 2H), 2.930-2.908 (m, 4H), 1.485 (s, 6H). MS (ESI): m/z = 517 [M + 1]$^+$. |

Example 63. 1-(2-Cyano-4-pyridyl)-N-(2,2-dimethyl-6-morpholino-3H-benzofuran-5-yl)pyrazole-3-carboxamide

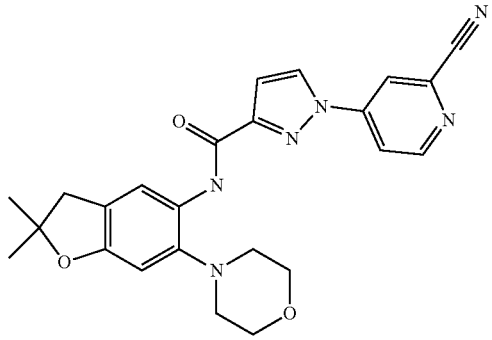 [SMILES: CC1(C)Cc2cc(NC(=O)c3ccn(-c4ccnc(C#N)c4)n3)c(N3CCOCC3)cc2O1]

A mixture of (7-azabenzotriazol-1-yloxy)tripyrrolidinophosphonium hexafluorophosphate (133 mg, 0.25 mmol), 4-dimethylaminopyridine (28 mg, 0.23 mmol), N,N-diisopropylethylamine (30.1 mg, 0.23 mmol), 2,2-dimethyl-6-morpholino-3H-benzofuran-5-amine (Intermediate 1, 58 mg, 0.23 mmol) and 1-(2-cyano-4-pyridyl)pyrazole-3-carboxylic acid (50 mg, 0.23 mmol) in N,N-dimethylformamide (1 mL) was stirred at room temperature for 16 h. The reaction mixture was concentrated under reduced pressure and purified by silica gel chromatography (eluent 7:3 ethyl acetate: petroleum ether) to afford 1-(2-cyano-4-pyridyl)-N-(2,2-dimethyl-6-morpholino-3H-benzofuran-5-yl)pyrazole-3-carboxamide (35 mg, 34%) as a solid. $^1$H NMR (400 MHz, dimethyl sulfoxide-d$_6$): δ 9.94 (s, 1H), 8.95-8.94 (m, 2H), 8.65 (m, 1H), 8.29-8.27 (m, 1H), 8.14 (s, 1H), 7.17-7.16 (m, 1H), 6.75 (s, 1H), 3.84 (m, 4H), 3.01 (m, 2H), 2.84 (m, 4H), 1.42 (s, 6H). MS (ESI): m/z=445.2 [M+1]$^+$.

Example 64. N-(2,2-Dimethyl-6-morpholino-3H-benzofuran-5-yl)-3-(2-hydroxyethyl)triazolo[4,5-c]pyridine-7-carboxamide

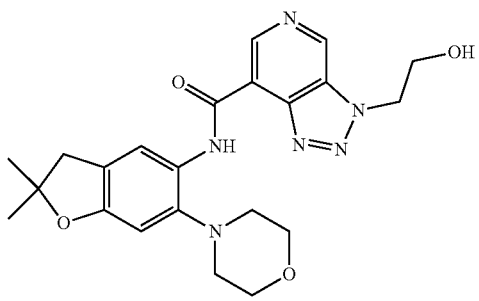 [SMILES: CC1(C)Cc2cc(NC(=O)c3cncc4c3nnn4CCO)c(N3CCOCC3)cc2O1]

a. 3-[2-[tert-Butyl(diphenyl)silyl]oxyethyl]-N-(2,2-dimethyl-6-morpholino-3H-benzofuran-5-yl)triazolo[4,5-c]pyridine-7-carboxamide

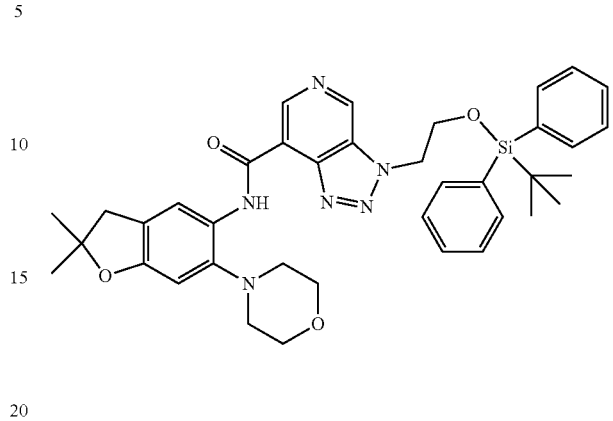

The title compound was made in a manner analogous to Example 69 to give 3-[2-[tert-butyl(diphenyl)silyl]oxyethyl]-N-(2,2-dimethyl-6-morpholino-3H-benzofuran-5-yl)triazolo[4,5-c]pyridine-7-carboxamide (70 mg, 31% yield) as a yellow solid. MS (ESI): m/z=677.3 [M+1]$^+$.

b. N-(2,2-Dimethyl-6-morpholino-3H-benzofuran-5-yl)-3-(2-hydroxyethyl)triazolo[4,5-c]pyridine-7-carboxamide

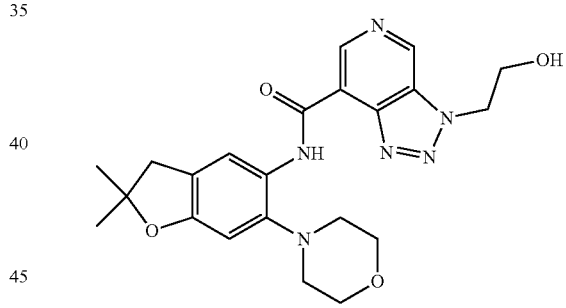

A mixture of 3-[2-[tert-butyl(diphenyl)silyl]oxyethyl]-N-(2,2-dimethyl-6-morpholino-3H-benzofuran-5-yl)triazolo[4,5-c]pyridine-7-carboxamide (60 mg, 0.09 mmol) and 12 N hydrochloric acid (0.15 mL) in methanol (5 mL) was stirred at room temperature for 2 h. The mixture was purified by preparative HPLC (Gilson 281, Xbridge 21.2*250 mm c18, 10 um; A: acetonitrile 25-55%; B: 10 M ammonium bicarbonate in water) to afford N-(2,2-dimethyl-6-morpholino-3H-benzofuran-5-yl)-3-(2-hydroxyethyl)triazolo[4,5-c]pyridine-7-carboxamide (15.9 mg, 41%) as a yellow solid. $^1$H NMR (400 MHz, DMSO-d$_6$): δ 11.43 (s, 1H), 9.64 (s, 1H), 9.09 (s, 1H), 8.46 (s, 1H), 6.81 (s, 1H), 5.13 (t, J 5.6 Hz, 1H), 5.06 (t, J 5.2 Hz, 1H), 3.96 (q, J=5.6 Hz, 2H), 3.91 (t, J=4.4 Hz, 4H), 3.04 (s, 2H), 2.86 (t, J=4.4 Hz, 4H), 1.43 (s, 6H). MS (ESI): m/z=439.2 [M+1]$^+$.

Example 65. N-(2,2-Dimethyl-6-morpholino-3H-benzofuran-5-yl)-2-methyl-imidazo[1,2-a]pyridine-8-carboxamide

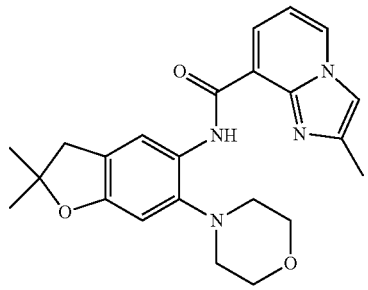

The title compound was made in a manner analogous to Example 69 to give N-(2,2-dimethyl-6-morpholino-3H-benzofuran-5-yl)-2-methyl-imidazo[1,2-a]pyridine-8-carboxamide (59 mg, 36%) as a pale yellow solid. $^1$H NMR (400 MHz, DMSO-$d_6$): δ 12.02 (s, 1H), 8.73-8.71 (m, 1H), 8.19 (s, 1H), 8.09-8.07 (m, 1H), 7.92 (m, 1H), 7.09-7.06 (m, 1H), 6.62 (s, 1H), 3.82 (m, 4H), 3.00 (m, 2H), 2.84 (m, 4H), 2.52-2.51 (m, 3H), 1.42 (s, 6H). MS (ESI): m/z=407.2 [M+1]$^+$.

Example 66. N-(2,2-Dimethyl-6-morpholino-3H-benzofuran-5-yl)-1-(6-oxo-1H-pyridin-3-yl)pyrazole-3-carboxamide

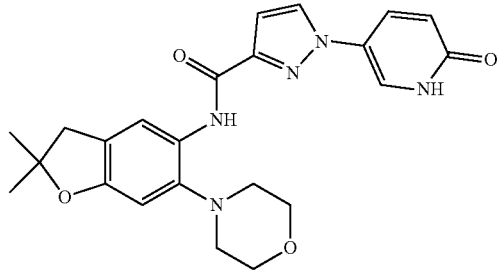 [SMILES: CC1(C)Cc2cc(NC(=O)c3ccn(-c4ccc(=O)[nH]c4)n3)c(N3CCOCC3)cc2O1]

A mixture of N-(2,2-dimethyl-6-morpholino-3H-benzofuran-5-yl)-1-(6-methoxy-3-pyridyl)pyrazole-3-carboxamide (Example 58)(300 mg, 0.67 mmol) and N-(2,2-dimethyl-6-morpholino-3H-benzofuran-5-yl)-1-(2-methoxy-4-pyridyl)pyrazole-3-carboxamide (20.0 mg, 0.04 mmol) in acetic acid (20 mL) was stirred at 100° C. for 16 h. Solvents were then removed under reduced pressure and the residue was purified by reverse phase combi-flash chromatography (eluting 40% acetonitrile in 0.5% formic acid in water) to afford N-(2,2-dimethyl-6-morpholino-3H-benzofuran-5-yl)-1-(6-oxo-1H-pyridin-3-yl)pyrazole-3-carboxamide (255 mg, 88%) as an off-white solid. $^1$H NMR (400 MHz, DMSO-$d_6$): δ 9.85 (s, 1H), 8.48 (m, 1H), 8.38 (m, 1H), 8.18 (s, 1H), 8.08-8.03 (m, 2H), 6.97 (s, 1H), 6.72 (s, 1H), 6.59-6.57 (m, 2H), 3.79 (m, 4H), 3.01 (m, 2H), 2.81 (m, 4H), 1.41 (s, 6H). MS (ESI): m/z=436.2 [M+1]$^+$.

Examples 67 and 68. (R)—N-(2-(Hydroxymethyl)-2-methyl-6-morpholino-2,3-dihydrobenzofuran-5-yl)-3-methyl-3H-[1,2,3]triazolo[4,5-c]pyridine-7-carboxamide and (S)—N-(2-(Hydroxymethyl)-2-methyl-6-morpholino-2,3-dihydrobenzofuran-5-yl)-3-methyl-3H-[1,2,3]triazolo[4,5-c]pyridine-7-carboxamide

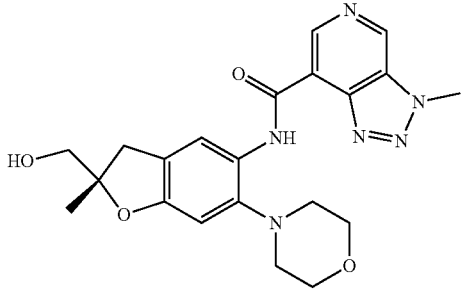

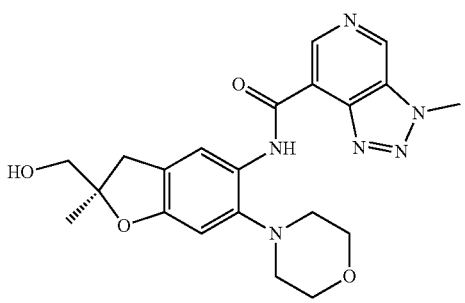

Example 52 was chirally resolved using chiral SFC (SFC-80 (Thar, Waters), OD 20*250 mm, 5 um (Dacel), CO$_2$/methanol{0.2% ammonia (7 M methanol)}=65/35) to provide (R)—N-(2-(hydroxymethyl)-2-methyl-6-morpholino-2,3-dihydrobenzofuran-5-yl)-3-methyl-3H-[1,2,3]triazolo[4,5-c]pyridine-7-carboxamide and (S)—N-(2-(hydroxymethyl)-2-methyl-6-morpholino-2,3-dihydrobenzofuran-5-yl)-3-methyl-3H-[1,2,3]triazolo[4,5-c]pyridine-7-carboxamide with absolute stereochemistry assigned arbitrarily. Example 67, peak 1: $^1$H NMR (400 MHz, DMSO-$d_6$) δ 11.39 (s, 1H), 9.64 (s, 1H), 9.10 (s, 1H), 8.43 (s, 1H), 6.79 (s, 1H), 5.06 (t, J 5.8 Hz, 1H), 4.59 (s, 3H), 3.89 (t, J 4.5 Hz, 4H), 3.52-3.16 (m, 1H), 2.91-2.81 (m, 5H), 1.36 (s, 3H). MS (ESI): m z=425.2 [M+1]$^+$. Example 68, peak 2: $^1$H NMR (400 MHz, DMSO-$d_6$) δ 11.38 (s, 1H), 9.64 (s, 1H), 9.10 (s, 1H), 8.43 (s, 1H), 6.79 (s, 1H), 5.06 (t, J 5.8 Hz, 1H), 4.59 (s, 3H), 3.89 (s, 2H), 3.89 (d, J 9.1 Hz, 1H), 3.52-3.32 (m, 2H), 3.24 (dd, J 15.7, 1.2 Hz, 1H), 2.91-2.81 (m, 5H), 1.36 (s, 3H). MS (ESI): m/z=425.2 [M+1]$^+$.

Example 69. 6-Cyano-N-(2-(hydroxymethyl)-2-methyl-6-morpholino-2,3-dihydrobenzofuran-5-yl)thieno[3,2-b]pyridine-3-carboxamide Formate

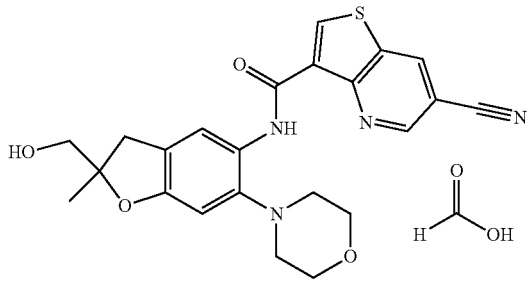 [SMILES: CC1(CO)Cc2cc(NC(=O)c3csc4cc(C#N)cnc34)c(N3CCOCC3)cc2O1 ; O=CO]

A microwave vial equipped with a stir bar was charged with 6-chloro-N-[2-(hydroxymethyl)-2-methyl-6-morpholino-3H-benzofuran-5-yl]thieno[3,2-b]pyridine-3-carboxamide (Examples 56 and 57, 60 mg, 0.13 mmol), 1,1'-bis(diphenylphosphino)ferrocene (72.3 mg, 0.13 mmol), zinc (1.71 mg, 0.03 mmol), zinc cyanide (30.6 mg, 0.26 mmol) and tris(dibenzylideneacetone)dipalladium(O) (12.0 mg, 0.01 mmol) in N,N-dimethylacetamide (2 mL). The reaction mixture was then purged with nitrogen gas, sealed, and heated to 120° C. for 24 h. The mixture was then cooled to room temperature and purified by preparative HPLC to afford 6-cyano-N-[2-(hydroxymethyl)-2-methyl-6-morpholino-3H-benzofuran-5-yl]thieno[3,2-b]pyridine-3-carboxamide (9.3 mg, 16% yield) as the formate salt as a yellow solid. $^1$H NMR (400 MHz, DMSO-$d_6$): δ 11.474 (s, 1H), 9.331-9.305 (m, 2H), 9.255 (s, 1H), 8.226 (s, 1H), 6.69 (s, 1H), 3.80-3.78 (m, 4H), 3.44-3.43 (m, 2H), 3.32 (m, 1H), 2.85-2.81 (m, 5H), 1.35 (s, 3H). MS (ESI): m/z=451.2 [M+1]$^+$.

Example 70. N-(2,2-Dimethyl-6-morpholino-3H-benzofuran-5-yl)-1-(2-oxo-1H-pyridin-4-yl)pyrazole-3-carboxamide

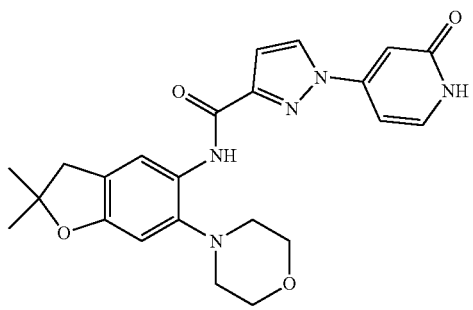 [SMILES: CC1(C)Cc2cc(NC(=O)c3ccn(-c4cc[nH]c(=O)c4)n3)c(N3CCOCC3)cc2O1]

The title compound was made in a manner analogous to Example 66 to give N-(2,2-dimethyl-6-morpholino-3H-benzofuran-5-yl)-1-(2-oxo-1H-pyridin-4-yl)pyrazole-3-carboxamide (66 mg, 68%) as an off-white solid. $^1$H NMR (400 MHz, DMSO-$d_6$): δ 11.86 (br s, 1H), 9.90 (s, 1H), 8.79-8.79 (m, 1H), 8.17 (s, 1H), 7.67-7.65 (m, 1H), 7.07-7.06 (m, 1H), 6.92-6.89 (m, 2H), 6.75 (s, 1H), 3.81 (m, 4H), 3.01 (m, 2H), 2.83 (m, 4H), 1.41 (s, 6H). MS (ESI): m/z=436.2 [M+1]$^+$.

BIOLOGICAL EXAMPLES

Compounds were assayed for inhibition of human IRAK4 and IRAK1 catalytic activity using recombinant enzyme produced from insect cells. Full-length IRAK4 protein, carrying an N-terminal His6-Tag, was obtained from Life Technologies (Carlsbad, Calif., USA). The IRAK1 construct was produced internally and was comprised of IRAK1 residues Arg194 to Ser712, preceded by an NH2-terminal His6 tag and the coding sequence for glutathione-S-transferase.

Kinase activities were assayed using the Transcreener-Fluorecescence polarization platform (BelBrook Labs, Madison, Wis., USA) that measures amounts of the reaction product, ADP. The IRAK4 reaction conditions were optimized using an IRAK1-derived peptide (sequence H-KKARFSRFAGSSPSQSSMVAR) to provide a linear reaction rate over the course of a 90 min incubation, which resulted in 10-12% conversion of the starting ATP to ADP. Final IRAK4 assay conditions were 1.25 nM IRAK4; 125 μM ATP; 10 μM MgCl2; 125 μM peptide in reaction buffer (25 mM HEPES (pH7.4); 2 mM Dithiothreitol; 0.015% Brij-35; and 0.5% dimethyl sulfoxide. The IRAK1 activity was optimized similarly, yielding final assay conditions of 1.5 nM IRAK1; 62.5 μM ATP; 5 μM MgCl2, and 62.5 μM IRAK1 peptide in reaction buffer for 60 min.

Assays of compounds for kinase inhibition were performed using inhibitors serially-diluted in dimethyl sulfoxide, which was accomplished with a LabCyte Echo 555 liquid dispenser. 384 well assay plates spotted with compound received 4 μl of a 2× substrate (ATP+peptide) mix in reaction buffer, followed by 4 μl of 2× enzyme diluted in reaction buffer. Reactions were halted at 60 (IRAK1) or 90 (IRAK4) min by addition of 6 μl of detection buffer, containing EDTA (40 nM final concentration), 0.95 μg of the ADP-binding antibody ADP2, ADP tracer (3 nM final concentration), and 25 μM HEPES. Following a 1 hr incubation, fluorescence polarization of the ADP2-antibody:TRACER complex was read on a Tecan M1000 plate reader using a 635/20 excitation filter in combination with a 670/20 emission filter. Delta milli-P values were analyzed using Genedata software to fit dose-response curves and compute compound Ki values, using ATP Km values of 642 μm and 83.2 μM for IRAK4 and IRAK1, respectively. Table 2 provide IRAK4 Ki values for representative compounds of the present invention.

TABLE 2

IRAK4 Ki values of representative compounds of the present invention.

| Example | IRAK4 Ki (uM) |
|---|---|
| 1 | 0.067 |
| 2 | 0.03 |
| 3 | 0.013 |
| 4 | 0.0071 |
| 5 | 0.025 |
| 6 | 0.038 |
| 7 | 0.043 |
| 8 | 0.045 |
| 9 | 0.53 |
| 10 | 0.027 |
| 11 | 0.29 |
| 12 | 0.077 |
| 13 | 0.28 |
| 14 | 0.34 |
| 15 | 0.036 |
| 16 | 0.048 |
| 17 | 0.12 |
| 18 | 0.0034 |
| 19 | 0.021 |
| 20 | 0.03 |
| 21 | 0.28 |

135
TABLE 2-continued

IRAK4 Ki values of representative compounds of the present invention.

| Example | IRAK4 Ki (uM) |
|---|---|
| 22 | 0.025 |
| 23 | 0.0036 |
| 24 | 0.0077 |
| 25 | 0.035 |
| 26 | 0.035 |
| 27 | 0.042 |
| 28 | 0.47 |
| 29 | 0.23 |
| 30 | 0.78 |
| 31 | 0.023 |
| 32 | 0.019 |
| 33 | 0.0037 |
| 34 | 0.017 |
| 35 | 0.0014 |
| 36 | 0.0038 |
| 37 | 0.0052 |
| 38 | 0.0074 |
| 39 | 0.011 |
| 40 | 0.028 |
| 41 | 0.043 |
| 42 | 0.098 |
| 43 | 0.11 |
| 44 | 0.29 |
| 45 | 0.49 |
| 46 | 0.14 |
| 47 | 0.2 |
| 48 | 0.22 |
| 49 | 0.0076 |
| 50 | 0.078 |
| 51 | 0.018 |
| 52 | 0.1 |
| 53 | 0.22 |
| 54 | 0.81 |
| 55 | 0.39 |
| 56 | 0.037 |
| 57 | 0.019 |
| 58 | 0.029 |
| 59 | 0.0016 |
| 60 | 0.0082 |
| 61 | 0.0046 |
| 62 | 0.017 |
| 63 | 0.016 |
| 64 | 0.35 |
| 65 | 0.27 |
| 66 | 0.014 |
| 67 | 0.18 |
| 68 | 0.07 |
| 69 | 0.028 |
| 70 | 0.0027 |
| 71 | 0.93 |

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The patents, published applications, and scientific literature referred to herein establish the knowledge of those skilled in the art and are hereby incorporated by reference in their entirety to the same extent as if each was specifically and individually.

We claim:
1. A compound of Formula 0:

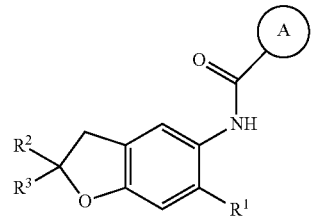

Formula 0 or a stereoisomer or pharmaceutically acceptable salt thereof,
wherein:
$R^1$ is $C_{1-6}$alkoxy, oxetanyl, —$NR^aR^b$, or a 6-membered heteroaryl that is optionally substituted with $R^c$;
$R^2$ is methyl, hydroxymethyl, or 2-hydroxypropan-2-yl and $R^3$ is methyl; or $R^2$ and $R^3$ taken together with the carbon to which they are attached form a 6-membered heterocyclic group that is optionally substituted with $C_{1-3}$ alkyl;
ring A is a 5-membered heteroaryl, a 6-membered heteroaryl, a 6-membered saturated or partially saturated heterocyclic group, or a 9-membered bicyclic heteroaryl that comprises at least two heteroatoms selected form the group consisting of N, O, and S, wherein ring A is optionally substituted with $R^d$; provided ring A is not an optionally substituted 9-membered bicyclic heteroaryl of the following formula

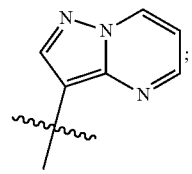 [SMILES: *c1cnn2cccnc12]

$R^a$ and $R^b$ are, independently at each occurrence, $C_{1-6}$alkyl, or $R^a$ and $R^b$ are taken together to form a 6-membered heterocyclic group that is optionally substituted with $R^c$;
each $R^c$ is, independently at each occurrence, halogen; oxo; CN; —$S(O)_{1-2}R^n$; OH; $C_{1-6}$alkoxy; —$NR^eR^f$; —$C(O)(C_{1-3}$alkyl); —$(C_{0-3}$alkyl)$C(O)NR^gR^h$; —$S(O)_{1-2}NR^eR^f$; —$OP(O)(OC_{1-3}$alkyl)$_2$; $C_{3-10}$cycloalkyl group optionally substituted with OH or halogen; a 3-11 membered saturated or partially saturated heterocyclic group optionally substituted with oxo or $C_{1-3}$alkyl; a 5-6 membered monocyclic heteroaryl ring optionally substituted with halogen, oxo, CN, OH, $C_{1-4}$alkoxy, —$NR^eR^f$, or $C_{1-4}$alkyl optionally substituted with halogen, or OH; or $C_{1-4}$alkyl optionally substituted with halogen, oxo, CN, OH, —O—$C_{1-3}$alkyl, —S—$C_{1-3}$ alkyl, —$SO_2$—$C_{1-3}$alkyl, —$NR^eR^f$, —$C(O)NR^eR^f$, phenyl, $C_{3-10}$cycloalkyl, a 3-11 membered saturated or partially saturated heterocyclic group optionally substituted with oxo or $C_{1-3}$ alkyl, or a 5-6 membered monocyclic heteroaryl ring optionally substituted with oxo, halogen, or $C_{1-3}$alkyl;

each $R^d$ is, independently at each occurrence, halogen; oxo; CN; —$OR^n$; —$S(O)_{1-2}R^n$; OH; $C_{1-6}$alkoxy; —$NR^eR^f$; —$C(O)(C_{1-3}$alkyl); —$(C_{0-3}$alkyl)$C(O)NR^gR^h$; —$S(O)_{1-2}NR^eR^f$; —$OP(O)(OC_{1-3}$alkyl)$_2$; $C_{3-10}$cycloalkyl group optionally substituted with OH or halogen; a 3-11 membered saturated or partially saturated heterocyclic group optionally substituted with oxo or $C_{1-3}$alkyl; a 5-6 membered monocyclic heteroaryl ring optionally substituted with halogen, oxo, CN, OH, $C_{1-4}$alkoxy, —$NR^eR^f$, or $C_{1-4}$alkyl optionally substituted with halogen, or OH; or $C_{1-4}$alkyl optionally substituted with halogen, oxo, CN, OH, —O—$C_{1-3}$ alkyl, —S—$C_{1-3}$ alkyl, —$SO_2$—$C_{1-3}$alkyl, —$NR^eR^f$, —$C(O)NR^eR^f$, phenyl, $C_{3-10}$cycloalkyl, a 3-11 membered saturated or partially saturated heterocyclic group optionally substituted with oxo, $C_{1-3}$ alkyl, or a 5-6 membered monocyclic heteroaryl ring optionally substituted with oxo, halogen, or $C_{1-3}$alkyl;

$R^e$, $R^f$, $R^g$ and $R^h$ are, independently at each occurrence, hydrogen, $C_{1-6}$alkyl, $C_{3-6}$ cycloalkyl group, —($C_{0-3}$alkyl)-phenyl, a 3-11 membered saturated heterocyclic group, a 5-6 membered monocyclic heteroaryl ring, —$C(O)R$, —$C(O)OR^n$, —$C(O)NR^kR^m$, or —$S(O)_{1-2}R^n$, or $R^g$ and $R^h$ are taken together to form a 5-8 membered heterocyclic group, wherein any alkyl, cycloalkyl group, phenyl, heterocyclic group, or heteroaryl ring is independently optionally substituted with halogen, oxo, CN, $C_{1-3}$alkyl, $C_{1-3}$haloalkyl, $C_{1-3}$alkoxy, $C_{1-3}$haloalkoxy, —$OR^n$, —$NR^kR^m$, or a 5-6 membered monocyclic heteroaryl ring;

$R^k$ and $R^m$ are, independently at each occurrence, hydrogen, $C_{1-3}$alkyl, or $C_{3-6}$cycloalkyl group, wherein any alkyl or cycloalkyl group is independently optionally substituted with halogen, oxo, CN, OH, $C_{1-3}$alkyl, $C_{1-3}$haloalkyl, $C_{1-3}$alkoxy, or $C_{1-3}$haloalkoxy;

$R^n$ is, independently at each occurrence, hydrogen, $C_{1-6}$alkyl, $C_{3-10}$cycloalkyl group, or a 3-11 membered saturated heterocyclic group, wherein any alkyl, cycloalkyl group, or heterocyclic group is independently optionally substituted with halogen, oxo, CN, OH, $C_{1-3}$alkyl, $C_{1-3}$haloalkyl, $C_{1-3}$alkoxy, $C_{1-3}$haloalkoxy, —$OR^p$, or —$NR^gR^h$; and $R^p$ is, independently at each occurrence, hydrogen, $C_{1-6}$alkyl or $C_{3-6}$cycloalkyl group, wherein any alkyl or cycloalkyl group is independently optionally substituted with halogen, oxo, CN, OH, $C_{1-3}$alkyl, $C_{1-3}$haloalkyl, $C_{1-3}$alkoxy, or $C_{1-3}$haloalkoxy.

2. The compound of claim 1, or a stereoisomer or pharmaceutically acceptable salt thereof, wherein $R^1$ is $C_{1-6}$alkoxy, —$NR^aR^b$, or a 6-membered heteroaryl that is optionally substituted with $R^c$.

3. The compound of claim 2, or a stereoisomer or pharmaceutically acceptable salt thereof, wherein $R^1$ is —$NR^aR^b$.

4. The compound of claim 3, or a stereoisomer or pharmaceutically acceptable salt thereof, wherein $R^a$ and $R^b$ are taken together to form a 6-membered heterocyclic group that is optionally substituted with $R^c$.

5. The compound of claim 4, or a stereoisomer or pharmaceutically acceptable salt thereof, wherein $R^a$ and $R^b$ are taken together to form a morpholino group that is optionally substituted with $R^c$.

6. The compound of claim 2, or a stereoisomer or pharmaceutically acceptable salt thereof, wherein $R^1$ is a 6-membered heteroaryl that is optionally substituted with $R^c$.

7. The compound of claim 6, or a stereoisomer or pharmaceutically acceptable salt thereof, wherein $R^1$ is pyridyl that is optionally substituted with $R^c$.

8. The compound of claim 1, or a stereoisomer or pharmaceutically acceptable salt thereof, wherein $R^1$ is selected from the group consisting of

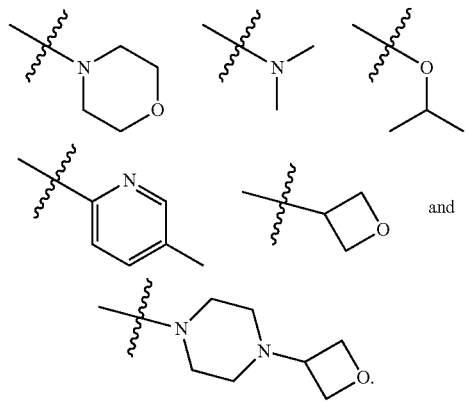

9. The compound of claim 8, or a stereoisomer or pharmaceutically acceptable salt thereof, wherein $R^1$ is selected from the group consisting of

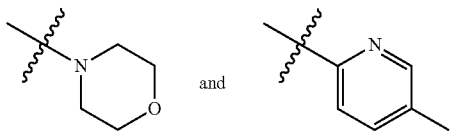

10. The compound of claim 1 wherein ring A is a 5-membered heteroaryl that is optionally substituted with $R^d$.

11. The compound of claim 1 wherein ring A is a 6-membered heteroaryl that is optionally substituted with $R^d$.

12. The compound of claim 1 wherein ring A is a 9-membered bicyclic heteroaryl that comprises at least two heteroatoms selected form the group consisting of N, O, and S, wherein ring A is optionally substituted with $R^d$.

13. The compound of claim 1 wherein each $R^d$ is, independently at each occurrence, halogen; CN; —$S(O)_{1-2}R^n$; OH; $C_{1-6}$alkoxy; —$NR^eR^f$; $C_{3-10}$cycloalkyl group optionally substituted with OH or halogen; a 3-11 membered saturated or partially saturated heterocyclic group optionally substituted with oxo or $C_{1-3}$alkyl; a 5-6 membered monocyclic heteroaryl ring optionally substituted with halogen, oxo, CN, OH, $C_{1-4}$alkoxy, —$NR^eR^f$, or $C_{1-4}$alkyl optionally substituted with halogen, or OH; or $C_{1-4}$alkyl optionally substituted with halogen, or OH.

14. The compound claim 13 wherein each $R^d$ is, independently at each occurrence, oxo, OH, amino, CN, fluoro, chloro, bromo, methyl, ethyl, tert-butyl, 2-hydroxyethyl, methylsulfonyl, hydroxymethyl, trifluoromethyl,

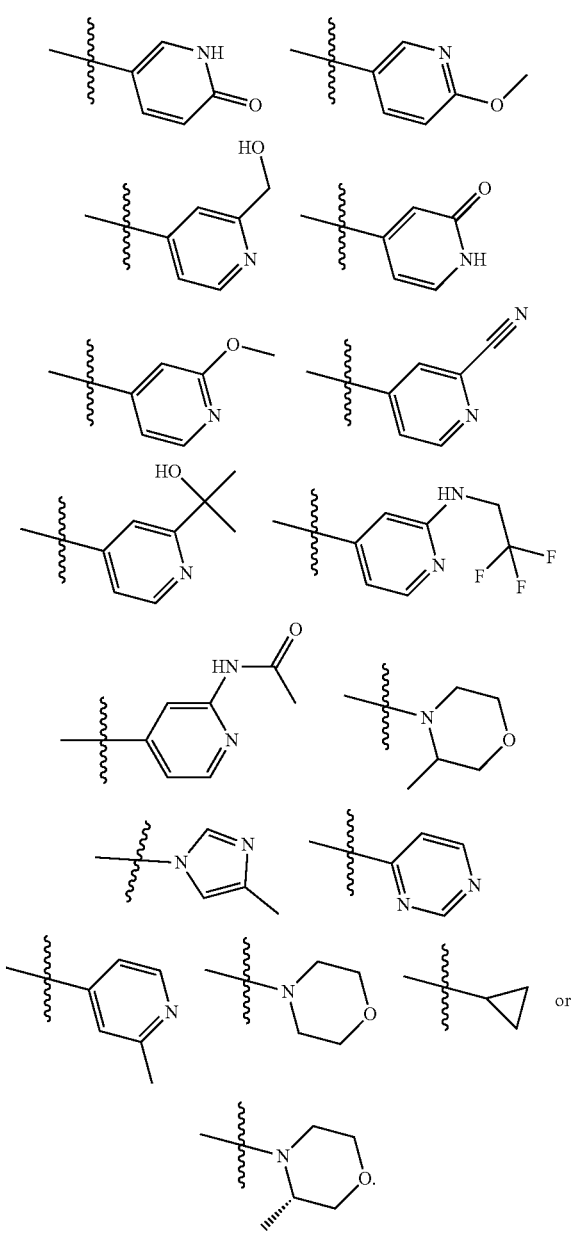
15. The compound of claim 1, wherein ring A is selected from the group consisting of
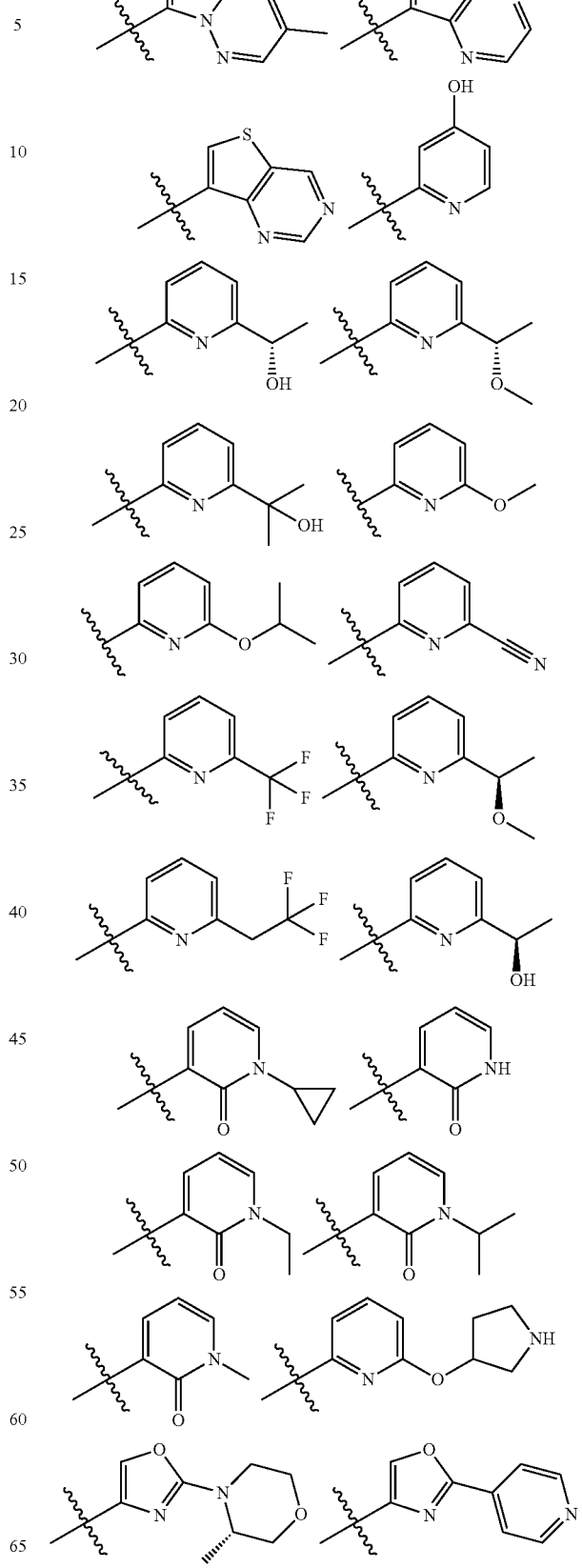
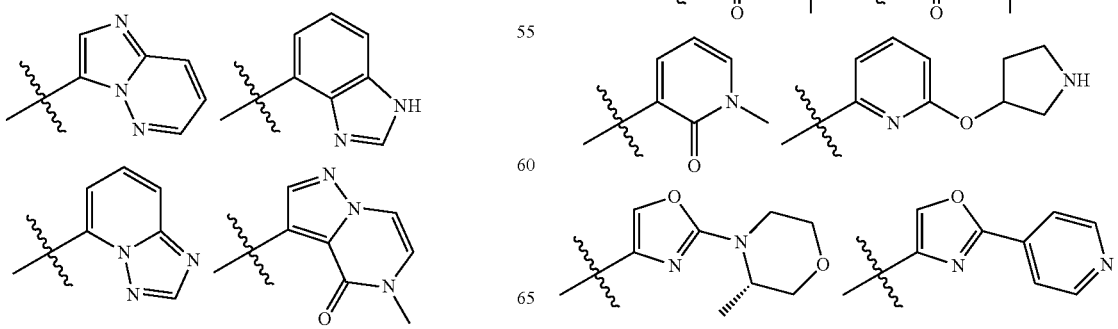

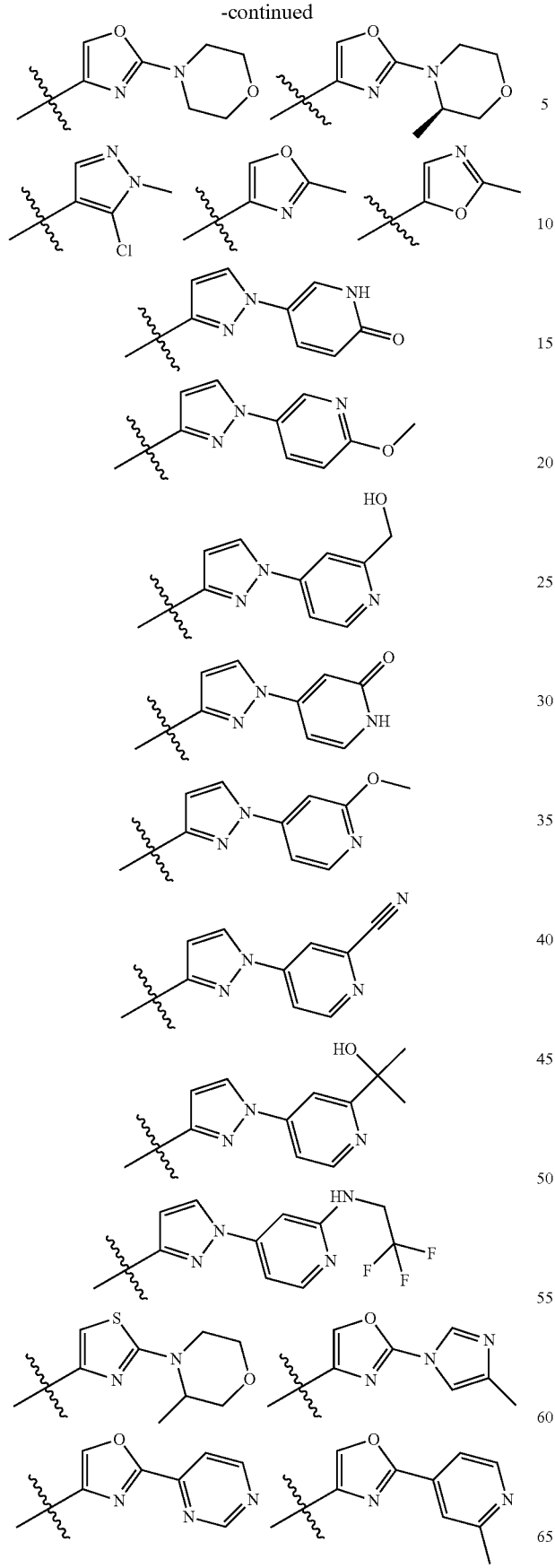
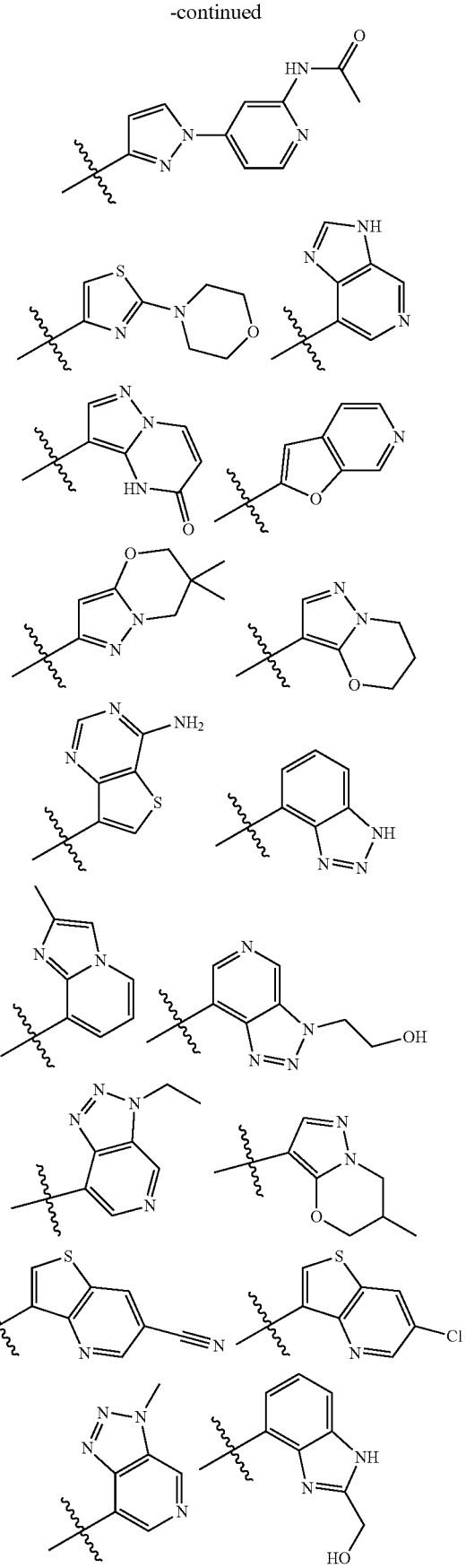

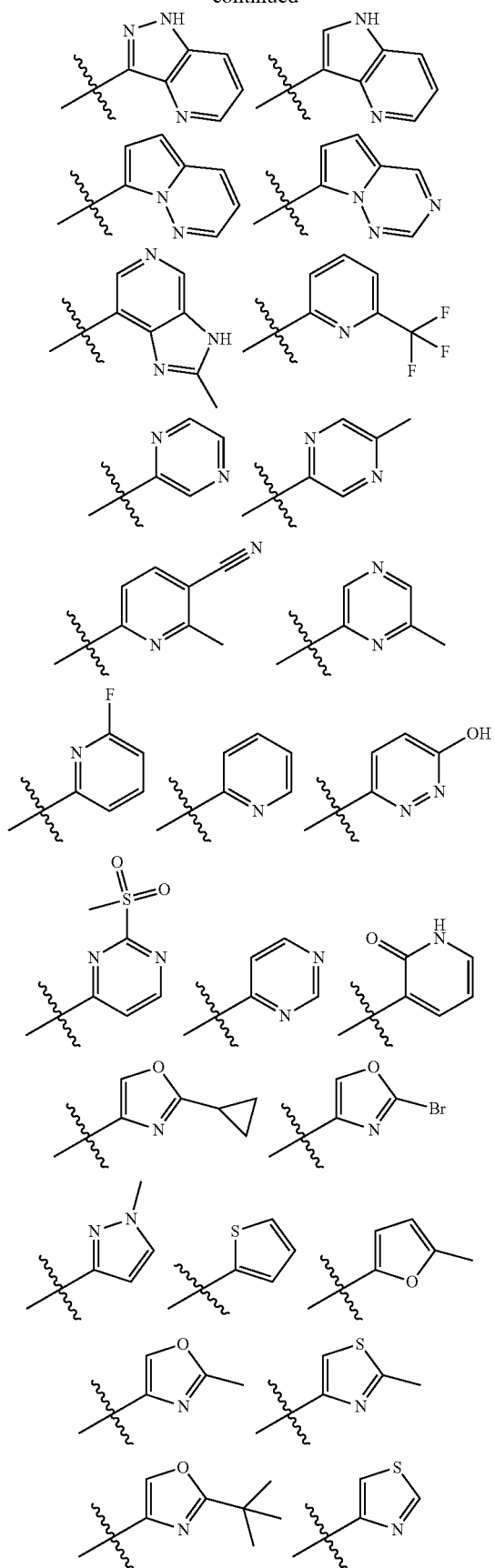
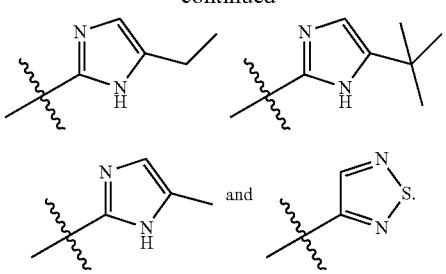
16. The compound of claim 15, wherein ring A is selected from the group consisting of
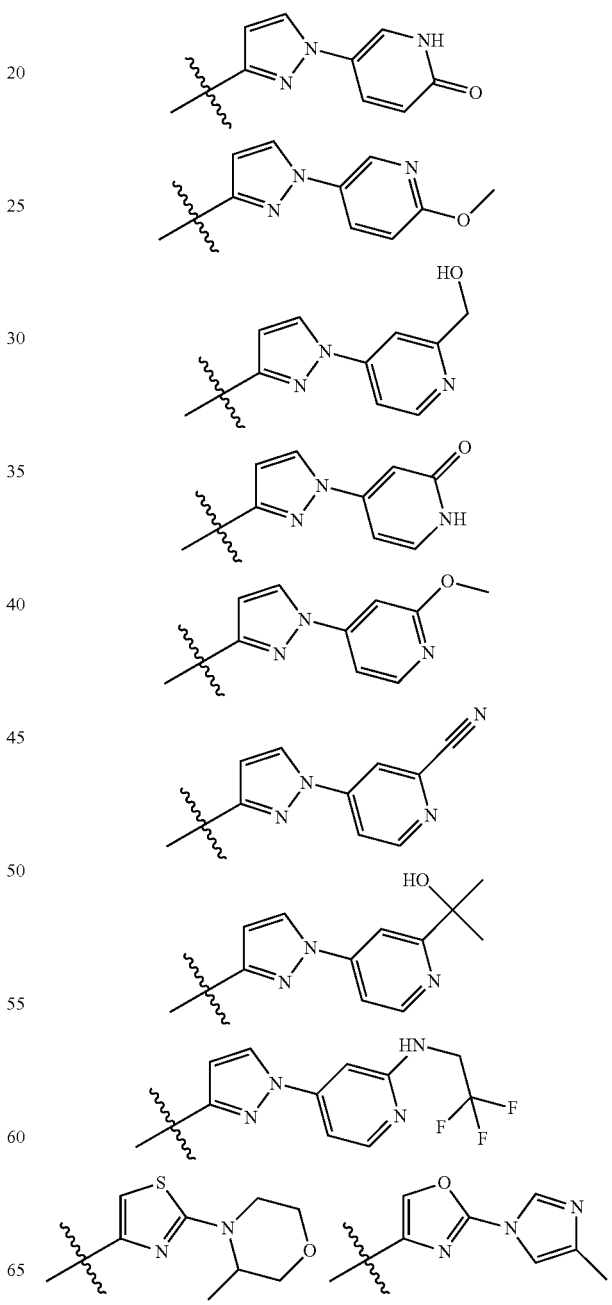

145
-continued
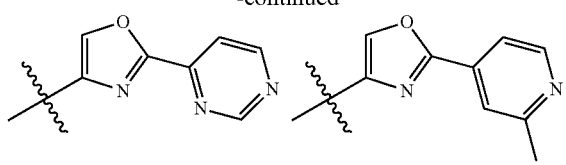
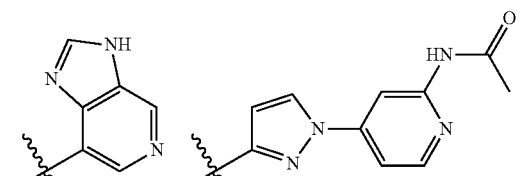
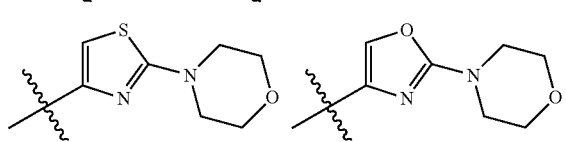
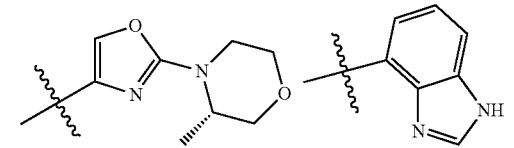
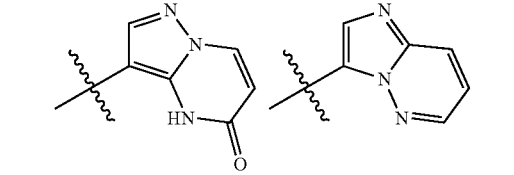
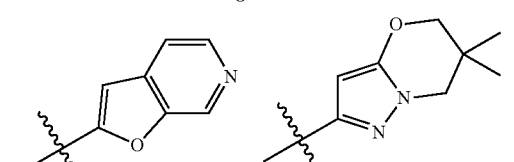
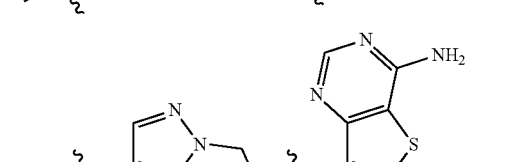
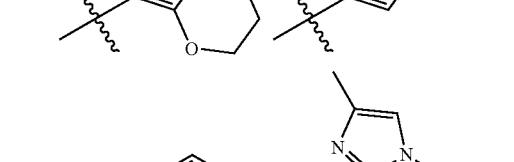
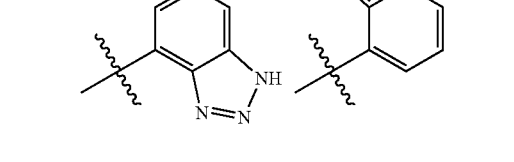
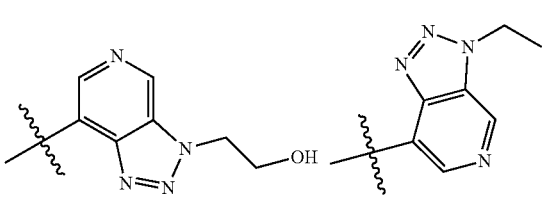
146
-continued
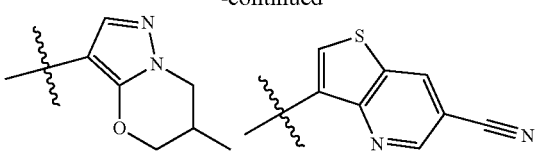
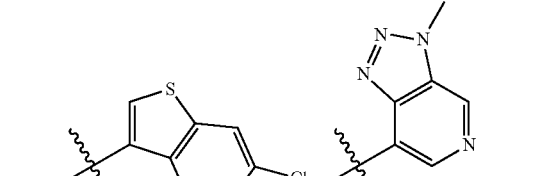
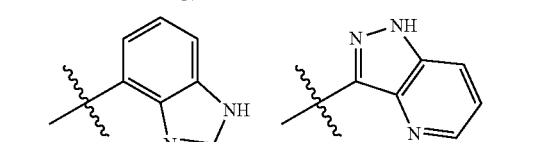
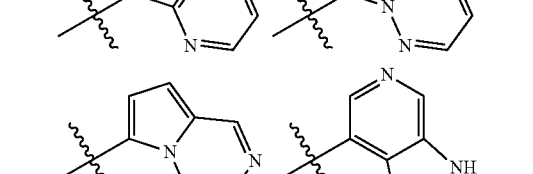
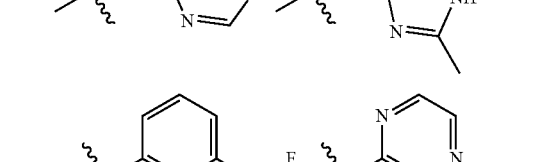
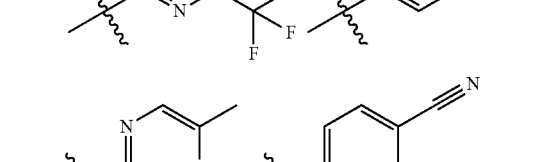
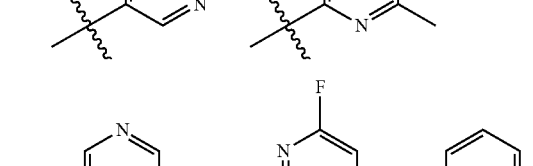
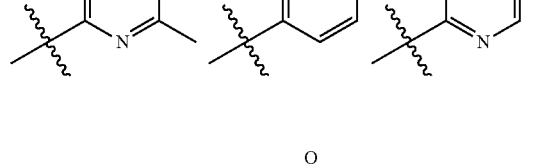
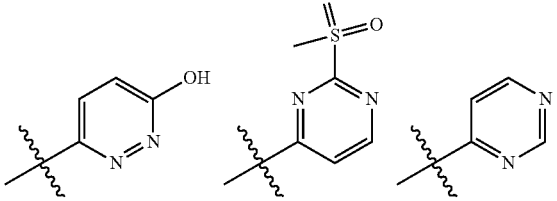

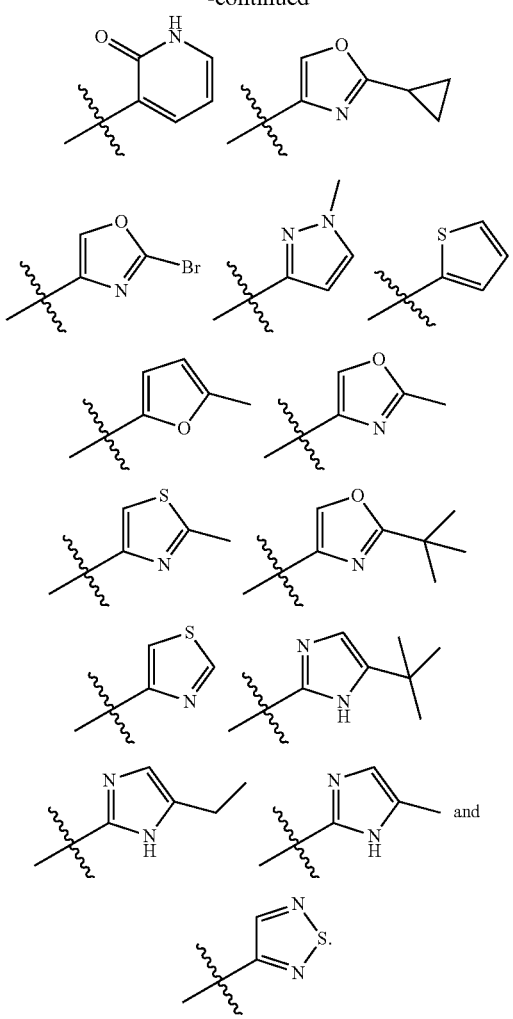
17. The compound of claim 1 selected from the group consisting of
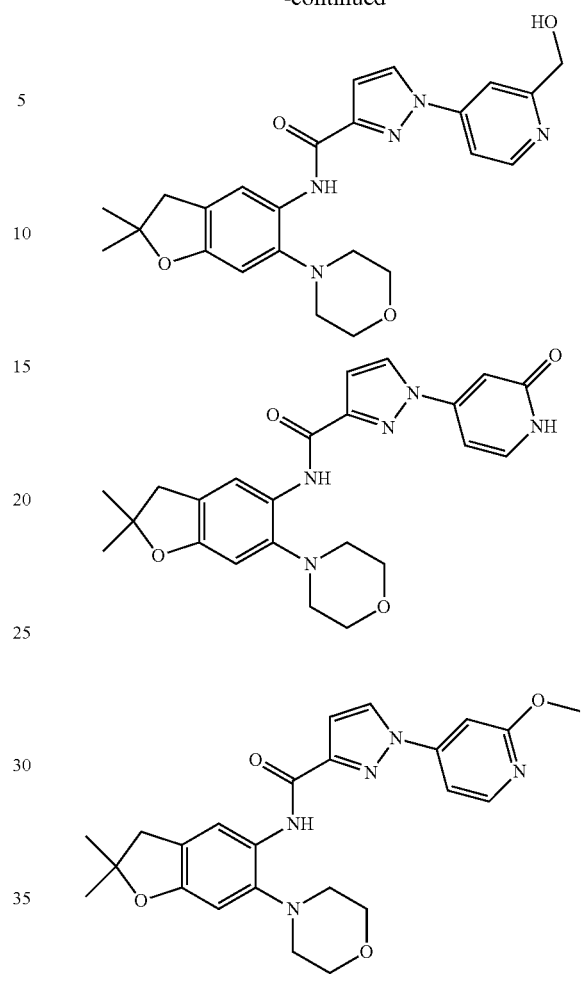
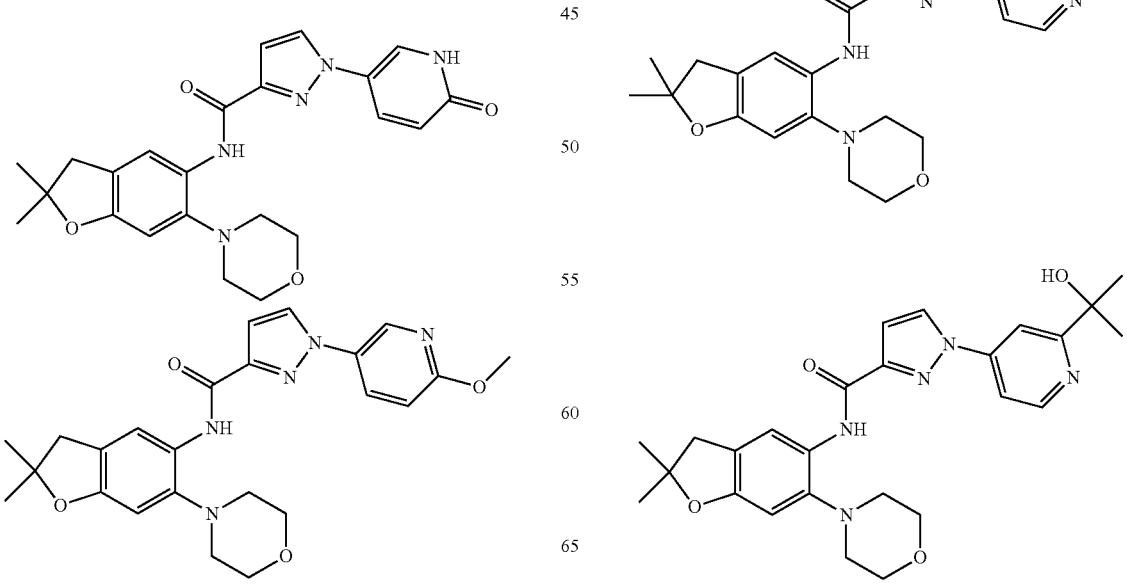

149
-continued
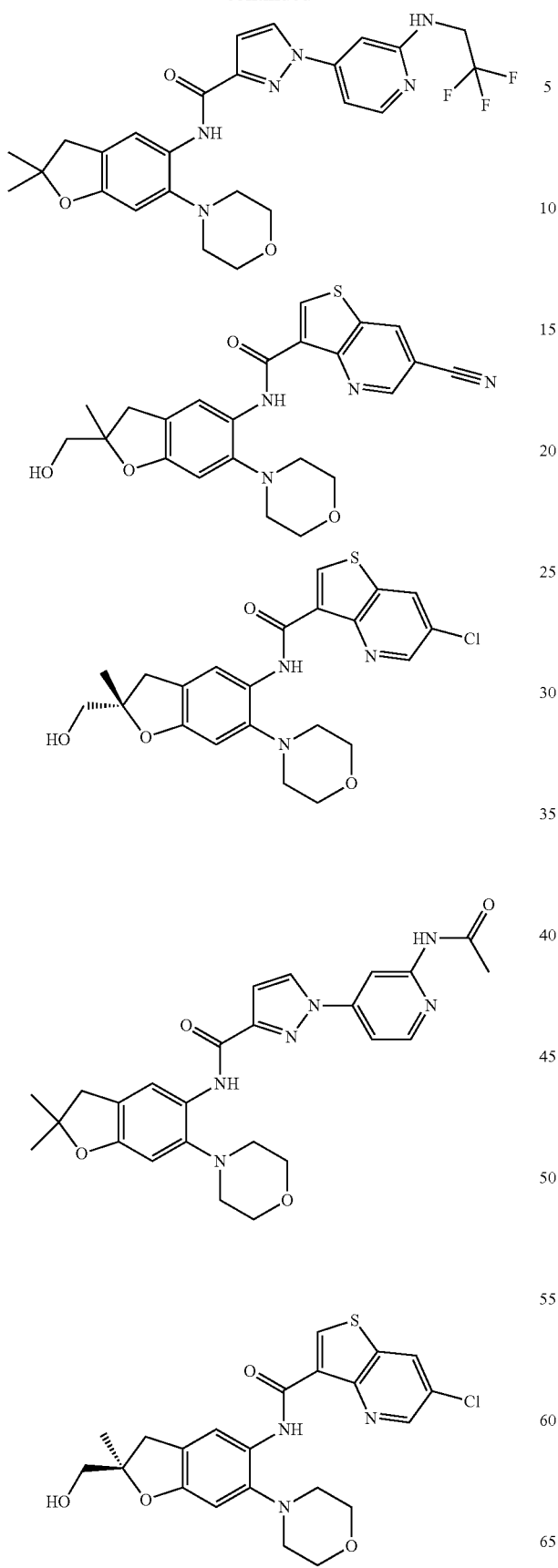
150
-continued
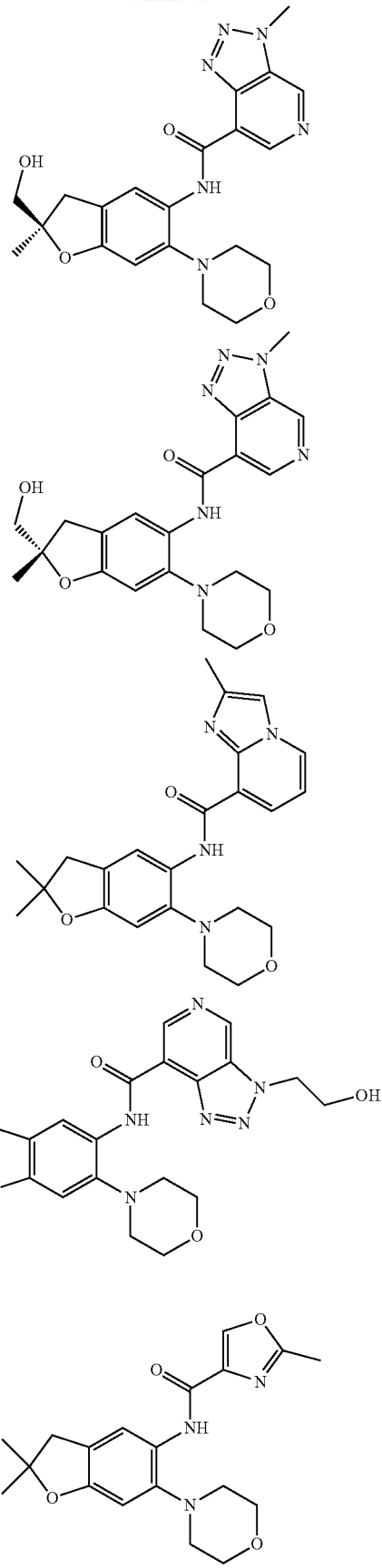

151
-continued
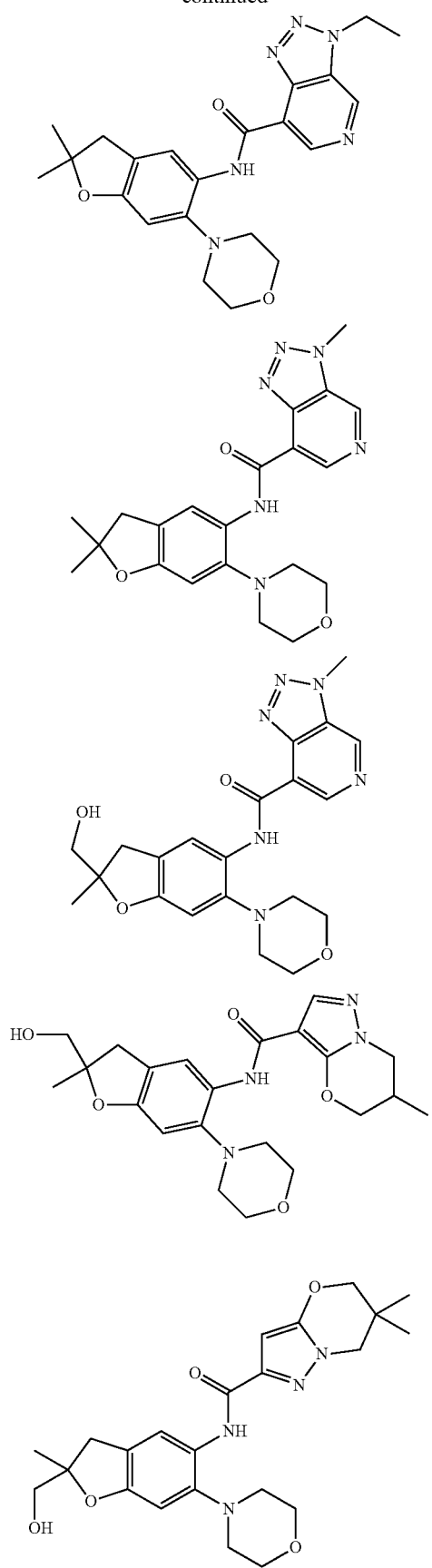
152
-continued
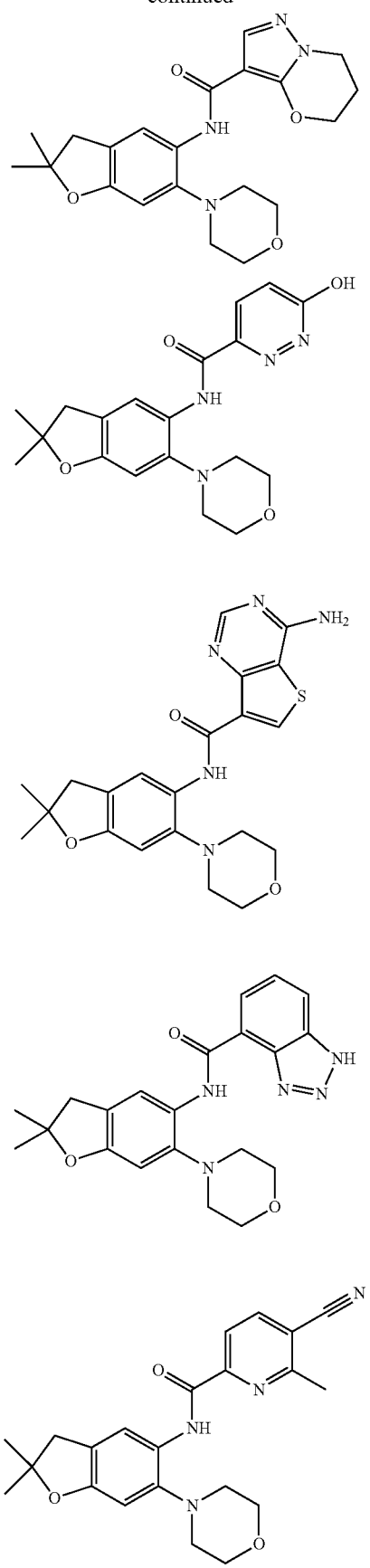

153
-continued
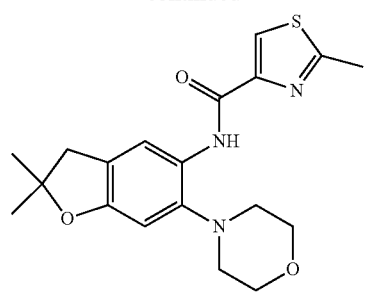
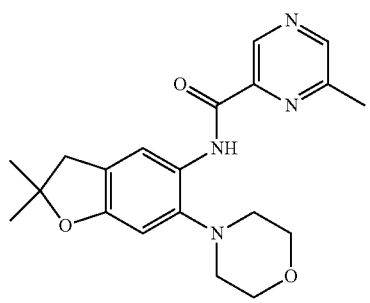
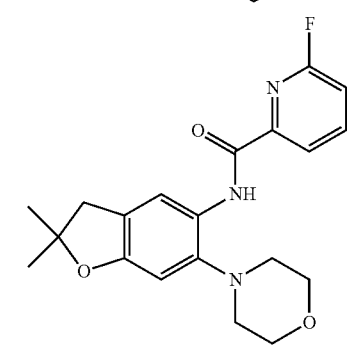
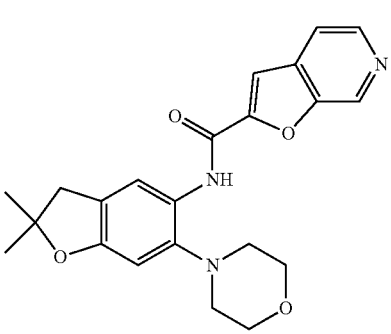
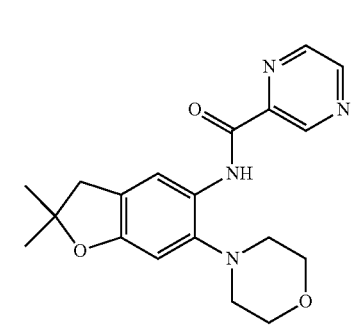
154
-continued
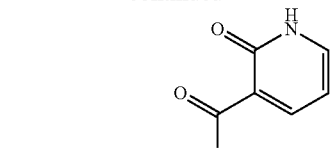
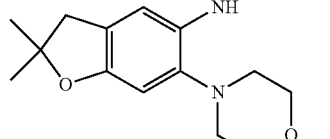
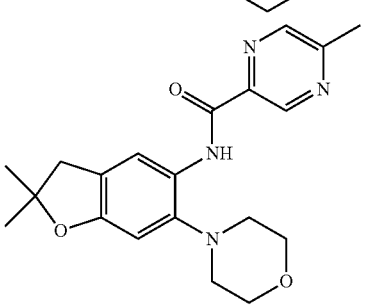
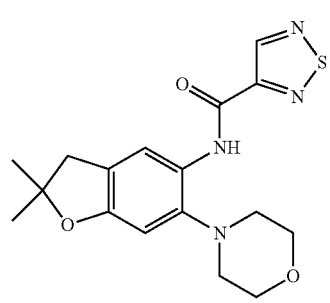
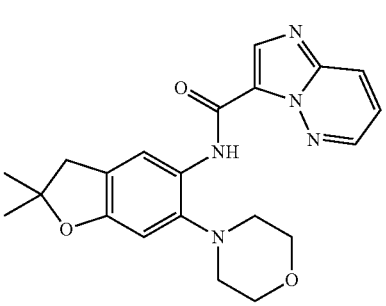
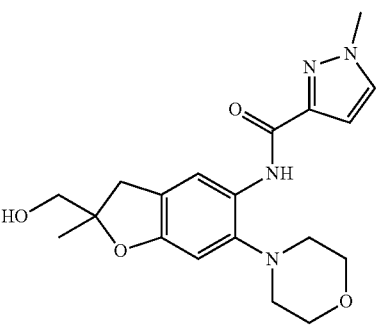

155
-continued
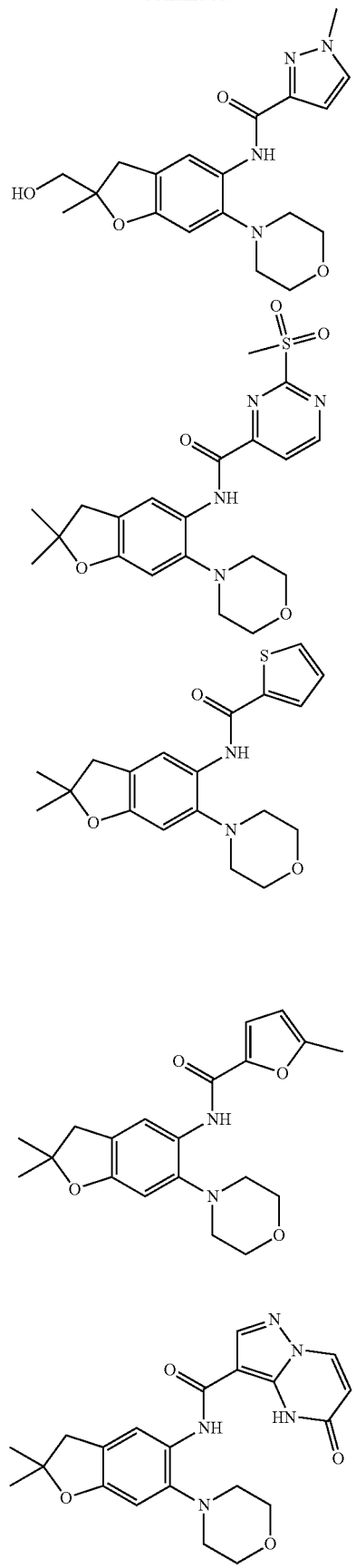
156
-continued
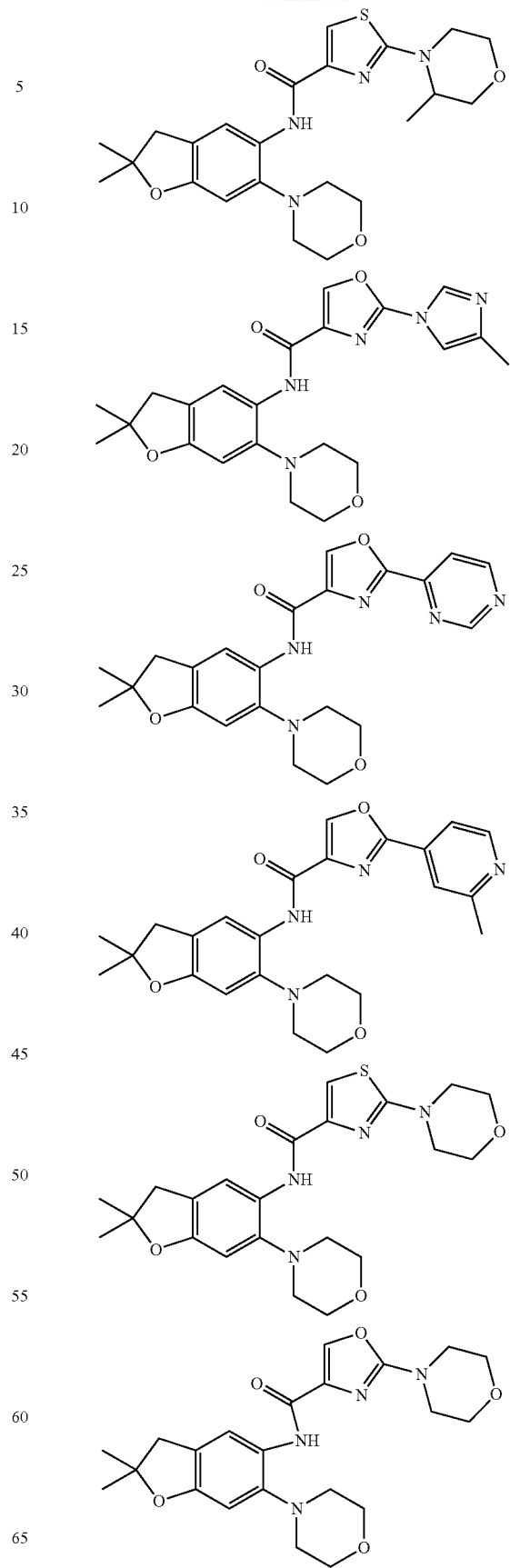

-continued
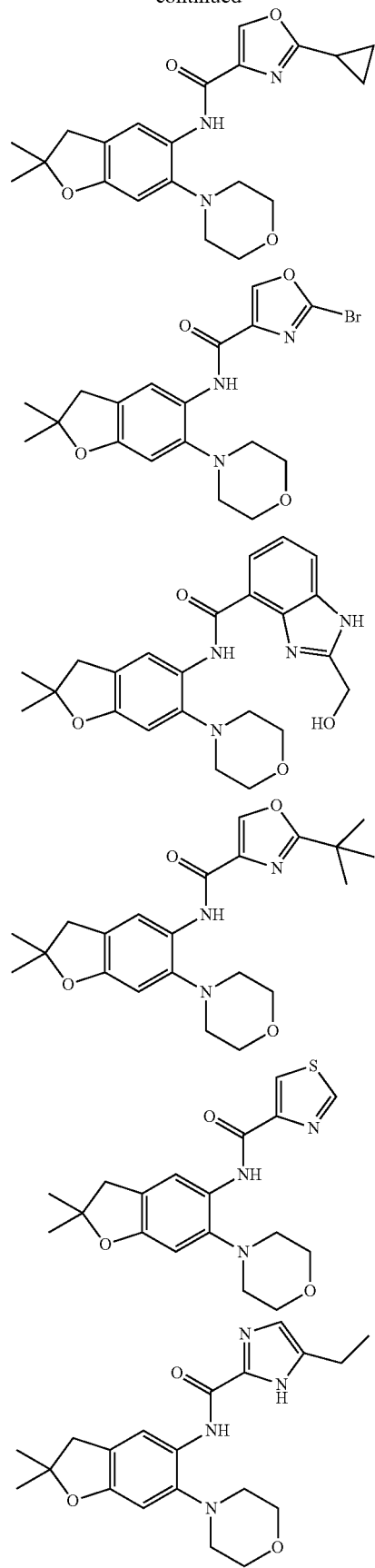
-continued
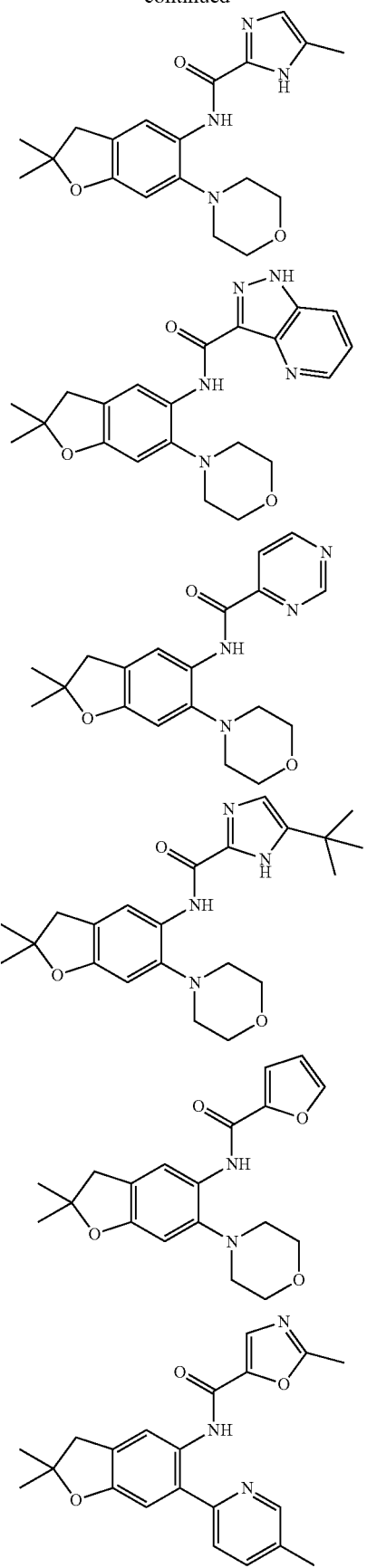

159
-continued
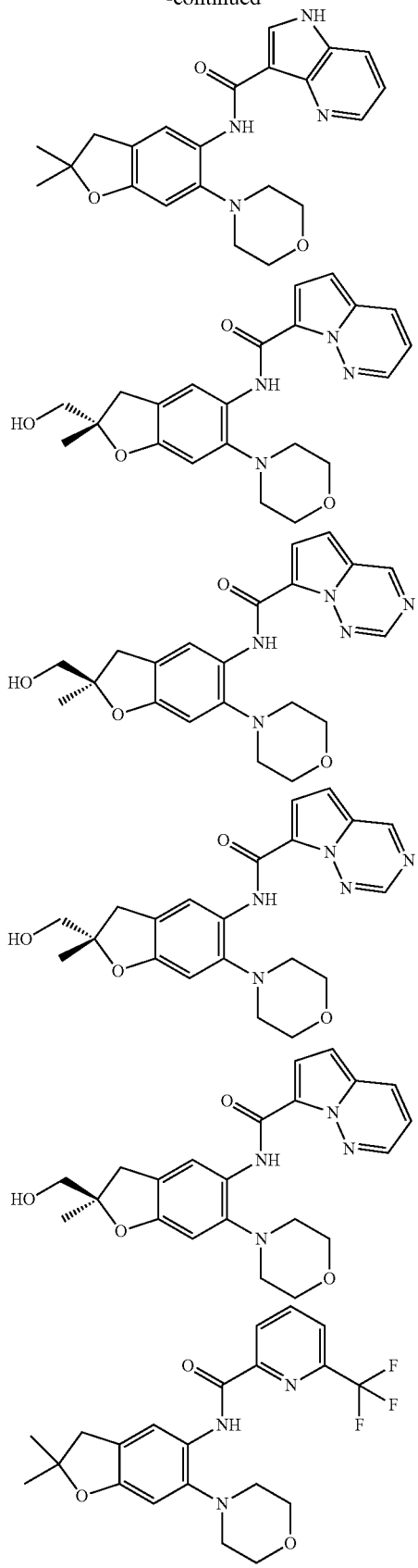
160
-continued
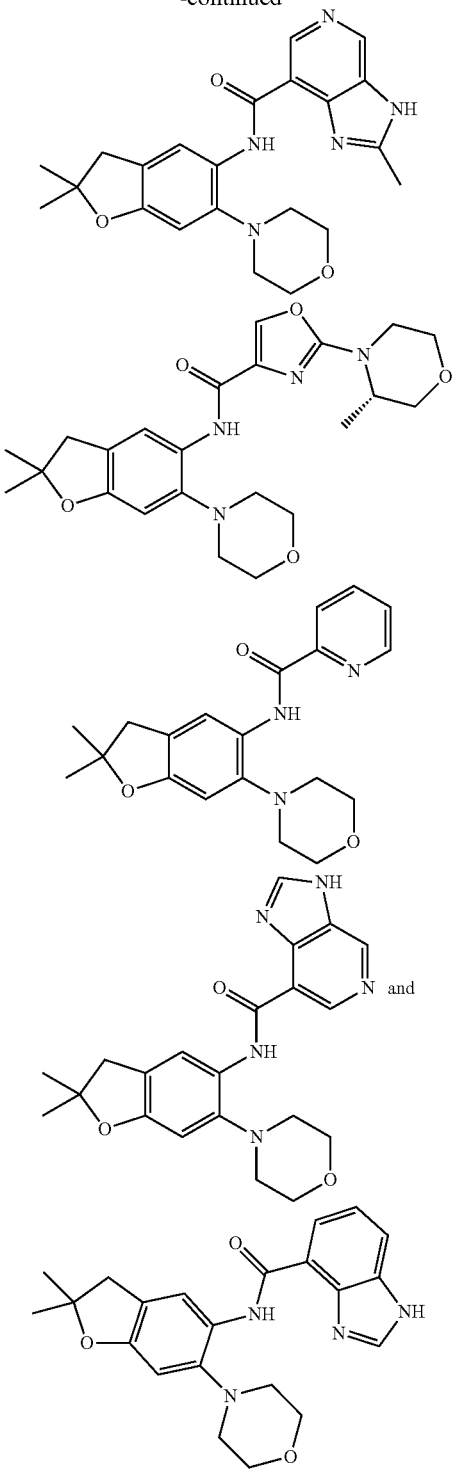
or a stereoisomer or pharmaceutically acceptable salt thereof.
18. A pharmaceutical composition comprising a compound of claim 1, or a stereoisomer or pharmaceutically acceptable salt thereof, and a pharmaceutically acceptable excipient, carrier or diluent.
* * * * *